US011441122B2

(12) United States Patent
Martin et al.

(10) Patent No.: US 11,441,122 B2
(45) Date of Patent: Sep. 13, 2022

(54) REGULATORY T CELL EPITOPES

(71) Applicants: EpiVax, Inc., Providence, RI (US); Food and Drug Adminstration, Silver Spring, MD (US)

(72) Inventors: William Martin, Providence, RI (US); Amy S. Rosenberg, Silver Spring, MD (US)

(73) Assignees: EpiVax Inc., Providence, RI (US); The United States of America, as Represented by the Secretary, Department of Health and Human Services Food and Drug Administration, Silver Spring, MD (US)

( * ) Notice: Subject to any disclaimer, the term of this patent is extended or adjusted under 35 U.S.C. 154(b) by 328 days.

(21) Appl. No.: 16/753,522

(22) PCT Filed: Oct. 5, 2018

(86) PCT No.: PCT/US2018/054595
§ 371 (c)(1),
(2) Date: Apr. 3, 2020

(87) PCT Pub. No.: WO2019/071116
PCT Pub. Date: Apr. 11, 2019

(65) Prior Publication Data
US 2020/0308542 A1 Oct. 1, 2020

Related U.S. Application Data

(60) Provisional application No. 62/729,792, filed on Sep. 11, 2018, provisional application No. 62/568,630, filed on Oct. 5, 2017, provisional application No. 62/568,625, filed on Oct. 5, 2017.

(51) Int. Cl.
*C12N 5/0783* (2010.01)
*C07K 14/52* (2006.01)
*A61K 38/00* (2006.01)

(52) U.S. Cl.
CPC ............ *C12N 5/0637* (2013.01); *C07K 14/52* (2013.01); *A61K 38/00* (2013.01); *C07K 2317/34* (2013.01)

(58) Field of Classification Search
None
See application file for complete search history.

(56) References Cited

U.S. PATENT DOCUMENTS

| 4,458,066 A | 7/1984 | Caruthers et al. |
| 4,522,811 A | 6/1985 | Eppstein et al. |
| 5,328,470 A | 7/1994 | Nabel et al. |
| 7,884,184 B2 | 2/2011 | De Groot et al. |
| 2009/0018067 A1 | 1/2009 | De Groot et al. |
| 2016/0030555 A1 | 2/2016 | Kishimoto et al. |

FOREIGN PATENT DOCUMENTS

| EP | 1598367 A1 | 11/2005 |
| WO | 2007101106 A2 | 9/2007 |
| WO | 2016005564 A2 | 1/2016 |
| WO | 2019210187 A1 | 10/2019 |

OTHER PUBLICATIONS

Adams, et al.. "Hindered Dialkylamino Nucleoside Phosphite Reagents in the Synthesis of Tow DNA 51-Mers", J. Am. Chem. Soc. (1983), pp. 661-663.
Akdis, et al., "Immune Responses in Healthy and Allergic Individuals Are Characterized by a Fine Balance between Allergen-specific T Regulatory 1 and T Helper 2 Cells", J. Exp. Med., (Jun. 7, 2004), pp. 1567-1575.
Ausubel, et al., "Current Protocols in Molecular Biology", John Wiley & Sons, (1992).
Beaucage, et al., "Deoxynucleoside Phosphoramidites—A New Class of Key Intermediates for Deoxypolynucleotide Synthesis", Tetrahedron Letters, (1981), pp. 1859-1862.
Belousov, et al., "Sequence-specific targeting and covalent modification of human genomic DNA", Nucleic Acids Research, (1997), pp. 3440-3444.
Bettini, et al., "Cutting Edge: Accelerated Autoimmune Diabetes in the Absence of LAG-3", http://www.jimmunol.org/content/187/7/3493, J. Immunol., (2011), pp. 3493-3498.
Blommers, et al., "Effects of the Introduction of L-Nucleotides into DNA. Solution Structure of the Heterochiral Duplex d(G-C-G-(L)T-G-C-G)-d(C-G-C-A-C-G-C) Studied by NMR Spectroscopy", Biochemistry, (1994), pp. 7886-7896.
Boisvert, et al., "Alpha2beta1 integrin is the major collagen-binding integrin expressed on human Th17 Cells", Eur. J. Immunol., (2010), pp. 2710-2719.
Brannigan, et al., "Protein engineering 20 years on", Nature Reviews Molecular Cell Biology 3, (Dec. 2002), pp. 964-970.
Brown, et al., "Chemical Synthesis and Cloning of a Tyrosine tRNA Gene", Methods in Enzymology, (1979), pp. 109-151.
Bruniquel, et al., "Regulation of Expresssion of the human lymphocyte activation gene-3 (LAG-3) molecule, a ligand for MHC class II", Immunogenetics, (1998), pp. 116-124.
Butterfield, "Dendritic cells in cancer immunotherapy clinical trials: are we making progress?", Frontiers in Immunology, (Dec. 2013), pp. 1-7.
Camisaschi, et al., "LAG-3 Expression Defines a Subset of CD4+ CD25highFoxp3+ Regulatory T Cells That are expanded at Tumor Sites", http://www.jimmunol.org/content/184/11/6545, J. Immunol., (2010), pp. 6545-6551.
Charbonnier, et al., "Immature Dendritic Cells Suppress Collagen-Induced Arthritis by In Vivo Expansion of CD49b+ Regulatory T Cells", http://www.jimmunol.org/content/177/6/3806, J. Immunol., (2006), pp. 3806-3813.

(Continued)

*Primary Examiner* — Amy E Juedes
(74) *Attorney, Agent, or Firm* — Dinsmore & Shohl LLP; Weston R. Gould

(57) ABSTRACT

The present is directed to compositions comprising regulatory T cell epitopes, wherein said epitopes comprise a polypeptide comprising at least a portion of SEQ NOS: 1-14, fragments and/or variants thereof, as well as methods of producing and using the same.

9 Claims, 39 Drawing Sheets

Specification includes a Sequence Listing.

(56) References Cited

OTHER PUBLICATIONS

Chaudhry, et al., "Interleukin-10 Signaling in Regulatory T Cells is Required for Suppression of Th17 Cell-Mediated Inflammation", Immunity 34., (Apr. 22, 2011), pp. 566-578.
Chen, et al., "Gene Therapy for brain tumors: Regression of experimental gliomas by adenovirus-mediated gene transfer in vivo", Proc. Natl. Acad. Sci. USA, (Apr. 1994), pp. 3054-3057.
De Groot, et al., "From genome to vaccine: in silico predictions, ex vivo verification", www.elsevier.com/locate/vaccine/Vaccine 19, (2001), pp. 4385-4395.
De Groot, et al., "Mapping cross-clade HIV-1 vaccine epitopes using a bioinformatics approach", www.elseviere.com/locate/vaccine. Vaccine 21, (2003) pp. 4486-4505.
De Groot, et al., "Reducing risk, improving outcomes: Bioengineering less immunogenic protein therapeutics", www.elsevier.com/locate/yclim, Clinical Immunology, (2009), pp. 189-201.
De Groot, et al., "An Interactive Web Site Providing Major Histocompatibility Ligand Predictions: Application to HIV Research", Aids Research and Human Retroviruses, (1997), pp. 529-531.
Dimitrov, "Therapeutic Proteins", Methods Mol Biol., (2012), pp. 1-26.
Dissanayake, et al., "Peptide-Pulsed Dendritic Cells Have Superior Ability to Induce Immune-Mediated Tissue Destruction Compared to Peptide with Adjuvant", PLOS ONE, (Mar. 2014), pp. 1-10.
Feng, et al., "HBcAg-specific CD4+CD25+ regulatory T cells modulate immune tolerance and acute exacerbation on the natural history of chronic hepatitis B virus infection", Journal of Biomedical Science, (2007), pp. 43-57.
Frenkel, et al., "7,12-Dimethylbenz[A]Anthracene Induces Oxidative DNA Modification in Vivo", Free Radical Biology & Medicine, (1995), pp. 373-380.
Groux, et al., "A CD4+ T-cell subset inhibits antigen-specific T-cell responses and prevents colitis", Nature, (Oct. 16, 1997), pp. 737-742.
Haringer, et al., "Identification and characterization of IL-10/IFN-y-producing effector-like T cells with regulatory function in human blood", J. Exp. Med., (2009), pp. 1009-1017.
Joshi, et al., "Molecular analysis of expression and function of hFcyRIIb1 and b2 isoforms in myeloid cels", www.elsevier.com/locate/molimm, Molecular Immunology 43, (2006), pp. 839-850.
Kassiotis, et al., "Functional Specialization of Memory Th Cells Revealed by Expression of Integrin CD49b", http://www.jimmunol.org/content/177/2/968, J. Immunol., (2006), pp. 968-975.
Lee, et al., "Induction and molecular signature of pathogenic Th17 cells", Nat Immunol., (2012), pp. 991-999.
Mack, et al., "Common and Well-Documented HLA Alleles: 2012 Update to the CWD Catalogue", Tissue Antigens, (2013), pp. 194-203.
Magnani, et al., "Killing of myeloid ACSs via HLA class I, CD2 and CD226 defines a novel mechanism of suppression by human Tr1 cells", Eur. J Immunol., (2011), pp. 1652-1662.
Maynard, et al., "Regulatory T cells expressing interleuken 10 develop from Foxp3+ and Foxp3− precursor cells in the absence of interleukin 10", Nature Immunology, (Sep. 2007), pp. 931-941.
Mudd, et al., "Regulatory T Cells and Systemic Lupus Erythematosus", Scandinavian Journal of Immunology, (2006) pp. 211-218.
Narang, et al., "Improved Phosphotriester Method for the Synthesis of Gene Fragments", Methods in Enzymology, (1979), pp. 90-98.
Noble, et al., "Separation of Blood Leukocytes by Ficoll* Gradient", Can. Vet. Jour., (May 1967), pp. 110-111.
Okamura, et al., "CD4+CD25-LAG3+ regulatory T cells controlled by the transcription factor Egr-2", PNAS, (Aug. 18, 2009), pp. 13974-13979.
Pearse, et al., "SHIP Recruitment Attenuates FcyRIIB-Induced B Cell Apoptosis", Immunity, (Jun. 1999), pp. 753-760.
Pipe, et al., "Differential Interaction of Coagulation Factor VIII and Factor V with Protein Chaperones Calnexin and Calreticulin", The Journal of Biological Chemistry, (Apr. 3, 1998), pp. 8537-8544.
Pot, et al., "Type 1 regulatory T cells (Tr1) in autoimmunity", www.elsevier.com/locate/ysmim, Seminars in Immunology 23, (2011), pp. 202-208.
Ravetch, et al., "Structrual Heterogeneity and Functional Domains of Murine Immunoglobulin G Fe Receptors", Science, (Nov. 7, 1986), pp. 718-725.
Roncarlo, et al., "Clinical tolerance in allogeneic hematopoietic stem cell transplantation", John Wiley & Sons, Immunological Reviews, (2011), pp. 145-163.
Roncarlo, et al., "Regulatory T-cell immunotherapy for tolerance to self antigens and alloantigens and humans", Nature Reviews/Immunology, (Aug. 2007), pp. 585-598.
Schafer, et al., "Prediction of well-conserved HIV-1 ligands using a matrix-based algorithm, EpiMatrix", Vaccine, vol. 16, (1998), pp. 1880-1884.
Shevach, "CD4+CD25+ Supressor T Cells: More Questions than Answers", Nature Reviews/Immunology, vol. 2, (Jun. 2002), pp. 389-400.
Steere, et al., "Antibiotic-refractory Lyme arthritis is associated with HLA-DR molecules that bind a Borrelia burgdorferi peptide", www.jem.org/cgi/doi/10.1084/jem.20052471, Jem, (Apr. 17, 2006), pp. 961-971.
Sturniolo, et al., "Generation of tissue-specific and promiscuous HLA ligand databases using DNA microarrays and virtual HLA class II matrices", Nature Biotechnology, (Jun. 1999), pp. 555-561.
Turanli-Yildiz, et al., "Protein Engineering Methods and Applications", www.intechopen.com, (Feb. 2012), pp. 33-58.
Extended European Search Report pertaining to corresponding European Patent Application No. 188641617, dated May 10, 2021.
De Groot et al., "Identification of a Tolerogenic Factor V Peptide and its Potential Role in Factor VIII Tolerance INduction", 2018.

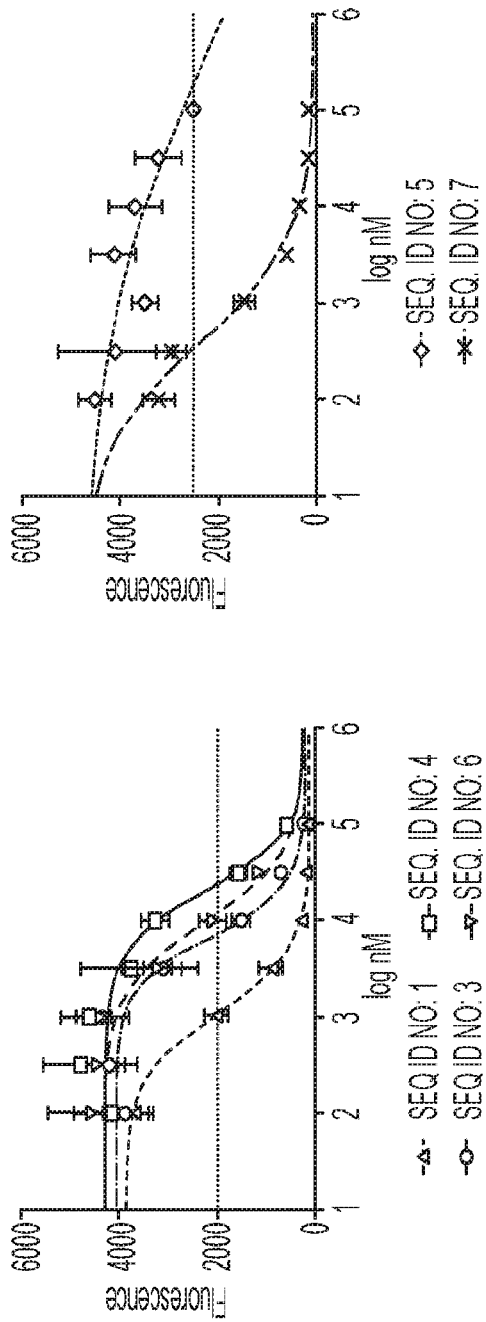
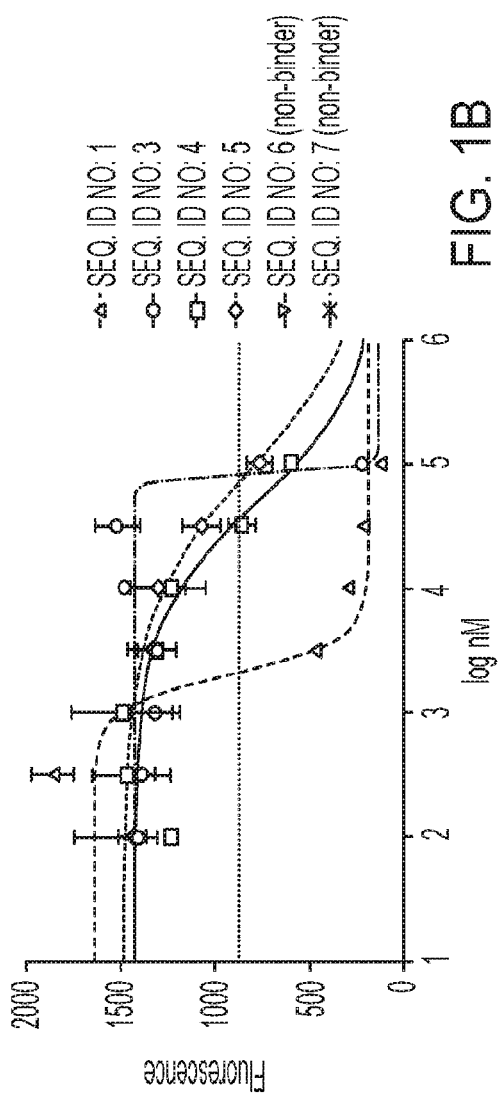
FIG. 1A
FIG. 1B

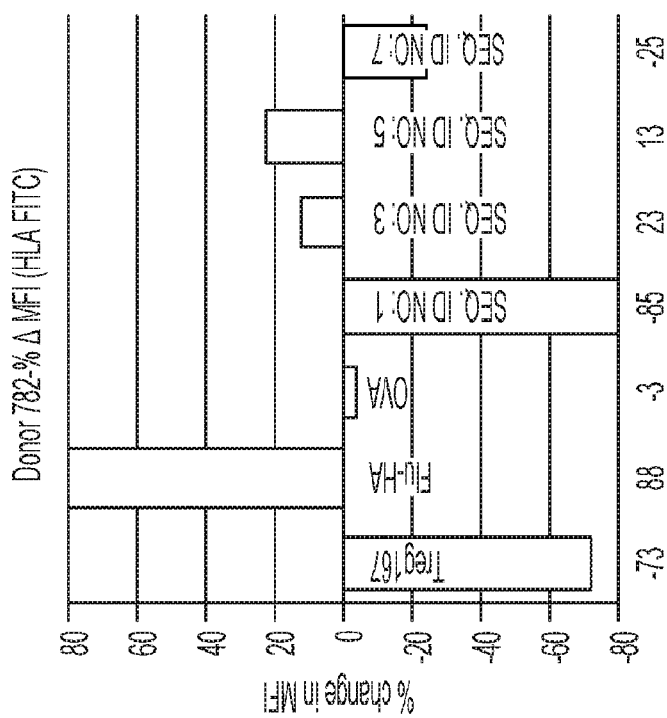
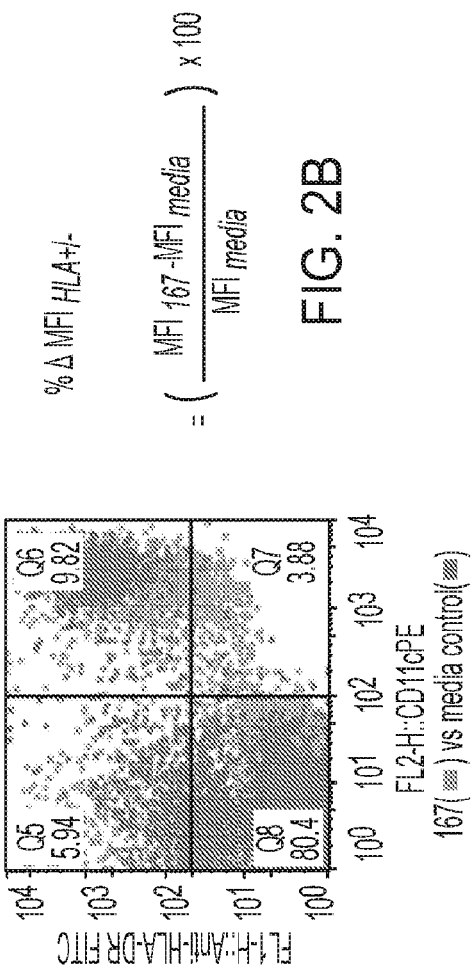
FIG. 2C
FIG. 2B
FIG. 2A

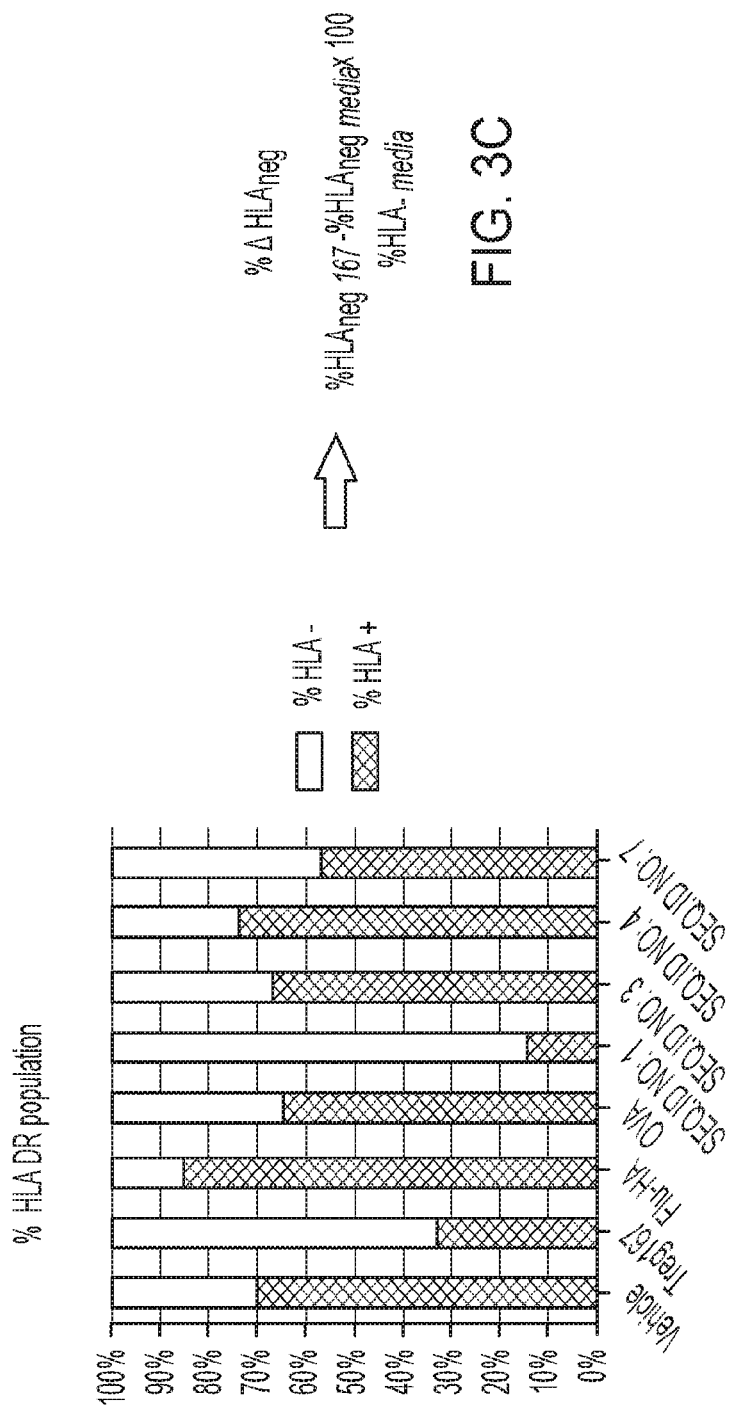

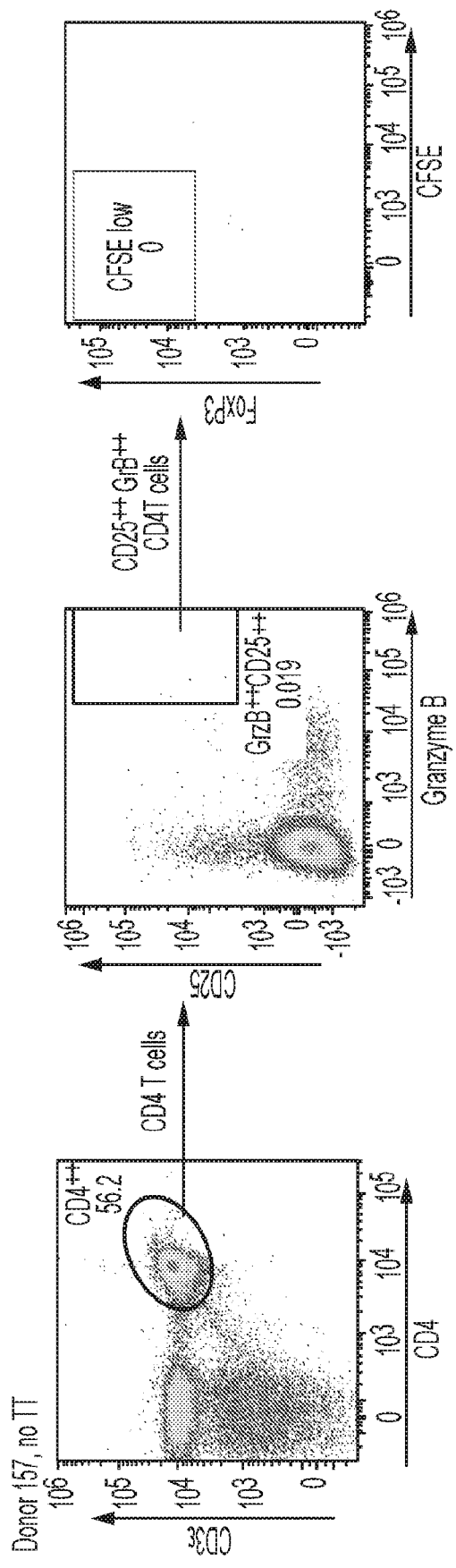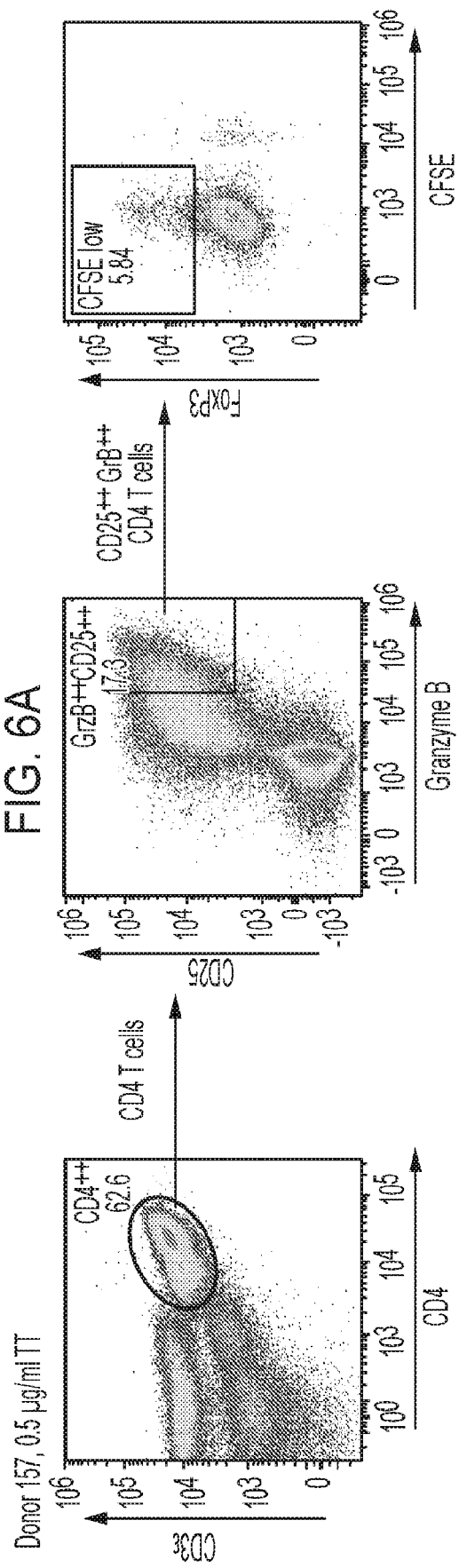

| Source | Start Peptide | Extended Peptide |
|---|---|---|
| Human | IHFTGHSFI (SEQ ID NO: 8) | ILTIHFTGHSFIYGK (SEQ ID NO: 1) |
| Human | IHFSGHVFT (SEQ ID NO: 9) | IHSIHFSGHVFTVRK (SEQ ID NO: 2) |

FIG. 12

Example EpiBar
Accession: Influenza—Sequence: HA306-318

| Flame Start | AA Sequence | Flame Stop | DRB1*0101 Z score | DRB1*0301 Z score | DRB1*0401 Z score | DRB1*0701 Z score | DRB1*0801 Z score | DRB1*1101 Z score | DRB1*1301 Z score | DRB1*1501 Z score | HITS |
|---|---|---|---|---|---|---|---|---|---|---|---|
| 306 | PRYVKQNTL | 314 | 1.34 | 1.40 | | 2.06 | | | | 1.28 | 1 |
| 307 | RYVKQNTLK | 315 | | | | | | | | | |
| 308 | YVKQNTLKL | 316 | 3.33 | 1.97 | 3.15 | 3.27 | 1.96 | 1.99 | 2.37 | 2.36 | 8 |
| 309 | VKQNTLKLA | 317 | | | | | | 1.59 | 1.67 | | 1 |
| 310 | KQNTLKLAT | 318 | | | | | | | | | |

Z score indicates the potential of a 9-mer frame to bind to a given HLA allele; the strength of the score is indicated by the blue as shown below:

| | | | | |
|---|---|---|---|---|
| Cluster Regions Outlined | Z scores in top 1% | Z scores in top 5% | Z scores in top 10%* | remaining scores masked* |

Assessments performed: 40 Deviation from Expectation: 17.62

FIG. 19

| | Source | Start | Peptide | Epx Score for DRB1*1501 | Epx Cluster Score | Extended Peptide for Synthesis | Comment |
|---|---|---|---|---|---|---|---|
| 1. | Human FV | 179 | IEDENSGLI | 2.08 | 6.46 | ENLIEDENSGLIGPL | Not conserved in mouse |
| | Human FVIII | 184 | VKDLNSGLI | 2.23 | 13.35 | VDLYKDLNSGLIGAL | |
| 2. | Human FV | 432 | KIVFKNMAS | 2.01 | 29.82 | DILKIVFKNMASRPY | Poor P1 anchor |
| | Human FVIII | 104 | VITLKNMAS | 2.44 | 31.42 | DTVVITLKNMASHPV | |
| 3. | Human FV | 435 | FKNMASRPY | 2.01 | 19.54 | KIVFKNMASRPYSIY | Selected |
| | Human FVIII | 484 | FKNQASRPY | 1.79 | 27.14 | LIIFKNQASRPYNIY | |
| | Human FVIII | 107 | LKNMASHPV | 2.00 | 23.81 | VITLKNMASHPVSLH | Published |
| | Human FVIII | 1794 | FRNQASRPY | 1.76 | 14.05 | MVTFRNQASRPYSFY | |
| 4. | Human FV | 585 | IMSTINGYV | 2.02 | -1.42 | ESNIMSTINGYVPES | Selected |
| | Human FVIII | 632 | IMHSINGYV | 2.02 | 6 | ASNIMHSINGYVFDS | Published |
| 5. | Human FV | 624 | IHFTGHSFI | 2.12 | 0.49 | ITLIHFTGHSFIYGK | Selected |
| | Human FVIII | 1975 | IHFSGHVFT | 1.93 | 1.36 | IHSIHFSGHVFTVRK | |
| 6. | Human FV | 932 | LLLKQSNSS | 1.93 | 59.71 | SDLLLKQSNSSHLP | Poor P1 anchor |
| | Human FVIII | 1425 | RVLFQDNSS | 2.16 | 9.75 | YLTRVLFQDNSSHLP | Similar to FV 435 |
| 7. | Human FV | 1660 | FKNLASRPY | 2.00 | 28.85 | QVRFKNLASRPYSLH | Published |
| | Human FVIII | 107 | LKNMASHPV | 2.00 | 23.81 | VITLKNMASHPVSLH | |
| | Human FVIII | 484 | FKNQASRPY | 1.79 | 27.14 | LIIFKNQASRPYNIY | |
| | Human FVIII | 1794 | FRNQASRPY | 1.76 | 14.05 | MVTFRNQASRPYSFY | |
| 8. | Human FV | 1805 | FHAINGMIY | 2.19 | 4.63 | SHEFHAINGMIYSLP | Selected |
| | Human FVIII | 1937 | FHAINGYIM | 2.32 | 12.8 | NYRFHAINGYIMDTL | |
| 9. | Human FV | 2130 | IKKITAIIT | 2.40 | 21.98 | LLKIKKITAIITQGC | Not conserved in mouse |
| | Human FVIII | 1058 | FKKVTPLIH | 2.08 | 12.45 | DIEFKKVTPLIHDRM | |
| 10. | Human FV | 2188 | VKNFNPPI | 2.95 | 10.32 | KGHVKNFNPPIISR | |
| | Human FVIII | 2155 | KHNIFNPPI | 1.72 | -2.39 | SGIKHNIFNPPIIAR | Poor P1 anchor |

Anchor residues in Black   Conserved TCR Contacts in Sea Green   Mis-Matched TCR Contacts in Red

FIG. 20

| | Source | Start | Peptide | Epx Score for DRB1*1501 | Epx Cluster Score | Extended Peptide for Synthesis | Comment |
|---|---|---|---|---|---|---|---|
| 1. | Human FV | 551 | FDENKSWYL | 1.56 | 3.08 | FAVFDENKSWYLEDN | Selected |
| | Human FVIII | 1902 | FDETKSWYF | 0.80 | 1.04 | FTIFDETKSWYFTEN | Matched on DR7 |
| | Human FVIII | 598 | FDENRSWYL | 1.55 | 3.07 | FSVFDENRSWYLTEN | Matched on DR1 and DR7 |
| 2. | Human FV | 1740 | IHSGLIGPL | 1.71 | 4.89 | EKDIHSGLIGPLLI | Selected |
| | Human FVIII | 1866 | VHSGLIGPL | 1.60 | 2.9 | EKDVHSGLIGPLLV | Matched on DR3 and DR7 |

Anchor residues in Black
Conserved TCR Contacts in Sea Green
Mis-Matched TCR Contacts in Red

FIG. 21

| Donor/HLA DRB1/Exp# | Peptide | Visual shift in MFI of HLA | % Δ MFI of HLA for all CD11c+ | % Δ in HLAneg population | Visual shift in MFI of CD86 | % Δ MFI of CD86+/CD11c+ | % Δ in CD86neg population |
|---|---|---|---|---|---|---|---|
| *Donor 767* | | | | | | | |
| | 167 | + | -36 | 134 | + | 74 | -13 |
| *1001(N/A) | Flu-HA306-318 | +/- | -25 | 49 | + | -19 | -10 |
| *1601 | OVA323-339 | +/- | -35 | 87 | - | -19 | 14 |
| | SEQ. ID NO:1 | + | -82 | 570 | +/- | 60 | 73 |
| | SEQ. ID NO:3 | + | -27 | 67 | +/- | -7 | 51 |
| 3.0b | SEQ. ID NO:5 | + | -38 | 96 | +/- | 9 | 56 |
| | SEQ. ID NO:7 | + | -46 | 126 | +/- | -20 | 33 |
| *Donor 771* | | | | | | | |
| | 167 | + | -38 | 69 | + | 42 | -48 |
| *0101 | Flu-HA306-318 | - | 6 | -24 | +/- | -16 | 2 |
| *0701 | OVA323-339 | + | -56 | 126 | - | -8 | -2 |
| | SEQ. ID NO:1 | + | -89 | 314 | +/- | 15 | 51 |
| 3.0b | SEQ. ID NO:3 | + | -44 | 97 | +/- | -16 | 50 |
| | SEQ. ID NO:5 | + | -51 | 90 | + | -19 | 19 |
| | SEQ. ID NO:7 | + | -58 | 129 | +/- | -11 | -2 |
| *Donor 778* | | | | | | | |
| | 167 | - | 18 | 54 | + | 112 | -33 |
| *0407 | Flu-HA306-318 | - | 48 | -56 | - | -10 | -8 |
| *0701 | OVA323-339 | - | 27 | -26 | - | 21 | 10 |
| | SEQ. ID NO:1 | + | -62 | 210 | + | -3 | -21 |
| 3.0a | SEQ. ID NO:3 | - | 5 | -6 | - | 6 | 11 |
| | SEQ. ID NO:5 | - | 3 | -6 | - | 6 | 47 |
| | SEQ. ID NO:7 | - | 13 | -22 | - | 10 | 33 | red = a decrease in HLA       red = decrease in CD86

FIG. 22

| Donor/HLA DRB1/Exp# | Peptide | Visual shift in MFI of HLA | % Δ MFI of HLA for all CD11c+ | % Δ in HLAneg population | Visual shift in MFI of CD86 | % Δ MFI of CD86+/CD11c+ | % Δ in CD86neg population |
|---|---|---|---|---|---|---|---|
| Donor 782 | | | | | | | |
| | 167 | + | -73 | 125 | + | 32 | 12 |
| *0701 | Flu-HA306-318 | + | 88 | -51 | - | -15 | 80 |
| *0701 | OVA323-339 | - | -3 | 19 | - | -5 | 83 |
| | SEQ. ID NO:1 | + | -85 | 185 | + | -28 | 244 |
| 3.0a | SEQ. ID NO:3 | - | 13 | 11 | - | 3 | 67 |
| | SEQ. ID NO:5 | - | -23 | -12 | - | 21 | 114 |
| | SEQ. ID NO:7 | + | -25 | 44 | - | 13 | 86 |
| Donor 784 | | | | | | | |
| | 167 | + | -69 | 460 | + | 87 | 11 |
| *0301 | Flu-HA306-318 | - | -41 | 51 | - | 1 | 9 |
| *1601 | OVA323-339 | - | -50 | 126 | - | 15 | -1 |
| | SEQ. ID NO:1 | + | -54 | 105 | + | -61 | 306 |
| | SEQ. ID NO:3 | + | -19 | 97 | + | 36 | 33 |
| 3.0a | SEQ. ID NO:5 | + | -18 | 61 | + | 43 | 45 |
| | SEQ. ID NO:7 | + | -40 | 193 | + | 84 | -1 | red = a decrease in HLA     red = decrease in CD86

FIG. 22 continued

| Peptide Name | Peptide Sequence | Features | HLA DRB1 | | | | |
|---|---|---|---|---|---|---|---|
| | | | *0101 | *0301 | *0701 | *1101 | *1501 |
| SEQ ID NO: 1 | Ac-ILTIHFTGHSFIYGK-amide | Max EPX | 1.25 | 1.45 | 2.00 | 0.79 | 2.12 |
| | | IC50 | 1,078 | 1,907 | 472 | 1,528 | 549 |
| | | Result | FN | FN | TP | FN | TP |
| SEQ ID NO: 3 | Ac-KIVFKNMASRPYSIY-amide | Max EPX | 2.91 | 2.45 | 2.01 | 2.91 | 2.01 |
| | | IC50 | 7,452 | Non-binder | 13,265 | 1,227 | 189 |
| | | Result | TP | FP | TP | TP | TP |
| SEQ ID NO: 4 | Ac-FAVFDENKSWYLEDN-amide | Max EPX | 1.86 | 1.38 | 2.05 | 1.61 | 1.56 |
| | | IC50 | 24,216 | 17,275 | 1,234 | Non-binder | 17,885 |
| | | Result | TP | FN | TP | TN | FN |
| SEQ ID NO: 5 | Ac-NIMSTINGYVPES-amide | Max EPX | 1.6 | 1.13 | 2.32 | 1.27 | 2.02 |
| | | IC50 | -100,000 | 70,057 | 2,818 | Non-binder | 6,565 |
| | | Result | FN | FN | TP | TN | TP |
| SEQ ID NO: 6 | Ac-EKDIHSGLIGPLLI-amide | Max EPX | 1.64 | 1.82 | 2.19 | 0.77 | 1.71 |
| | | IC50 | 11,952 | Non-binder | Non-binder | Non-binder | 6,318 |
| | | Result | TP | FP | FN | TN | TP |
| SEQ ID NO: 7 | Ac-SHEFHAINGMIYSLP-amide | Max EPX | 2.29 | 1.75 | 1.35 | 1.99 | 2.19 |
| | | IC50 | 342 | Non-binder | 971 | 2,286 | 1,548 |
| | | Result | TP | FP | FN | TP | TP |

FIG. 25

REGULATORY T CELL EPITOPES

RELATED APPLICATIONS

This application is a National Stage Entry under 35 U.S.C. 0.5371 of International Patent Application No. PCT/US2018/054595, filed Oct. 5, 2018, which claims priority to U.S. Provisional Patent Application Ser. No. 62/568,625, filed Oct. 5, 2017, U.S. Provisional Patent Application Ser. No. 62/568,630, filed Oct. 5, 2017, and U.S. Provisional Patent Application Ser. No. 62/729,792, filed Sep. 11, 2018. The entire contents of all of the above-listed applications are incorporated by reference herein.

SEQUENCE LISTING

The instant application contains a Sequence Listing which has been submitted in ASCII format via EFS-Web and is hereby incorporated by reference in its entirety. Said ASCII copy, created on Oct. 4, 2018, is named EPV_0008WO SEQUENCE Listing ST25.txt and is 114 KB in size.

FIELD OF THE INVENTION

The present disclosure generally relates to a novel class of regulatory T cell epitopes (termed "Tregitopes"). The present disclosure provides Tregitope compositions (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) as well as methods for their preparation and use.

BACKGROUND

Artificial induction of tolerance to self or to foreign antigens is the goal of therapy for autoimmunity, transplantation allergy and other diseases. Immune response targeting autologous and non-autologous therapeutic proteins often limits clinical efficacy. Immune modulating treatments, inducing tolerance to therapeutic proteins compositions, may reduce the formation of anti-drug antibodies (ADA) improving clinical outcomes. Until recently, therapeutic tolerance induction relied on broad-based immune cell depleting therapies. These broad-based approaches weaken the immune system in general and leave many subjects vulnerable to opportunistic infections, autoimmune attack and cancer. There is a need in the art for less aggressive and more targeted approaches to the induction of immune tolerance.

Immune tolerance is regulated by a complex interplay between antigen presenting cells (APC), T cells, B cells, cytokines, chemokines, and surface receptors. Initial self/non-self discrimination occurs in the thymus during neonatal development where medullary epithelial cells express specific self protein epitopes to immature T cells. T cells recognizing self antigens with high affinity are deleted, but autoreactive T cells with moderate affinity sometimes avoid deletion and can be converted to so called 'natural' regulatory T cells ($T_{Reg}$) cells. These natural $T_{Reg}$ cells are exported to the periphery and help to control latent autoimmune response.

A second form of tolerance develops in the periphery. In this case activated T cells are converted to an 'adaptive' $T_{Reg}$ phenotype through the action of certain immune suppressive cytokines and chemokines such as IL-10, TGF-β and CCL19. The possible roles for these 'adaptive' $T_{Reg}$ cells include dampening immune response following the successful clearance of an invading pathogen, controlling excessive inflammation caused by an allergic reaction, controlling excessive inflammation caused by low level or chronic infection, or possibly controlling inflammatory response targeting beneficial symbiotic bacteria.

Naturally occurring $T_{Regs}$ (including both natural $T_{Regs}$ and adaptive $T_{Regs}$) are a critical component of immune regulation in the periphery. For example, upon activation of natural $T_{Regs}$ through their TCR, natural $T_{Regs}$ express immune modulating cytokines and chemokines. Activated natural $T_{Regs}$ may suppress nearby effector T cells through contact dependent and independent mechanisms. In addition, the cytokines released by these cells including, but not limited to, IL-10 and TGF-β, are capable of inducing antigen-specific adaptive $T_{Regs}$. Despite extensive efforts, with few exceptions, the antigen specificity of natural $T_{Regs}$, and more importantly natural $T_{Regs}$ circulating in clinically significant volumes, is still unknown.

There is need in the art for the identification of regulatory T cell epitopes contained in common autologous proteins ("Tregitopes"), compositions containing such Tregitopes, and for methods related to their preparation and use.

SUMMARY

The aim of the present disclosure is to provide novel, therapeutic regulatory T cell epitope compositions, including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and use of the same, e.g., to suppress an immune response in the body or more specifically to suppress an immune response in the body caused by the administration of a therapeutic agent to treat a medical condition.

The selective engagement and activation of naturally occurring $T_{Regs}$ (in aspects, including natural $T_{Regs}$ and/or adaptive $T_{Regs}$) through the use of Tregitope compositions and Tregitope-antigen compositions as disclosed herein, is therapeutically valuable as a means of treatment for any disease or condition marked by the presence of an unwanted immune response. Examples of such an unwanted immune response include the following: Autoimmune disease such as type 1 diabetes, MS, Lupus, and RA; Transplant related disorders such as Graft vs. Host disease (GVHD) and Host vs. Graft disease (HVGD); Allergic reactions; Immune rejection of biologic medicines such as monoclonal antibodies; the management of immune response targeting replacement proteins, e.g., but not limited to, Insulin, coagulation Factor VIII (FVIII), and/or coagulation Factor VIII supplements; the management of immune response targeting therapeutic toxins such as Botulinum toxin; and the management of immune response to infectious disease whether acute or chronic.

The present disclosure harnesses the functions of naturally occurring $T_{Regs}$ (in aspects, including natural $T_{Regs}$ and/or adaptive $T_{Regs}$), and in particular aspects, those cells that already regulate immune responses to foreign and self-proteins in the periphery (pre-existing or natural $T_{Regs}$). In aspects, the present disclosure provides Tregitope compositions, with such compositions including one or more of, e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein. $T_{Reg}$ activating regulatory T-cell epitopes may be hereinafter referred to as "a" or "the" "Tregitope" or "Tregitopes". In aspects, a Tregitope composition of the present disclosure may be either covalently bound, non-covalently bound, or in admixture with a specific target antigen.

In aspects, the present disclosure is directed to a polypeptide (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14. The phrase "consisting essentially of" is intended to mean that a polypeptide according to the present disclosure, in addition to the sequence according to any of SEQ ID NOS: 1-14 or a variant thereof, contains additional amino acids or residues that may be present at either terminus of the peptide and/or on a side chain that are not necessarily forming part of the peptide that functions as an MHC ligand and provided they do not substantially impair the activity of the peptide to function as a Tregitope. In aspects, an isolated, synthetic, or recombinant polypeptide ($T_{reg}$ activating regulatory T-cell epitope, Tregitope, or T-cell epitope polypeptide) comprises, consists of, or consists essentially of one or more of SEQ ID NOS: 1-2. In aspects, an isolated, synthetic, or recombinant polypeptide ($T_{reg}$ activating regulatory T-cell epitope, Tregitope, or T-cell epitope polypeptide) comprises, consists of, or consists essentially of the amino acid sequence of SEQ ID NO: 1. In aspects, a polypeptide comprises one or more of SEQ ID NOS: 1-14 of the present disclosure (in aspects, including fragments thereof of SEQ ID NOS: 1-14) joined to, linked to (e.g., fused in-frame, chemically-linked, or otherwise bound), and/or inserted into a heterologous polypeptide. In aspects, the one or more of SEQ ID NOS: 1-14 may be joined to, linked to (e.g., fused in-frame, chemically-linked, or otherwise bound), and/or inserted into a heterologous polypeptide as a whole, although it may be made up from a joined to, linked to (e.g., fused in-frame, chemically-linked, or otherwise bound), and/or inserted amino acid sequence, together with flanking amino acids of the heterologous polypeptide. In aspects, the present disclosure is directed to polypeptide (which, in aspects, may be an isolated, synthetic, or recombinant) having a sequence comprising one or more of SEQ ID NOS: 1-14, wherein said one or more of SEQ ID NOS: 1-14 is not naturally included in the polypeptide and/or said one or more of SEQ ID NOS: 1-14 is not located at its natural position in the polypeptide. In aspects, an isolated, synthetic, or recombinant polypeptide ($T_{reg}$ activating regulatory T-cell epitope, Tregitope, or T-cell epitope polypeptide) comprises one or more of SEQ ID NOS: 1, 3-8, and 10-14, wherein said isolated, synthetic, or recombinant polypeptide does not comprise human coagulation Factor V. In aspects, an isolated, synthetic, or recombinant polypeptide ($T_{reg}$ activating regulatory T-cell epitope, Tregitope, or T-cell epitope polypeptide) comprises one or more of SEQ ID NOS: 2 or 9, wherein said isolated, synthetic, or recombinant polypeptide does not comprise human coagulation Factor VIII. In aspects of above-described polypeptides, the polypeptides may be isolated, synthetic, or recombinant.

In aspects, the present disclosure is directed to a chimeric or fusion polypeptide composition (which in aspects may be isolated, synthetic, or recombinant) comprising one or more polypeptides ($T_{reg}$ activating regulatory T-cell epitope, Tregitope, or T-cell epitope polypeptide) of the present disclosure. In aspects, a chimeric or fusion polypeptide composition of the present disclosure comprises one or more polypeptides ($T_{reg}$ activating regulatory T-cell epitope, Tregitope, or T-cell epitope polypeptide) of the present disclosure joined to, linked to (e.g., fused in-frame, chemically-linked, or otherwise bound), and/or inserted into a heterologous polypeptide. In aspects, the one or more polypeptides ($T_{reg}$ activating regulatory T-cell epitope, Tregitope, or T-cell epitope polypeptide) of the present disclosure may be inserted into the heterologous polypeptide, may be added to the C-terminus, and/or added to the N-terminus of the heterologous polypeptide. In aspects of the above chimeric or fusion polypeptide compositions, the one or more polypeptides ($T_{reg}$ activating regulatory T-cell epitope, Tregitope, or T-cell epitope polypeptide) of the present disclosure have a sequence comprising, consisting of, or consisting essentially of one or more of SEQ ID NOS: 1-14. In aspects, the one or more isolated, synthetic, or recombinant polypeptides ($T_{reg}$ activating regulatory T-cell epitope, Tregitope, or T-cell epitope polypeptide) of the present disclosure comprises, consists of, or consists essentially of a sequence one or more of SEQ ID NOS: 1-2. In aspects, the one or more isolated, synthetic, or recombinant polypeptides ($T_{reg}$ activating regulatory T-cell epitope, Tregitope, or T-cell epitope polypeptide) of the present disclosure comprises, consists of, or consists essentially the amino acid sequence of SEQ ID NO: 1. In aspects of the chimeric or fusion polypeptide compositions, the one or more of SEQ ID NOS: 1-14 may be joined to, linked to (e.g., fused in-frame, chemically-linked, or otherwise bound), and/or inserted into a heterologous polypeptide as a whole, although it may be made up from a joined to, linked to (e.g., fused in-frame, chemically-linked, or otherwise bound), and/or inserted amino acid sequence, together with flanking amino acids of the heterologous polypeptide. In aspects, a chimeric or fusion polypeptide composition of the present disclosure comprises a polypeptide, said polypeptide having a sequence comprising one or more of SEQ ID NOS: 1-14 of the present disclosure, wherein said one or more of SEQ ID NOS: 1-14 is not naturally included in the polypeptide and/or said of one or more of SEQ ID NOS: 1-14 is not located at its natural position in the polypeptide. In aspects, the one or more of SEQ ID NOS: 1-14 of the present disclosure can be joined, linked to (e.g., fused in-frame, chemically-linked, or otherwise bound), and/or inserted into the polypeptide. In aspects of above-described chimeric or fusion polypeptide compositions, the chimeric or fusion polypeptides may be isolated, synthetic, or recombinant.

In aspects, the present disclosure is directed to a nucleic acid (e.g., DNA or RNA), which in aspects may be isolated, synthetic, or recombinant, encoding one or more polypeptides ($T_{reg}$ activating regulatory T-cell epitope, Tregitope, or T-cell epitope polypeptide) of the present disclosure or encoding chimeric or fusion polypeptide compositions of the present disclosure. In aspects of the nucleic acids encoding one or more polypeptides ($T_{reg}$ activating regulatory T-cell epitope, Tregitope, or T-cell epitope polypeptide) of the present disclosure or chimeric or fusion polypeptide compositions of the present disclosure, the one or more polypeptides or recombinant chimeric or fusion polypeptide compositions have a sequence comprising, consisting of, or consisting essentially of one or more of SEQ ID NOS: 1-14. In aspects of the nucleic acids encoding one or more polypeptides ($T_{reg}$ activating regulatory T-cell epitope, Tregitope, or T-cell epitope polypeptide) of the present disclosure or chimeric or fusion polypeptide compositions of the present disclosure, the one or more polypeptides or recombinant chimeric or fusion polypeptide compositions have a sequence comprising, consisting of, or consisting essentially of one or more of SEQ ID NOS: 1-2. In aspects of the nucleic acids encoding one or more polypeptides ($T_{reg}$ activating regulatory T-cell epitope, Tregitope, or T-cell epitope polypeptide) of the present disclosure or chimeric or fusion polypeptide compositions of the present disclosure, the one or more polypeptides or recombinant chimeric or fusion polypeptide compositions have a sequence comprising, consisting of, or consisting essentially of SEQ ID NO: 1. In aspects, a vector comprising a nucleic acid of the present disclosure encoding one or more polypeptides ($T_{reg}$ activating regulatory T-cell epitopes, Tregitopes, or T-cell epitope polypeptides) of the present disclosure or chimeric or fusion polypeptide composition of the present disclosure, e.g., but not limited to, a nucleic acid (e.g., DNA or RNA) encoding at least one regulatory T-cell epitope having a sequence comprising, consisting of, or consisting essentially of one or more of SEQ ID NOS: 1-14, is provided. In aspects, the present disclosure is directed to a cell comprising a vector of the present disclosure.

In aspects, the present disclosure is directed to a pharmaceutical composition or formulation comprising a Tregitope composition as disclosed herein (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; and/or chimeric or fusion polypeptide compositions as disclosed herein (which in aspects may be isolated, synthetic, or recombinant)). In aspects, the pharmaceutical composition further comprises a pharmaceutically-acceptable carrier and/or excipient. In aspects, the present disclosure is directed to a pharmaceutical composition or formulation comprising a Tregitope composition as disclosed herein (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; and/or chimeric or fusion polypeptide compositions as disclosed herein (which in aspects may be isolated, synthetic, or recombinant)), wherein the Tregitope composition (or the one or more Tregitope included in the Tregitope composition) comprises, consists of, or consists essentially of one or more of SEQ ID NOS: 1-14. In aspects of the pharmaceutical composition or formulation, the Tregitope composition (or the one or more Tregitope included in the Tregitope composition) comprises, consists of, or consists essentially of one or more of SEQ ID NOS: 1-2. In aspects of the pharmaceutical composition or formulation, the Tregitope composition (or the one or more Tregitope included in the Tregitope composition) comprises, consists of, or consists essentially of the amino acid sequence of SEQ ID NO: 1.

In aspects, the present disclosure is directed to a method of stimulating, inducing, and/or expanding regulatory T-cells (in aspects, naturally occurring $T_{Regs}$, including natural $T_{Regs}$ and/or adaptive $T_{Regs}$) in a subject in need thereof and/or suppressing an immune response in a subject in need thereof by administering to the subject a therapeutically effect amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein).

In aspects, the present disclosure is directed to a method of treating or preventing a medical condition in a subject in need thereof comprising administering a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein). In aspects, the medical condition is selected from the group consisting of: an allergy, an autoimmune disease, a transplant related disorder, graft versus host disease, a blood clotting disorder, an enzyme or protein deficiency disorder, a hemostatic disorder, cancer, infertility; and a viral, bacterial or parasitic infection. In another embodiment, the medical condition is hemophilia A, B, or C.

In aspects, the present disclosure is directed to a method of stimulating/inducing, regulatory T-cells (e.g., naturally occurring $T_{Regs}$ (in aspects, including natural $T_{Regs}$ and/or adaptive $T_{Regs}$)) to suppress an immune response in a subject in need thereof by administering to the subject a therapeutically effect amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein). In aspects, the immune response is the result of one or more therapeutic treatments with at least one therapeutic protein, treatment with a vaccine or treatment with at least one antigen. In a particular embodiment, the immune response is the result of one or more therapeutic treatments with a Coagulation Factor VIII supplement. Thus, the administration of one or more Tregitope compositions of the present disclosure can be used to prevent the development of, or terminate, an already-established immune response to establish tolerance induction to Factor VIII (and Coagulation Factor VIII supplements) in patients suffering from Hemophilia A. In another aspect, the administration of a Tregitope composition of the present disclosure shifts one or more antigen presenting cells to a regulatory phenotype, one or more dendritic cells to a regulatory phenotype, decreases CD11c and HLA-DR expression in the dendritic cells or other antigen presenting cells.

In aspects, the present disclosure is directed to a method for expanding a population of regulatory T cells, comprising: (a) providing a biological sample from a subject; and (b) isolating regulatory T-cells from the biological sample; (c) contacting the isolated regulatory T-cells with an effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), under conditions wherein the T-regulatory cells increase in number to yield an expanded regulatory T-cell composition, thereby expanding the regulatory T-cells in the biological sample; and, additionally, (d) returning the sample to the patient in need of treatment.

In aspects, the present disclosure is directed to a method for stimulating regulatory T cells in a biological sample, comprising: (a) providing a biological sample from a subject; (b) isolating regulatory T-cells from the biological sample; (c) contacting the isolated regulatory T-cells with an effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), under conditions wherein the T-regulatory cells are stimulated to alter one or more biological function, thereby stimulating the regulatory T-cells in the biological sample; and, additionally, (d) returning cells to the patient in need of treatment.

In aspects, the present disclosure is directed to a method for repressing/suppressing an immune response in a subject, comprising administering a therapeutically effective amount of Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), wherein the Tregitope composition represses/suppresses the immune response. In aspects, the Tregitope composition represses/suppresses an innate immune response. In aspects, the Tregitope composition represses/suppresses an adaptive immune response. In aspects, the Tregitope composition represses/suppresses an effector T cell response. In aspects, the Tregitope composition represses/suppresses a memory T cell response. In aspects, the Tregitope composition represses/suppresses helper T cell response. In aspects, the Tregitope composition represses/suppresses B cell response. In aspects, the Tregitope composition represses/suppresses a nkT cell response.

In aspects, the present disclosure is directed to a method of suppressing an immune response, specifically an antigen specific immune response in a subject, through the administration of a therapeutically effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), wherein said Tregitope composition activates naturally occurring $T_{Regs}$ (in aspects, including natural $T_{Regs}$ and/or adaptive $T_{Regs}$, and in aspects CD4$^+$/CD25$^+$/FoxP3$^+$ regulatory T-cells) or suppresses the activation of CD4$^+$ T-cells, the proliferation of CD4$^+$ and/or CD8$^+$ T-cells, and/or suppresses the activation or proliferation of β-cells or nkT Cells. In aspects, a Tregitope composition of the present disclosure may be either covalently bound, non-covalently bound, or in admixture with a specific target antigen. In aspects, an administered Tregitope composition of the present disclosure that is covalently bound, non-covalently bound, or in admixture with a specific target antigen results in the diminution of immune response against the target antigen.

In aspects, the target antigen may be an autologous protein or protein fragment. In aspects, the target antigen may be an allergen. In aspects, the target antigen may allogenic protein or protein fragments. In aspects, the target antigen may be a biologic medicine or fragments thereof. In aspects, the target antigen is a Coagulation Factor VIII supplement. In aspects, the suppressive effect is mediated by natural $T_{Regs}$. In aspects, the suppressive effect is mediated by adaptive $T_{Regs}$. In aspects, the one or more Tregitope included in the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) suppresses an effector T cell response. In aspects, the one or more Tregitopes of the presently-disclosed Tregitope compositions suppresses an innate immune response. In aspects, the one or more Tregitopes of the presently-disclosed Tregitope compositions suppresses an adaptive immune response. In aspects, the one or more Tregitopes of the presently-disclosed Tregitope compositions suppresses helper T cell response. In aspects, the one or more Tregitopes of the presently-disclosed Tregitope compositions suppresses a memory T cell response. In aspects, the one or more Tregitopes of the presently-disclosed Tregitope compositions suppresses B cell response. In aspects, the one or more Tregitopes of the presently-disclosed Tregitope compositions suppresses nkT cell response.

In aspects, the present disclosure is directed to a kit for preventing or treating a medical condition, in particular, for the suppression of an immune response in a subject, wherein the kit comprises a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein). In aspects, the kit may further comprise an effective amount of an antigen or allergen or therapeutic agent, such as a replacement protein or peptide.

BRIEF DESCRIPTION OF THE DRAWINGS

The present disclosure may be better understood with reference to the following figures.

FIGS. 1A-E are a series of graphs reporting HLA DRB1 competition binding curves. In particular, FIG. 1A summarizes the results for HLA DRB1 *0101 assay (left panel shows SEQ ID NOS: 1, 3, 4, and 6, right panel shows SEQ ID NOS: 5 and 7), FIG. 1B summarizes the results for the HLA DRB1 *0301 assay. FIG. 1C summarizes the results for the HLA DRB1 *0701 assay for the selected FV peptides (left panel shows SEQ ID NOS: 1, 3, 4, and 6, right panel shows SEQ ID NOS: 5 and 7), FIG. 1D summarizes the results for HLA DRB1 *1101 assay for selected FV peptides (left panel shows SEQ ID NOS: 1, 3, 4, and 6, right panel shows SEQ ID NOS: 5 and 7), and FIG. 1E report summarizes the results for HLA DRB1* 1501 (left panel shows SEQ ID NOS: 1, 3, 4, and 6, right panel shows SEQ ID NOS: 5 and 7).

FIGS. 2A-C demonstrates the effects of exposure to putative Tregitopes on the phenotypes of dendritic cells. FIG. 2A depicts an overlay of HLA-DR/CD11c dot plots for SEQ ID NO: 15 (dark gray, which is described in the figure as 167) and media control (light gray) highlights the shift in observed HLA-DR expression. FIG. 2B is the equation used to calculate % Δ in HLA-DR MFI where % is relative to media control. FIG. 2C is a bar graph showing the % Δ in HLA-DR MFI for each peptide stimulant (wherein SEQ ID NO: 15 is Treg 167).

FIGS. 3A-C depicts the % Δ change in the HLA negative population calculated for each peptide stimulant relative to the media control. In particular, FIG. 3A is a plot of HLA-DR versus CD11c for SEQ ID NO: 15 (which is described in the figure as Tregitope 167) and the media control. FIG. 3B is a bar graph that plots the % of HLA+ and HLA- each peptide stimulant where the vehicle is media. $T_{Reg}$ 167 was used as a control and has the sequence PAVLQSSGLYSLSLSSVVTVPSSSLGTQ (SEQ ID NO: 15). FIG. 3C is the equation used to calculate the % Δ change in the HLA negative population.

FIGS. 6A-B depict the gating strategy for highly activated regulatory T cells. CD4+ Tcells are gated for elevated CD25, Ganzyme B, Foxp3, and low CFSE (proliferation). FIG. 6A shows the gating strategy on the assay with no addition of Tetanus Toxoid (TT), while FIG. 6B shows the gating strategy on the assay with the addition of 0.5 μg/mL of TT.

FIG. 8A demonstrates that activated T effector cells ($T_{eff}$) are characterized by CD25 and FoxP3 where activated $T_{eff}$ are $CD25^{hi}/FoxP3^{int}$ population, while FIG. 8B shows proliferation of characterized CD4 T cells where cells are first gated on CD4+ and percent proliferation of the CD4+/CD25+ T cells is determined by the CFSE depletion.

FIG. 12 aligns the Tregitopes (SEQ ID NO: 8 (start peptide) and SEQ ID NO: 1 (extended peptide)) with its Factor VIII homologues (SEQ ID NO: 9 (start peptide) and SEQ ID NO 2 (extended peptide), respectively), displaying the homology between the peptides. Anchor residues are shown as bolded; conserved TCR contacts are shown as bolded and underlined; and mismatched TCR contacts are shown as bolded and italicized.

FIG. 19 depicts an example of an immunogenic influenza HA peptide that contains an EpiBar and the EpiMartix analysis of the promiscuous influenza epitope. The influenza HA peptide scores extremely high for all eight alleles in EpiMatrix and has a cluster score of 18. Cluster scores of 10 are considered significant. The band-like EpiBar pattern is characteristic of promiscuous epitopes. Results are shown for PRYVKQNTL (SEQ ID NO: 60), RYVKQNTLK (SEQ ID NO: 61), YVKQNTLKL (SEQ ID NO: 62), VKQNTLKLA (SEQ ID NO: 63) and KQNTLKLAT (SEQ ID NO: 64). Z score indicates the potential of a 9-mer frame to bind to a given HLA allele. All scores in the top 5% are considered "hits", while non hits (*) below 10% are masked in FIG. 19 for simplicity.

FIG. 20 shows putative epitopes shared between Human Factor V and Human Factor VIII, with >80% TCR contacts preserved (matched on DR15), as well as their EpiMatrix Score. Anchor residues are shown in black, conserved TCR contacts are shown in green, and mis-matched TCR contacts are shown in red. Results are shown for: IHFTGHSFI (SEQ ID NO: 8) and extended peptide ILTIHFTGHSFIYGK (SEQ ID NO: 1), selected; IHFSGHVFT (SEQ ID NO: 9) and extended peptide IHSIHFSGHVFTVRK (SEQ ID NO: 2), selected; FKNMASRPY (SEQ ID NO: 10) and extended peptide KIVFKNMASRPYSIY (SEQ ID NO: 3), selected; IMSTINGYV (SEQ ID NO: 12) and extended peptide ESNIMSTINGYVPES (SEQ ID NO: 5), selected; FHAINGMIY (SEQ ID NO: 14) and extended peptide SHEFHAINGMIYSLP (SEQ ID NO: 7), selected; IEDFNSGLI (SEQ ID NO: 16) and extended peptide ENLIEDFNSGLIGPL (SEQ ID NO: 17); VKDLNSGLI (SEQ ID NO: 18) and extended peptide VDLVKDLNSGLIGAL (SEQ ID NO: 19); KIVFKNMAS (SEQ ID NO: 20) and extended peptide DTLKIVFKNMASRPY (SEQ ID NO: 21); VITLKNMAS (SEQ ID NO: 22) and extended peptide DTVVITLKNMASHPV (SEQ ID NO: 23); FKNQASRPY (SEQ ID NO: 24) and extended peptide LTIFKNQASRPYNIY (SEQ ID NO: 25); LKNMASHPV (SEQ ID NO: 26) and extended peptide VITLKNMASHPVSLH (SEQ ID NO: 27); FRNQASRPY (SEQ ID NO: 28) and extended peptide MVTFRNQASRPYSFY (SEQ ID NO: 29); IMHSINGYV (SEQ ID NO: 30) and extended peptide ASNIMSSINGYVFDS (SEQ ID NO: 31); LLLKQSNSS (SEQ ID NO: 32) and extended peptide SDLLLLKQSNSSKIL (SEQ ID NO: 33); RVLFQDNSS (SEQ ID NO: 34) and extended peptide YLTRVLFQDNSSHLP (SEQ ID NO: 35); FKNLASRPY (SEQ ID NO: 36) and extended peptide QVRFKNLASRPYSLH (SEQ ID NO: 37); LKNMASHPV (SEQ ID NO: 38) and extended peptide VITLKNMASHPVSLH (SEQ ID NO: 39); FKNQASRPY (SEQ ID NO: 40) and extended peptide LIIFKNQASRPYNIY (SEQ ID NO: 41); FRNQASRPY (SEQ ID NO: 42) and extended peptide MVTFRNQASRPYSFY (SEQ ID NO: 43); FHAINGYIM (SEQ ID NO: 44) and extended peptide NYRFHAINGYIMDTL (SEQ ID NO: 45); IKKITAIIT (SEQ ID NO: 46) and extended peptide LLKIKKITAIITQGC (SEQ ID NO: 47); FKKVTPLIH (SEQ ID NO: 48) and extended peptide DTEFKKVTPLIHDRM (SEQ ID NO: 49); VKNFFNPPI (SEQ ID NO: 50) and extended peptide KGHVKNFFNPPIISR (SEQ ID NO: 51); and KHNIFNPPI (SEQ ID NO: 52) and extended peptide SGIKHNIFNPPIIAR (SEQ ID NO: 53).

FIG. 21 shows putative epitopes in which Human Factor V and Human Factor VIII peptide pairs matched at all five TCR contact positions and their putative EpiMatrix scores. Anchor residues are shown in black, conserved TCR contacts are shown in green, and mis-matched TCR contacts are shown in red. Results are shown for: FDENLSWYL (SEQ ID NO: 11) and extended peptide FAVFDENKSWYLEDN (SEQ ID NO: 4); IHSGLIGPL (SEQ ID NO: 13) and extended peptide EKDIHSGLIGPLLI (SEQ ID NO: 6); FDETKSWYF (SEQ ID NO: 54) and extended peptide FTIFDETKSWYFTEN (SEQ ID NO: 55); FDENRSWYL (SEQ ID NO: 56) and extended peptide FSVFDENR- SWYLTEN (SEQ ID NO: 57); and VHSGLIGPL (SEQ ID NO: 58) and extended peptide EKDVHSGLIGPLIV (SEQ ID NO: 59).

FIG. 22 summarizes the results obtained through the dendritic cells phenotyping assays of FIG. 5. As presented in FIG. 22, exposure to claimed Tregitope SEQ ID NO: 1, decreased expression of HLA-DR in all five subjects tested. Further, in four out of five subjects, exposure to Tregitope SEQ ID NO: 1 increased the percent of CD86-low present among the CD11c-high cohort. Both trends indicated a shift towards an acquired regulatory phenotype. The analyses of the ΔMFI and % cell population calculations are relative to vehicle control analysis.

FIG. 24A shows the response to TT by donor 108 in typifies a trend observed across donors and shows typical distinct populations. FIG. 24B shows the gating strategy for the FoxP3 and CD25 markers showing degree of proliferation for each population. FIG. 24C shows the regulatory phenotype of total CD4 T cells and proliferating CD4 T cells showing the high preponderance of activated effector T cells in the latter. FIG. 24D shows that most of the activated T cells (CD25$^{hi}$ FoxP3$^{int}$, Q2) show an effector memory phenotype (CD45RA-low/CCR7-low).

FIG. 25 is summary of HLA binding results for the binding curves for certain Tregitopes against the selected Class II HLA alleles as shown in FIGS. 1A-C.

DETAILED DESCRIPTION OF THE INVENTION

General

Figure 1C:
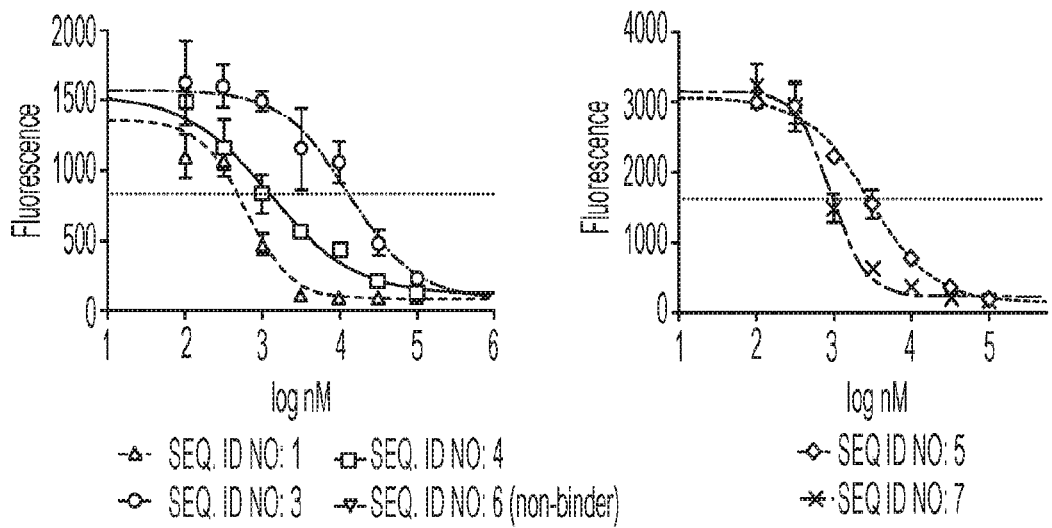

The adaptive immune cascade begins when soluble protein antigens are taken up by Antigen Presenting Cells (APCs) and processed through the Class II antigen presentation pathway. Protein antigens in the Class II presentation pathway are degraded by various proteases found in the Endoplasmic Reticulum. Some of the resulting protein fragments are bound to Class II MHC molecules. Peptide-loaded MHC molecules are trafficked to the cell surface where they are interrogated by CD4+ T cells. Peptide fragments that are capable of binding to an MHC molecule and mediating the cell to cell interaction between APC and circulating T cells are referred to as T cell epitopes. Recognition of these peptide-MHC complexes by CD4+ T cells can lead to either an immune activating or immune suppressive response based on the phenotype of the responding T cells and the local cytokine/chemokine milieu. In general, engagement between the MHC/peptide complex and the T cell receptor (TCR) of T effector cells leads to activation and the subsequent secretion of pro-inflammatory cytokines such as IL-4, and IFN-γ. On the other hand, the activation of natural T regulatory cells ($T_{Regs}$) leads to the expression of the immune suppressive cytokines IL-10 and TGF-6, among others (Shevach E, (2002), Nat Rev Immunol, 2(6):389-400). These cytokines act directly on nearby effector T cells leading in some cases to anergy or apoptosis. In other cases, regulatory cytokines and chemokines convert effector T cells to T regulatory phenotypes; this process is referred here as "induced" or "adaptive" tolerance. T cell epitopes that are capable of binding to MHC molecules and engaging and/or activating circulating naturally occurring $T_{Regs}$ (in aspects, including natural $T_{Regs}$ and/or adaptive $T_{Regs}$), are referred to as Tregitopes. In aspects, the instantly-disclosed Tregitopes are T cell epitope clusters, which are epitopes capable of binding to multiple MHC alleles and multiple TCRs.

Initial self/non-self discrimination occurs in the thymus during neonatal development where cortical and medullary epithelial cells express specific self-protein epitopes to immature T cells. T cells recognizing self-antigens with high affinity are deleted, but autoreactive T cells with moderate affinity sometimes avoid deletion and can be converted to so called natural regulatory T cells ($T_{Reg}$) cells. These natural $T_{Reg}$ cells are exported to the periphery and help to control a latent autoimmune response. Natural regulatory T cells are a critical component of immune regulation and self-tolerance.

Self-tolerance is regulated by a complex interplay between T cells, B cells, cytokines and surface receptors. T regulatory immune responses counterbalance T effector immune response to protein antigens (whether self or foreign). A tilt of the balance toward the autoreactive side, either by increasing the number or function of autoreactive T effector cells or by diminishing the number or function of T regulatory cells, is manifested as autoimmunity.

A second form of tolerance occurs in the periphery where mature T cells are converted to an 'adaptive' $T_{Reg}$ phenotype upon activation via their T cell receptor in the presence of IL-10 and TGF-β, usually supplied by bystander T regulatory cells. The possible roles for these 'adaptive' $T_{Reg}$ cells include dampening immune response following the successful clearance of an invading pathogen, controlling excessive inflammation caused by an allergic reaction, controlling excessive inflammation caused by low level or chronic infection, or possibly controlling inflammatory response targeting beneficial symbiotic bacteria and viruses. 'Adaptive' $T_{Reg}$ may also play a role in suppressing immune response targeting human antibodies that have undergone somatic hypermutation (Chaudhry A et al., (2011), Immunity, 34(4):566-78).

$T_{Reg}$ cells are also instrumental in B cell tolerance. B cells express a single low affinity Fc receptor, FcγRIIB on their cell surface (Ravetch JV et al., (1986), Science, 234(4777): 718-25). This receptor contains the immunoreceptor tyrosine-based inhibition motif sequence (ITIM) in its cytoplasmic domain. Co-ligation of FcγRIIB and the B-cell receptor (BCR) by immune complexes act to trigger the tyrosine phosphorylation of the ITIM leading to the recruitment of the inositol phosphatase, SHIP, which inhibits BCR-triggered proliferation by interfering with the activation of MAP kinases and blocks phagocytosis by the dissociation of Burton's tyrosine kinase (Btk) from the cell membrane, which inhibits calcium influx into the cell. FcγRIIB can also induce apoptosis independent of the ITIM. Upon homo-aggregation of FcγRllB by ICs, the association of Btk with the cell membrane is enhanced, thereby triggering an apoptotic response (Pearse R, et al., (1999), Immunity, 10(6): 753-60). Expression of FcγRIIB is highly variable and cytokine dependent. IL-4 and IL-10, which are expressed by activated Th2 and $T_{Reg}$ cells, have been shown to act synergistically to enhance FcγRIIB expression (Joshi T et al., (2006), Mol Immuno., 43(7):839-50), thus aiding in the suppression of a humoral response.

It is possible to exploit Tregitope specific $T_{Reg}$ cells to suppress unwanted immune responses and also to induce adaptive $T_{Reg}$ to co-delivered proteins. This discovery has implications for the design of therapeutic regimens and antigen-specific therapies for transplantation, protein therapeutics, allergy, chronic infection, autoimmunity and vaccine design. Administration of a drug, a protein, or an allergen in conjunction with Tregitopes, including a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can suppress an effector immune response. Tregitopes, including Tregitope compositions of the present disclosure, can be used to deliberately manipulate the immune system toward tolerance.

The Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) are useful in the selective engagement and activation of regulatory T cells. It is demonstrated herein that certain naturally occurring $T_{Regs}$ (in aspects, including natural $T_{Regs}$ and/or adaptive $T_{Regs}$), can be engaged, activated, and/or applied to the suppression of unwanted immune responses in both systemic and limited, disease specific, contexts. In aspects, the Tregitope compositions of the present disclosure can be used to engage and activate pre-existing populations of regulatory T cells to suppress an immune response caused by Factor VIII supplements that are used to prevent or stop bleeding in patients suffering from Hemophilia A Despite extensive efforts, with few exceptions, the antigen specificity of natural $T_{Regs}$, and more importantly natural $T_{Regs}$ circulating in clinically significant volumes, is unknown. Presented herein is a demonstration that certain human proteins circulating in the blood steam, such as immunoglobulins or the serum proteins coagulation Factor V ("FV") and coagulation Factor VIII ("FVIII"), contain T cell epitopes that relate to naturally occurring populations of regulatory T cells (in aspects, including natural $T_{Regs}$ and/or adaptive $T_{Regs}$). In the course of normal immune surveillance, these proteins are taken up by professional APCs, such as dendritic cells or macrophages, and degraded. During the degradation process, some of the epitopes contained in these proteins are bound to MHC molecules, transported to the cell surface presented to regulatory T cells. Those cells, once activated by the APC, release cytokines and chemokines help to suppress autoimmune responses that would otherwise hinder the function of the extra cellular proteins.

By using the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) to selectively activate naturally occurring $T_{Regs}$ (in aspects, including natural $T_{Regs}$ and/or adaptive $T_{Regs}$), it is herein shown that the Tregitope compositions of the present disclosure can be used to suppress a variety of unwanted immune responses. In its simplest form, systemic application of the Tregitope compositions of the present disclosure can be used as a generalized immune suppressant useful for controlling severe autoimmune reactions such as, for example, MS flare-ups, allergic reactions, transplant reactions, or uncontrolled response to infection.

In a more controlled application, for example but not limited to, topically applied to joints affected by rheumatoid arthritis (RA), the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can be used to suppress localized autoimmune responses. In a targeted application, such as might be achieved through the fusion, bonding or admixture of the Tregitope compositions of the present disclosure to certain other T cell epitopes, the Tregitope compositions can suppress highly specific immune reactions to the fused, bonded, or admixed T cell epitopes while leaving the balance of the immune system intact. For example, through the delivery of a Tregitope composition of the present disclosure fused to an autoimmune antigen such as insulin, an allergen such as Brazil nut antigen, or an antigenic protein such as an antibody (which can be IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody) or replacement enzyme, the immune system can be trained to "tolerate" the co-delivered antigen by, e.g., inducing naturally occurring $T_{Regs}$ (in aspects, including natural $T_{Regs}$ and/or adaptive $T_{Regs}$) and/or converting the phenotype of responding effector T cells to that of adaptive regulatory T cells.

In certain aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can be used to suppress an immune response caused by Factor VIII supplements that are used to prevent or stop bleeding in patients suffering from Hemophilia A. For example, Factor VIII supplements can be administered with the Tregitope compositions of the present disclosure (e.g. but not limited to, through fusion, bonding, or admixture of the Factor VIII supplement(s) with the Tregitope compositions of the present disclosure, or insertion and/or linkage of the Tregitope(s) of the invention into the Factor VIII supplement(s)), with the Tregitope compositions of the present disclosure suppressing an immune response targeting the Factor VIII supplement(s). Such immune reprogramming could reduce or eliminate immune response targeting the Factor VIII supplements used to prevent or stop bleeding in patients suffering from Hemophilia A, while leaving the balance of the immune system intact.

As stated above, the Tregitopes of the present disclosure are derived from circulating extracellular proteins. To be useful, these Tregitopes should be true T cell epitopes (i.e., capable of binding to both MHC molecules and TCRs). In aspects, the Tregitopes should be related to a pre-existing population of regulatory T cells that is sufficiently large to have a therapeutic effect. T cell epitope clusters, which are epitopes capable of binding to multiple MHC alleles and multiple TCRs, are key to satisfying this latter qualification.

More particularly, the Tregitopes of the present disclosure are components of coagulation Factor V or Factor VIII. In their natural state, the Tregitopes of the present disclosure are capable of engaging and activating naturally occurring $T_{Regs}$ (in aspects, including natural $T_{Regs}$ and/or adaptive $T_{Regs}$) which prevent or terminate immune responses. These coagulation Factor V or VIII peptides are highly related to fragments of coagulation Factor VIII. In aspects, exposure of patients with Hemophilia A to the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can prevent an immune response to coagulation Factor VIII allowing treated patients the full benefit of Factor VIII supplements. Additionally, treatment with Tregitope compositions of the present disclosure can expand corresponding naturally occurring $T_{Reg}$ populations (in aspects, including natural $T_{Regs}$ and/or adaptive $T_{Regs}$), making them available to be activated by homologous peptides derived from Factor VIII, thereby suppressing effector response targeting Factor VIII. The instantly-disclosed treatments provides the following advantages:

1. Treatment with the Tregitope compositions of the present disclosure is highly antigen specific (e.g., treatment with the Tregitope compositions can, e.g., expand and/or stimulate corresponding naturally occurring $T_{Reg}$ populations (in aspects, including natural $T_{Regs}$ and/or adaptive $T_{Regs}$) in a highly antigen specific manner);

2. An efficient and less expensive treatment regimen when compared to current antigen specific therapies wherein patients are treated over a prolonged period of time with frequent high dose Factor VIII infusions; and 3. A second line of defense treatment when high dose Factor VIII treatment fails to induce immune tolerance in the treated patient.

In aspects, the present disclosure is directed to therapeutic Tregitope compositions (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) that are safely administered to a patient experiencing an autoimmune response. The mechanism of action of the claimed Tregitopes (and Tregitopes within said Tregitope compositions) is natural, supporting their efficacy and safety. In aspects, the present disclosure is directed to therapeutic Tregitope compositions that are safely administered to a Hemophiliac A patient in need of treatment, given that the Tregitopes of the instant disclosure are natural components of coagulation Factor V and Factor VIII, and as such, are naturally present in all humans.

In aspects, the present is directed to Tregitope compositions (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) that include one or more of the following regulatory Tregitopes, fragments thereof, variants thereof, and fragments of such variants that retain MHC binding propensity and TCR specificity:

(SEQ ID NO: 1)
ILTIHFTGHSFIYGK;

(SEQ ID NO: 2)
IHSIHFSGHVFTVRK;

(SEQ ID NO: 3)
KIVFKNMASRPYSIY;

(SEQ ID NO: 4)
FAVFDENKSWYLEDN;

```
                                        (SEQ ID NO: 5)
ESNIMSTINGYVPES;

(SEQ ID NO: 6)
EKDIHSGLIGPLLI;

(SEQ ID NO: 7)
SHEFHAINGMIYSLP;

(SEQ ID NO: 8)
IHFTGHSFI;

(SEQ ID NO: 9)
IHFSGHVFT;

(SEQ ID NO: 10)
FKNMASRPY;

(SEQ ID NO: 11)
FDENLSWYL;

(SEQ ID NO: 12)
IMSTINGYV;

(SEQ ID NO: 13)
IHSGLIGPL;
and (SEQ ID NO: 14)
FHAINGMIY.
```

Definitions

To further facilitate an understanding of the present invention, a number of terms and phrases are defined below. Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "biological sample" as refers to any sample of tissue, cells, or secretions from an organism.

As used herein, the term "transplantation" refers to the process of taking a cell, tissue, or organ, called a "transplant" or "graft" from one subject and placing it or them into a (usually) different subject. The subject who provides the transplant is called the "donor", and the subject who received the transplant is called the "recipient". An organ or graft transplanted between two genetically different subjects of the same species is called an "allograft". A graft transplanted between subjects of different species is called a "xenograft".

As used herein, the term "medical condition" includes, but is not limited to, any condition or disease manifested as one or more physical and/or psychological symptoms for which treatment and/or prevention is desirable, and includes previously and newly identified diseases and other disorders.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, malignant melanoma, invading pathogens, cells or tissues infected with pathogens, or, in cases of autoimmunity or pathological inflammation, normal human cells or tissues.

As used herein, the term "effective amount", "therapeutically effective amount", or the like of a composition, including Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) is a quantity sufficient to achieve a desired therapeutic and/or prophylactic effect, e.g., an amount that results in the prevention of, or a decrease in, the symptoms associated with a disease that is being treated. The amount of a composition of the present disclosure administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with each other or with one or more additional therapeutic compounds.

As used herein, the term "regulatory T cell", "$T_{reg}$", or the like, means a subset of naturally occurring T cells (in aspects, including natural $T_{Regs}$ and/or adaptive $T_{Regs}$) characterized by the presence of certain cell surface markers including but not limited to CD4, CD25, and FoxP3. Upon activation, regulatory T cells secrete immune suppressive cytokines and chemokines including but not limited to IL-10, TGF-β and TNF-α.

As used herein, the term "T cell epitope" means an MHC ligand or protein determinant, 7 to 30 amino acids in length, and capable of specific binding to human leukocyte antigen (HLA) molecules and interacting with specific T cell receptors (TCRs). Generally, T cell epitopes are linear and do not express specific three-dimensional characteristics. T cell epitopes are not affected by the presence of denaturing solvents. The ability to interact with T cell epitopes can be predicted by in silico methods (De Groot A S et al., (1997), AIDS Res Hum Retroviruses, 13(7):539-41; Schafer J R et al., (1998), Vaccine, 16(19):1880-4; De Groot A S et al., (2001), Vaccine, 19(31):4385-95; De Groot A R et al., (2003), Vaccine, 21(27-30):4486-504, all of which are herein incorporated by reference in their entirety).

As used herein, the term "T-cell epitope cluster" refers to polypeptide that contains between about 4 to about 40 MHC binding motifs. In particular embodiments, the T-cell epitope cluster contains between about 5 to about 35 MHC binding motifs, between about 8 and about 30 MHC binding motifs, or between about 10 and 20 MHC binding motifs.

The term "regulatory T cell epitope" ("Tregitope") refers to a "T cell epitope" that causes a tolerogenic response (Weber Calif. et al., (2009), Adv Drug Deliv, 61(11):965-76) and is capable of binding to MHC molecules and engaging and/or activating circulating naturally occurring $T_{Regs}$ (in aspects, including natural $T_{Regs}$ and/or adaptive $T_{Regs}$), leading to the expression of the immune suppressive cytokines including, but not limited to, IL-10 and TGF-β and TNF-α. In aspects, the instantly disclosed Tregitopes are T cell epitope clusters, which are epitopes capable of binding to multiple MHC alleles and multiple TCRs.

As used herein, the term "immune stimulating T-cell epitope polypeptide" refers to a molecule capable of inducing an immune response, e.g., e.g., a humoral, T cell-based, or innate immune response. In aspects, an immune stimulating T-cell epitope polypeptide is human Coagulation Factor V or Coagulation Factor VIII.

As used herein, the term "B cell epitope" means a protein determinant capable of specific binding to an antibody. B cell epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "MHC complex" refers to a protein complex capable of binding with a specific repertoire of polypeptides known as HLA ligands and transporting said ligands to the cell surface.

As used herein, the term "MHC Ligand" means a polypeptide capable of binding to one or more specific MHC alleles. The term "HLA ligand" is interchangeable with the term "MHC Ligand". Cells expressing MHC/Ligand complexes on their surface are referred to as "Antigen Presenting Cells" (APCs).

As used herein, the term "T Cell Receptor" or "TCR" refers to a protein complex expressed by T cells that is capable of engaging a specific repertoire of MHC/Ligand complexes as presented on the surface of APCs.

As used herein, the term "MHC Binding Motif" refers to a pattern of amino acids in a protein sequence that predicts binding to a particular MHC allele.

As used herein, the term "EpiBar™" refers to a single 9-mer frame that is predicted to bind to at least four different HLA alleles. A representative example of an immunogenic peptide that contains an EpiBar™ is shown below in FIG. 19. FIG. 19 depicts an example of an EpiBar and the EpiMatrix analysis of a pormiscous influenza epitope. Consider the influenza HA peptide, an epitope known to be promiscuously immunogenic. It scores extremely high for all eight alleles in EpiMatrix. Its cluster score is 18. Cluster scores higher than 10 are considered to be significant. The band-like EpiBar pattern is characteristic of promiscuous epitopes. Results are shown in FIG. 19 for PRYVKQNTL (SEQ ID NO: 60), RYVKQNTLK (SEQ ID NO: 61), YVKQNTLKL (SEQ ID NO: 62), VKQNTLKLA (SEQ ID NO: 63) and KQNTLKLAT (SEQ ID NO: 64). Z score indicates the potential of a 9-mer frame to bind to a given HLA allele. All scores in the top 5% are considered "hits", while non hits (*) beow 10% are masked in FIG. 19 for simplicity.

As used herein, the term "Immune Synapse" means the protein complex formed by the simultaneous engagement of a given T cell epitope to both a cell surface MHC complex and TCR.

The term "polypeptide" refers to a polymer of amino acids, and not to a specific length; thus, peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide (e.g., a polypeptide comprising, consisting of, or consisting essentially of one or more of SEQ ID NOS: 1-14 or variants and fragments thereof, which in aspects may be isolated, synthetic, or recombinant) of the present disclosure, however, can be joined to, linked to, or inserted into another polypeptide (e.g., a heterologous polypeptide) with which it is not normally associated in a cell and still be "isolated" or "purified." As used herein with respect to the one or more Tregitopes of the instant disclosure, the term "heterologous polypeptide" is intended to mean that the one or more Tregitopes is heterologous to, or not included naturally, in the heterologous polypeptide. For example, one or more Tregitopes of the present disclosure (and/or one or more other Tregitopes, such as an IgG derived Tregitope as disclosed in U.S. Pat. No. 7,884,184, which is incorporated by reference in its entirety) can be linked to (e.g., fused in-frame, chemically-linked, or otherwise bound) and/or inserted into a heterologous polypeptide (e.g., a heterologous monoclonal antibody). Additionally, one or more Tregitopes of the present disclosure can be joined to, linked to, or inserted into another polypeptide wherein said one or more Tregitopes of the present disclosure is not naturally included in the polypeptide and/or said one or more Tregitopes of the present disclosure is not located at its natural position in the polypeptide. When a polypeptide is recombinantly produced, it can also be substantially free of culture medium, for example, culture medium represents less than about 20%, less than about 10%, or less than about 5% of the volume of the polypeptide preparation.

As used herein, the term "purpose built computer program" refers to a computer program designed to fulfill a specific purpose; typically to analyze a specific set of raw data and answer a specific scientific question.

As used herein, the term "z-score" indicates how many standard deviations an element is from the mean. A z-score can be calculated from the following formula. $z=(X-\mu)/\sigma$ where z is the z-score, X is the value of the element, p is the population mean, and $\sigma$ is the standard deviation.

As used herein, the singular forms "a," "an," and "the" are intended to include the plural forms, including "at least one," unless the content clearly indicates otherwise. "Or" means "and/or." As used herein, the term "and/or" and "one or more" includes any and all combinations of the associated listed items. For example, the term "one or more" with respect to the "one or more of SEQ ID NOS: 1-14 of the present disclosure" includes any and all combinations of SEQ ID NOS: 1-14. The term "or a combination thereof" means a combination including at least one of the foregoing elements.

The following abbreviations and/or acronyms are used throughout this application:
APC antigen presenting cells
CEF cytomegalovirus, Epstein-Barr virus and influenza virus
CFSE dye carboxyfluorescein succinimidyl ester dye
DMSO dimethyl sulfoxide
DR antibody antigen D related antibody
ELISA enzyme-linked immunosorbent assay
FACS fluorescence-activated cell sortings Fmoc 9-fluoronyl methoxy carbonyl
FV human coagulation Factor V
FVIII human coagulation Factor VIII
HLA human leukocyte antigen
HPLC high-performance liquid chromatography
IVIG intravenous purified Immunoglobulin G antibody
MFI mean fluorescence index
MHC major histocompatibility complex
PBMC peripheral blood mononuclear cell
PI proliferation index
RPMI Roswell Park Memorial Institute medium
$T_{eff}$ effector T cell
$T_{Reg}$ regulatory T cell
TT tetanus toxoid
UV ultraviolet A variant polypeptide (including a variant Tregitope) can differ in amino acid sequence by one or more substitutions, deletions, insertions, inversions, fusions, and truncations or a combination of any of these. In aspects, a variant Tregitope can differ in amino acid sequence by one or more substitutions, deletions, insertions, inversions, fusions, and truncations or a combination of any of these, provided said variants retain MHC binding propensity and TCR specificity.

The present disclosure also includes polypeptide fragments of the Tregitopes of the invention. The invention also encompasses fragments of the variants of the Tregitopes described herein, provided said fragments and/or variants retain MHC binding propensity and TCR specificity.

The present disclosure also provides chimeric or fusion polypeptides (which in aspects may be isolated, synthetic, or recombinant) wherein one or more of the instantly-disclosed Tregitopes is a part thereof. In aspects, a chimeric or fusion polypeptide composition comprises one or more polypeptides ($T_{reg}$ activating regulatory T-cell epitope, Tregitope, or T-cell epitope polypeptide) of the instant disclosure linked to a heterologous polypeptide (e.g. but not limited to, IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody)). As previously stated, the term "heterologous polypeptide" is intended to mean that the one or more Tregitope (e.g., one or more of SEQ ID NOS: 1-14) are heterologous to, or not included naturally, in the heterologous polypeptide. In aspects, the one or more Tregitope may be inserted into the heterologous polypeptide (e.g., through mutagenesis techniques or other known means in the art), may be added to the C-terminus, and/or added to the N-terminus of the heterologous polypeptide. For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety). In aspects, chimeric or fusion polypeptides comprise one or more Tregitope of the present disclosure operatively linked to a heterologous polypeptide. "Operatively linked" indicates that the polypeptide (e.g., the one or more $T_{reg}$ activating regulatory T-cell epitope, Tregitope, or T-cell epitope polypeptide of the present disclosure) and the heterologous protein are fused in-frame or chemically-linked or otherwise bound. In aspects, a chimeric or fusion polypeptide composition comprises a polypeptide, said polypeptide having a sequence comprising one or more of SEQ ID NOS: 1-14 of the present disclosure, wherein said one or more of SEQ ID NOS: 1-14 is not naturally included in the polypeptide and/or said of one or more of SEQ ID NOS: 1-14 is not located at its natural position in the polypeptide. In aspects, the one or more of SEQ ID NOS: 1-14 of the present disclosure can be joined, linked to (e.g., fused in-frame, chemically-linked, or otherwise bound), and/or inserted into the polypeptide. In aspects, the one or more of SEQ ID NOS: 1-14 of the present disclosure can be joined or linked to (e.g., fused in-frame, chemically-linked, or otherwise bound) to a small molecule, drug, or drag fragment, for example but not limited to, a drug or drug fragment that is binds with high affinity to defined HLAs. In aspects of the above chimeric, fusion polypeptide, and fusion product compositions, the one or more polypeptides ($T_{reg}$ activating regulatory T-cell epitope, Tregitope, or T-cell epitope polypeptide) of the present disclosure comprises, consists of, or consists essentially of one or more of SEQ ID NOS: 1-14. In aspects, the one or more polypeptides ($T_{reg}$ activating regulatory T-cell epitope, Tregitope, or T-cell epitope polypeptide) of the present disclosure comprises, consists of, or consists essentially of a sequence one or more of SEQ ID NOS: 1-2. In aspects, the one or more polypeptides ($T_{reg}$ activating regulatory T-cell epitope, Tregitope, or T-cell epitope polypeptide) of the present disclosure comprises, consists of, or consists essentially the amino acid sequence of SEQ ID NO: 1.

An isolated polypeptide (e.g., an isolated $T_{reg}$ activating regulatory T-cell epitope, Tregitope, or T-cell epitope polypeptide) can be purified from cells that naturally express it, purified from cells that have been altered to express it (recombinant), or synthesized using known protein synthesis methods. In one embodiment, a Tregitope is produced by recombinant DNA or RNA techniques. For example, a nucleic acid molecule encoding the Tregitope is cloned into an expression vector, the expression vector introduced into a host cell and the polypeptide expressed in the host cell. The Tregitope can then be isolated from the cells by an appropriate purification scheme using standard protein purification techniques.

For the purposes of the present disclosure, Tregitopes can include, for example, modified forms of naturally occurring amino acids such as D-stereoisomers, non-naturally occurring amino acids; amino acid analogs; and mimetics. Further, in aspects, Tregitopes can include retro-inverso peptides of the instantly disclosed Tregitopes (T cell epitope polypeptides).

Although any methods and materials similar or equivalent to those described herein can be used in the practice or testing of the present disclosure, the preferred methods and materials are described. Other features, objects, and advantages of the present disclosure will be apparent from the description and the Claims. In the Specification and the appended Claims, the singular forms include plural referents unless the context clearly dictates otherwise. Unless defined otherwise, all technical and scientific terms used herein have the same meaning as commonly understood by one of ordinary skill in the art to which this invention belongs. All references cited herein are incorporated herein by reference in their entirety and for all purposes to the same extent as if each individual publication, patent, or patent application was specifically and individually indicated to be incorporated by reference in its entirety for all purposes.

Compositions

In aspects, the present disclosure provides Tregitope compositions, including polypeptides ($T_{reg}$ activating regulatory T-cell epitope, Tregitope, or T-cell epitope polypeptide, which in aspects may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; isolated, synthetic, or recombinant chimeric or fusion polypeptide compositions as disclosed herein; and/or pharmaceutical compositions or formulations as disclosed herein. In aspects, the Tregitope compositions include one or more of the following regulatory Tregitopes (as well as fragments thereof, variants thereof, and fragments of such variants, provided said fragments and/or variants retain MHC binding propensity and TCR specificity):

ILTIHFTGHSFIYGK; (SEQ ID NO: 1)

IHSIHFSGHVFTVRK; (SEQ ID NO: 2)

KIVFKNMASRPYSIY; (SEQ ID NO: 3)

FAVFDENKSWYLEDN; (SEQ ID NO: 4)

ESNIMSTINGYVPES; (SEQ ID NO: 5)

EKDIHSGLIGPLLI; (SEQ ID NO: 6)

SHEFHAINGMIYSLP; (SEQ ID NO: 7)

IHFTGHSFI; (SEQ ID NO: 8)

IHFSGHVFT; (SEQ ID NO: 9)

FKNMASRPY; (SEQ ID NO: 10)

FDENLSWYL; (SEQ ID NO: 11)

IMSTINGYV; (SEQ ID NO: 12)

IHSGLIGPL;
and (SEQ ID NO: 13)

FHAINGMIY. (SEQ ID NO: 14)

In one aspect, the present disclosure provides a novel class of T cell epitopes (which may be isolated, synthetic, or recombinant), termed 'Tregitopes', which comprise a peptide or polypeptide chain derived from common human proteins. Tregitopes of the present disclosure are highly conserved among known variants of their source proteins (e.g., present in more than 10% of known variants). Tregitopes of the present disclosure comprise at least one putative T cell epitope as identified by EpiMatrix™ analysis. EpiMatrix™ is a proprietary computer algorithm developed by EpiVax (Providence, R.I.), which is used to screen protein sequences for the presence of putative T cell epitopes. Input sequences are parsed into overlapping 9-mer frames where each frame overlaps the last by 8 amino acids. Each of the resulting frames is then scored for predicted binding affinity with respect to a panel of eight common Class II HLA alleles (DRB1*0101, DRB1*0301, DRB1*0401, DRB1*0701, DRB1*0801, DRB1*1101, DRB1*1301, and DRB1*1501). Raw scores are normalized against the scores of a large sample of randomly generated peptides. The resulting "Z" score is reported. In aspects, any 9-mer peptide with an allele-specific EpiMatrix™ Z-score in excess of 1.64, theoretically the top 5% of any given sample, is considered a putative T cell epitope.

Peptides containing clusters of putative T cell epitopes are more likely to test positive in validating in vitro and in vivo assays. The results of the initial EpiMatrix™ analysis are further screened for the presence of putative T cell epitope "clusters" using a second proprietary algorithm known as Clustimer™ algorithm. The Clustimer™ algorithm identifies sub-regions contained within any given amino acid sequence that contains a statistically unusually high number of putative T cell epitopes. Typical T-cell epitope "clusters" range from about 9 to roughly 30 amino acids in length and, considering their affinity to multiple alleles and across multiple 9-mer frames, can contain anywhere from about 4 to about 40 putative T cell epitopes. Each epitope cluster identified an aggregate EpiMatrix™ score is calculated by summing the scores of the putative T cell epitopes and subtracting a correcting factor based on the length of the candidate epitope cluster and the expected score of a randomly generated cluster of the same length. EpiMatrix™ cluster scores in excess of +10 are considered significant. In aspects, the Tregitopes of the instant disclosure contain several putative T cell epitopes forming a pattern known as a T cell epitope cluster.

Many of the most reactive T cell epitope clusters contain a feature referred to as an "EpiBar™". As previously described, an EpiBar™ is a single 9-mer frame that is predicted to be reactive to at least four different HLA alleles. In aspects, the Tregitopes of the present disclosure can comprise one or more EpiBars™.

In aspects, Tregitopes of the present disclosure bind to at least one and preferably two or more common HLA class II molecules with at least a moderate affinity (e.g., in aspects, <200 µM $IC_{50}$ in HLA binding assays based on soluble HLA molecules). In aspects, Tregitopes of the present disclosure are capable of being presented at the cell surface by APCs in the context of at least one and, in other aspects, two or more alleles of the HLA. In this context, the Tregitope-HLA complex can be recognized by naturally occurring $T_{Regs}$ (in aspects, including natural $T_{Regs}$ and/or adaptive $T_{Regs}$) having TCRs that are specific for the Tregitope-HLA complex and circulating in normal control subjects. In aspects, the recognition of the Tregitope-HLA complex can cause the matching regulatory T cell to be activated and to secrete regulatory cytokines and chemokines.

In aspects, the present disclosure is directed to a polypeptide (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14. The phrase "consisting essentially of" is intended to mean that a polypeptide according to the present disclosure, in addition to having the sequence according to any of SEQ ID NOS: 1-14 or a variant thereof, contains additional amino acids or residues that may be present at either terminus of the peptide and/or on a side chain that are not necessarily forming part of the peptide that functions as an MHC ligand and provided they do not substantially impair the activity of the peptide to function as a Tregitope. In aspects, a polypeptide ($T_{reg}$ activating regulatory T-cell epitope, Tregitope, or T-cell epitope polypeptide) comprises, consists of, or consists essentially of one or more of SEQ ID NOS: 1-2. In aspects, a polypeptide ($T_{reg}$ activating regulatory T-cell epitope, Tregitope, or T-cell epitope polypeptide) comprises, consists of, or consists essentially of the amino acid sequence of SEQ ID NO: 1. In aspects, a polypeptide comprises one or more of SEQ ID NOS: 1-14 of the present disclosure (in aspects, including fragments and variants thereof of SEQ ID NOS: 1-14, provided said fragments and/or variants retain MHC binding propensity and TCR specificity) joined to, linked to (e.g., fused in-frame, chemically-linked, or otherwise bound), and/or inserted into a heterologous polypeptide (e.g. but not limited to, an antibody (which can be IgG, IgM, IgA, IgD or IgE molecules or antigen-specific antibody fragments thereof (including, but not limited to, a Fab, F(ab')$_2$, Fv, disulfide linked Fv, scFv, single domain antibody, closed conformation multispecific antibody, disulphide-linked scfv, diabody)). In aspects, the one or more of SEQ ID NOS: 1-14 may be joined to, linked to (e.g., fused in-frame, chemically-linked, or otherwise bound), and/or inserted into a heterologous polypeptide as a whole, although it may be made up from a joined to, linked to (e.g., fused in-frame, chemically-linked, or otherwise bound), and/or inserted amino acid sequence, together with flanking amino acids of the heterologous polypeptide. In aspects, the present disclosure is directed to polypeptide (which, in aspects, may be an isolated, synthetic, or recombinant) having a sequence comprising one or more of SEQ ID NOS: 1-14, wherein said one or more of SEQ ID NOS: 1-14 is not naturally included in the polypeptide and/or said one or more of SEQ ID NOS: 1-14 is not located at its natural position in the polypeptide. In aspects, a polypeptide (which, in aspects, may be an isolated, synthetic, or recombinant) has a sequence comprising one or more of SEQ ID NOS: 1, 3-8, and 10-14, wherein said polypeptide does not comprise human coagulation Factor V. In aspects, a polypeptide (which, in aspects, may be an isolated, synthetic, or recombinant) has a sequence comprising one or more of SEQ ID NOS: 2 or 9, wherein said isolated, synthetic, or recombinant polypeptide does not comprise human coagulation Factor VIII. In aspects, an isolated, synthetic, or recombinant polypeptide comprises one or more of SEQ ID NOS: 1-14, wherein said one or more of SEQ ID NOS: 1-14 is not naturally included in the polypeptide and/or said one or more of SEQ ID NOS: 1-14 is not located at its natural position in the polypeptide. In aspects, isolated, synthetic, or recombinant Tregitopes of the present disclosure include one or more of:

```
                         (SEQ ID NO: 1)
ILTIHFTGHSFIYGK;

(SEQ ID NO: 2)
IHSIHFSGHVFTVRK;

(SEQ ID NO: 3)
KIVFKNMASRPYSIY;

(SEQ ID NO: 4)
FAVFDENKSWYLEDN;

(SEQ ID NO: 5)
ESNIMSTINGYVPES;

(SEQ ID NO: 6)
EKDIHSGLIGPLLI;

(SEQ ID NO: 7)
SHEFHAINGMIYSLP;

(SEQ ID NO: 8)
IHFTGHSFI;

(SEQ ID NO: 9)
IHFSGHVFT;
```

```
                         (SEQ ID NO: 10)
FKNMASRPY;

(SEQ ID NO: 11)
FDENLSWYL;

(SEQ ID NO: 12)
IMSTINGYV;

(SEQ ID NO: 13)
IHSGLIGPL;
and (SEQ ID NO: 14)
FHAINGMIY.
``` and fragments thereof, variants thereof, and fragments of such variants thereof, provided said fragments and/or variants retain MHC binding propensity and TCR specificity.

In aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can be purified to homogeneity or partially purified. It is understood, however, that preparations in which the Tregitope compositions are not purified to homogeneity are useful. The critical feature is that the preparation allows for the desired function of the Tregitope, even in the presence of considerable amounts of other components. Thus, the present disclosure encompasses various degrees of purity. In one embodiment, the language "substantially free of cellular material" includes preparations of the Tregitope having less than about 30% (by dry weight) other proteins (e.g., contaminating protein), less than about 20% other proteins, less than about 10% other proteins, less than about 5% other proteins, less than about 4% other proteins, less than about 3% other proteins, less than about 2% other proteins, less than about 1% other proteins, or any value or range therebetween.

In aspects, when a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) is recombinantly produced, said Tregitope composition can also be substantially free of culture medium, for example, culture medium represents less than about 20%, less than about 10%, or less than about 5% of the volume of the Tregitope, nucleic acid, or chimeric or fusion polypeptide preparation. The language "substantially free of chemical precursors or other chemicals" includes preparations of the polypeptide, nucleic acid, or chimeric or fusion polypeptide in which it is separated from chemical precursors or other chemicals that are involved in the Tregitope's synthesis. The language "substantially free of chemical precursors or other chemicals" can include, for example, preparations of the Tregitope, nucleic acid, or chimeric or fusion polypeptide having less than about 30% (by dry weight) chemical precursors or other chemicals, less than about 20% chemical precursors or other chemicals, less than about 10% chemical precursors or other chemicals, less than about 5% chemical precursors or other chemicals, less than about 4% chemical precursors or other chemicals, less than about 3% chemical precursors or other chemicals, less than about 2% chemical precursors or other chemicals, or less than about 1% chemical precursors or other chemicals.

As used herein, two polypeptides (or a region of the polypeptides) are substantially homologous or identical when the amino acid sequences are at least about 45-55%, typically at least about 70-75%, more typically at least about 80-85%, more typically greater than about 90%, and more typically greater than 95% or more homologous or identical. To determine the percent homology or identity of two amino acid sequences, or of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (e.g., percent homology equals the number of identical positions/total number of positions× 100).

In aspects, the present disclosure also encompasses polypeptides (e.g., Tregitopes and Tregitope compositions as disclosed herein) having a lower degree of identity but having sufficient similarity so as to perform one or more of the same functions performed by a polypeptide encoded by a nucleic acid molecule of the present disclosure, particularly that any such variants retain MHC binding propensity and TCR specificity. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found (Bowie J U et al., (1990), Science, 247(4948):130610, which is herein incorporated by reference in its entirety).

In aspects, a variant polypeptide can differ in amino acid sequence by one or more substitutions, deletions, insertions, inversions, fusions, and truncations or a combination of any of these. Variant polypeptides can be fully functional (e.g., retain MHC binding propensity and TCR specificity) or can lack function in one or more activities. Fully functional variants typically contain only conservative variation or variation in non-critical residues or in non-critical regions; in this case, typically MHC contact residues provided MHC binding is preserved. Functional variants can also contain substitution of similar amino acids that result in no change or an insignificant change in function (e.g., retain MHC binding propensity and TCR specificity). Alternatively, such substitutions can positively or negatively affect function to some degree. Non-functional variants typically contain one or more non-conservative amino acid substitutions, deletions, insertions, inversions, or truncation or a substitution, insertion, inversion, or deletion in a critical residue or critical region; in this case, typically TCR contact residues.

In aspects, the present disclosure also includes Tregitope compositions (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) that include polypeptide fragments of the instantly-disclosed Tregitopes. In aspects, the present disclosure also encompasses fragments of the variants of the Tregitopes described herein. In aspects, as used herein, a fragment comprises at least about nine contiguous amino acids. Useful fragments (and fragments of the variants of the Tregitopes described herein) include those that retain one or more of the biological activities of the Tregitope, particularly MHC binding propensity and TCR specificity. Biologically active fragments are, for example, about 9, 12, 15, 16, 20 or 30 or more amino acids in length, including any value or range therebetween. Fragments can be discrete (not fused to other amino acids or polypeptides) or can be within a larger polypeptide. Several fragments can be comprised within a single larger polypeptide. In aspects, a fragment designed for expression in a host can have heterologous pre- and pro-polypeptide regions fused to the amino terminus of the polypeptide fragment and an additional region fused to the carboxyl terminus of the fragment.

In aspects, Tregitopes of the present disclosure can include allelic or sequence variants ("mutants") or analogs thereof, or can include chemical modifications (e.g., pegylation, glycosylation). In aspects, a mutant retains the same functions performed by a polypeptide encoded by a nucleic acid molecule of the present disclosure, particularly MHC binding propensity and TCR specificity. In aspects, a mutant can provide for enhanced binding to MHC molecules. In aspects, a mutant can lead to enhanced binding to TCRs. In another instance, a mutant can lead to a decrease in binding to MHC molecules and/or TCRs. Also contemplated is a mutant that binds, but does not allow signaling via the TCR.

In aspects, the present disclosure also provides chimeric or fusion polypeptide compositions. In aspects, the present disclosure provides isolated, synthetic, or recombinant chimeric or fusion polypeptide compositions wherein one or more of the instantly-disclosed Tregitopes is a part thereof. In aspects, a chimeric or fusion polypeptide composition comprises one or more polypeptides ($T_{reg}$ activating regulatory T-cell epitope, Tregitope, or T-cell epitope polypeptide) of the present disclosure joined to, linked to (e.g., fused in-frame, chemically-linked, or otherwise bound), and/or inserted into a heterologous polypeptide (e.g. but not limited to, an antibody (which can be IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody)). As previously described, with respect to the one or more Tregitopes of the instant disclosure, the term "heterologous polypeptide" is intended to mean that the one or more Tregitopes of the instant disclosure are heterologous to, or not included naturally, in the heterologous polypeptide. In aspects, one or more of the instantly-disclosed polypeptides ($T_{reg}$ activating regulatory T-cell epitopes, Tregitopes, or T-cell epitope polypeptides) may be inserted into the heterologous polypeptide (e.g., through recombinant techniques, mutagenesis techniques, or other known means in the art), may be added to the C-terminus, and/or added to the N-terminus of the heterologous polypeptide. For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety). In aspects, chimeric or fusion polypeptides comprise one or more of the instantly-disclosed polypeptides ($T_{reg}$ activating regulatory T-cell epitopes, Tregitopes, or T-cell epitope polypeptides) operatively linked to a heterologous polypeptide. "Operatively linked" indicates that the one or more of the instantly-disclosed polypeptides ($T_{reg}$ activating regulatory T-cell epitopes, Tregitopes, or T-cell epitope polypeptides) and the heterologous polypeptide are fused in-frame or chemically-linked or otherwise bound. In aspects of the above isolated, synthetic, or recombinant chimeric or fusion polypeptide compositions, the one or more polypeptides ($T_{reg}$ activating regulatory T-cell epitope, Tregitope, or T-cell epitope polypeptide) of the present disclosure have a sequence comprising, consisting of, or consisting essentially of one or more of SEQ ID NOS: 1-14. In aspects of the chimeric or fusion polypeptide compositions, the one or more of SEQ ID NOS: 1-14 may be joined to, linked to (e.g., fused in-frame, chemically-linked, or otherwise bound), and/or inserted into a heterologous polypeptide as a whole, although it may be made up from a joined to, linked to (e.g., fused in-frame, chemically-linked, or otherwise bound), and/or inserted amino acid sequence, together with flanking amino acids of the heterologous polypeptide. In aspects, a chimeric or fusion polypeptide composition comprises a polypeptide, said polypeptide having a sequence comprising one or more of SEQ ID NOS: 1-14 of the present disclosure, wherein said one or more of SEQ ID NOS: 1-14 is not naturally included in the polypeptide and/or said of one or more of SEQ ID NOS: 1-14 is not located at its natural position in the polypeptide. In aspects, the one or more of SEQ ID NOS: 1-14 of the present disclosure can be joined, linked to (e.g., fused in-frame, chemically-linked, or otherwise bound), and/or inserted into the polypeptide. In aspects, chimeric or fusion polypeptide compositions comprise one or more of the instantly-disclosed Tregitopes operatively linked to a heterologous polypeptide having an amino acid sequence not substantially homologous to the Tregitope. In aspects, the chimeric or fusion polypeptide does not affect function of the Tregitope per se. For example, the fusion polypeptide can be a GST-fusion polypeptide in which the Tregitope sequences are fused to the C-terminus of the GST sequences. Other types of fusion polypeptides include, but are not limited to, enzymatic fusion polypeptides, for example beta-galactosidase fusions, yeast two-hybrid GAL fusions, poly-His fusions and Ig fusions. Such fusion polypeptides, particularly poly-His fusions or affinity tag fusions, can facilitate the purification of recombinant polypeptide. In certain host cells (e.g., mammalian host cells), expression and/or secretion of a polypeptide can be increased by using a heterologous signal sequence. Therefore, in aspects, the fusion polypeptide contains a heterologous signal sequence at its N-terminus. In aspects of the above recombinant chimeric or fusion polypeptide compositions, the heterologous polypeptide or polypeptide comprises a biologically active molecule. In aspects, the biologically active molecule is selected from the group consisting of an immunogenic molecule, a T cell epitope, a viral protein, and a bacterial protein. In aspects, the biologically active molecule is a human Coagulation Factor VIII supplement. In aspects, the one or more of SEQ ID NOS: 1-14 of the present disclosure can be joined or linked to (e.g., fused in-frame, chemically-linked, or otherwise bound) to a small molecule, drug, or drug fragment. For example, one or more of SEQ ID NOS: 1-14 of the present disclosure can be joined or linked to (e.g., fused in-frame, chemically-linked, or otherwise bound) a drug or drug fragment that is binds with high affinity to defined HLAs. In aspects of the above chimeric or fusion polypeptide compositions or fusion products, the one or more polypeptides ($T_{reg}$ activating regulatory T-cell epitope, Tregitope, or T-cell epitope polypeptide) of the present disclosure included therein have a sequence comprising, consisting of, or consisting essentially of one or more of SEQ ID NOS: 1-14. In aspects of the above chimeric or fusion polypeptide compositions or fusion products, the one or more polypeptides ($T_{reg}$ activating regulatory T-cell epitope, Tregitope, or T-cell epitope polypeptide) of the present disclosure included therein have a sequence comprising, consisting of, or consisting essentially of one or more of SEQ ID NOS: 1-2. In aspects of the above chimeric or fusion polypeptide compositions or fusion products, the one or more polypeptides ($T_{reg}$ activating regulatory T-cell epitope, Tregitope, or T-cell epitope polypeptide) of the present disclosure included therein have a sequence comprising, consisting of, or consisting essentially of SEQ ID NOS: 1. In aspects of the above-described chimeric or fusion polypeptide compositions or fusion products, the chimeric or fusion polypeptide compositions or fusion products can be recombinant, isolated, and/or synthetic.

A chimeric or fusion polypeptide composition can be produced by standard recombinant DNA or RNA techniques as are known in the art. For example, DNA or RNA fragments coding for the different polypeptide sequences may be ligated together in-frame in accordance with conventional techniques. In another embodiment, the fusion gene can be synthesized by conventional techniques including automated DNA synthesizers. Alternatively, polymerase chain reaction (PCR) amplification of nucleic acid fragments can be carried out using anchor primers which give rise to complementary overhangs between two consecutive nucleic acid fragments which can subsequently be annealed and re-amplified to generate a chimeric nucleic acid sequence. (Short Protocols in Molecular Biology: A Compendium of Methods from Current Protocols in Molecular Biology, ($2^{ND}$, 1992), FM Asubel et al. (eds), Green Publication Associates, New York, N.Y. (Publ), ISBN: 9780471566355, which are herein incorporated by reference in their entirety).

Further, one or more polypeptides ($T_{reg}$ activating regulatory T-cell epitope, Tregitope, or T-cell epitope polypeptide) of the present disclosure (e.g., one or more Tregitopes of the present disclosure having a sequence comprising, consisting of, or consisting essentially of one or more of SEQ ID NOS: 1-14) can be inserted into a heterologous polypeptide or inserted into a non-naturally occurring position of a polypeptide through recombinant techniques, synthetic polymerization techniques, mutagenesis techniques, or other standard techniques known in the art. For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety).

Moreover, many expression vectors are commercially available that already encode a fusion moiety (e.g., a GST protein). A nucleic acid molecule encoding a Tregitope of the invention can be cloned into such an expression vector such that the fusion moiety is linked in-frame to the at least one Tregitope.

In aspects, the present disclosure also provides for nucleic acids (e.g., DNA, RNA, vectors, viruses, or hybrids thereof, all of which may be isolated, synthetic, or recombinant) that encode in whole or in part one or more polypeptides of the present disclosure and/or chimeric or fusion polypeptide compositions of the present disclosure. In aspects of the nucleic acids encoding one or more polypeptides of the present disclosure or chimeric or fusion polypeptide compositions of the present disclosure, the one or more polypeptides or recombinant chimeric or fusion polypeptide composition have a sequence comprising, consisting of, or consisting essentially of one or more of SEQ ID NOS: 1-14. In aspects, the nucleic acid further comprises, or is contained within, an expression cassette, a plasmid, and expression vector, or recombinant virus, wherein optionally the nucleic acid, or the expression cassette, plasmid, expression vector, or recombinant virus is contained within a cell, optionally a human cell or a non-human cell, and optionally the cell is transformed with the nucleic acid, or the expression cassette, plasmid, expression vector, or recombinant virus. In aspects, cells are transduced, transfected, or otherwise engineered to contain within one or more of e.g., polypeptides ($T_{reg}$ activating regulatory T-cell epitope, Tregitope, or T-cell epitope polypeptide) of the present disclosure; isolated, synthetic, or recombinant nucleic acids, expression cassettes, plasmids, expression vectors, or recombinant viruses as disclosed herein; and/or isolated, synthetic, or recombinant chimeric or fusion polypeptide compositions as disclosed herein. In aspects, the cell can be a mammalian cell, bacterial cell, insect cell, or yeast cell. In aspects, the nucleic acid molecules of the present disclosure can be inserted into vectors and used, for example, as expression vectors or gene therapy vectors. Gene therapy vectors can be delivered to a subject by, e.g., intravenous injection, local administration (U.S. Pat. No. 5,328,470) or by stereotactic injection (Chen S H et al., (1994), Proc Natl Acad Sci USA, 91(8):3054-7, which are herein incorporated by reference in their entirety). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. Such pharmaceutical compositions can be included in a container, pack, or dispenser together with instructions for administration. In aspects of the above nucleic acids (e.g., DNA, RNA, vectors, viruses, or hybrids thereof) that encode in whole or in part at least one polypeptide ($T_{reg}$ activating regulatory T-cell epitope, Tregitope, or T-cell epitope polypeptide) of the present disclosure and/or chimeric or fusion polypeptides of the present disclosure, the nucleic acids encode one or more of: polypeptides comprising, consisting of, or consisting essentially of one or more of SEQ ID NOS: 1-14; polypeptides comprising consisting of, or consisting essentially of one or more of SEQ ID NOS: 1-2; or polypeptides comprising, consisting, or consisting essentially of SEQ ID NO: 1. In aspects, the present disclosure is directed to a vector comprising a nucleic acid of the present disclosure encoding one or more polypeptides ($T_{reg}$ activating regulatory T-cell epitope, Tregitope, or T-cell epitope polypeptide) of the present disclosure or a chimeric or fusion polypeptide composition of the present disclosure, e.g., but not limited to, a nucleic acid (DNA or RNA) encoding at least one regulatory T-cell epitope comprising, consisting of, or consisting essentially of one or more of SEQ ID NOS: 1-14. In aspects, the present disclosure is directed to a cell comprising a vector of the present disclosure. In aspects, the cell can be a mammalian cell, bacterial cell, insect cell, or yeast cell.

The nucleic acids provided herein (whether RNA, DNA, vectors, viruses or hybrids thereof) that encode in whole or in part one or one or more polypeptides of the present disclosure and/or chimeric or fusion polypeptides of the present disclosure can be isolated from a variety of sources, genetically engineered, amplified, synthetically produced, and/or expressed/generated recombinantly. Recombinant polypeptides generated from these nucleic acids can be individually isolated or cloned and tested for a desired activity. Any recombinant expression system can be used, including e.g. in vitro, bacterial, fungal, mammalian, yeast, insect or plant cell expression systems. In aspects nucleic acids provided herein are synthesized in vitro by well-known chemical synthesis techniques (as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066, all of which are herein incorporated by reference in their entirety). Further, techniques for the manipulation of nucleic acids provided herein, such as, e.g., subcloning, labeling probes (e.g., random-primer labeling using Klenow polymerase, nick translation, amplification), sequencing, hybridization and the like are well described in the scientific and patent literature (see, e.g., Sambrook, ed., Molecular Cloning: A Laboratory Manual ($2^{ND}$ Ed.), Vols. 1-3, Cold Spring Harbor Laboratory, (1989); Current Protocols In Molecular Biology, Ausubel, ed. John Wiley & Sons, Inc., New York (1997); Laboratory Techniques In Biochemistry And Molecular Biology: Hybridization With Nucleic Acid Probes, Part I. Theory and Nucleic Acid Preparation, Tijssen, ed. Elsevier, N.Y. (1993), all of which are herein incorporated by reference in their entirety).

In aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) are combined in admixture with an antigen, allergen, or a therapeutic protein. Such compositions are useful in methods of inducing tolerance to the antigen, allergen, or a therapeutic protein in a subject in need thereof, wherein local delivery of the admixture with an antigen, allergen, or a therapeutic protein results in increased tolerance to the antigen or allergen in the subject, and delivered with an appropriate excipient resulting in induced tolerance to the antigen, allergen, or a therapeutic protein. This combination may be administered with the Tregitope compositions of the present disclosure bound either covalently or non-covalently, or they may be administered as an admixture, or a branched or chemically-link preparation. Such compositions are useful in methods of inducing tolerance to an antigen or allergen or a therapeutic protein (e.g., but not limited to, Insulin, coagulation Factor VIII (FVIII) and/or coagulation Factor VIII supplements). For example, such composition are useful in a subject in need thereof, wherein local delivery of the admixture with an antigen or allergen or therapeutic protein results in increased tolerance to the antigen or allergen or therapeutic protein in the subject, and delivered with an appropriate excipient resulting in induced tolerance to the antigen or allergen or therapeutic protein. In aspects, the Tregitope compositions of the present disclosure are in combination with a therapeutic blood clotting protein for the purpose of suppressing an immune response against the therapeutic blood clotting protein in a T-cell dependent manner. This combination may be administered with the Tregitope compositions of the present disclosure bound either covalently or non-covalently, or they may be administered as an admixture. Such compositions are useful in methods of inducing tolerance to the therapeutic blood clotting protein in a subject in need thereof, wherein local delivery of the admixture with the therapeutic blood clotting protein results in increased tolerance to the therapeutic blood clotting protein in the subject, and delivered with an appropriate excipient resulting in induced tolerance to the therapeutic blood clotting protein. In aspects of the above Tregitope compositions combined in admixture with an antigen or allergen or a therapeutic protein or bound either covalently or non-covalently to with an antigen or allergen or a therapeutic protein, the one or more polypeptides ($T_{reg}$ activating regulatory T-cell epitope, Tregitope, or T-cell epitope polypeptide) of the present disclosure included therein have a sequence: comprising, consisting of, or consisting essentially of one or more of SEQ ID NOS: 1-14; comprising, consisting of, or consisting essentially of one or more of SEQ ID NOS: 1-2, and more particularly SEQ ID NO: 1

Pharmaceutical Compositions and Formulations

In aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; and/or chimeric or fusion polypeptide compositions as disclosed herein (which in aspects may be isolated, synthetic, or recombinant)) may be comprised in a pharmaceutical composition or formulation. In aspects, pharmaceutical compositions or formulations generally comprise a Tregitope composition of the present disclosure and a pharmaceutically-acceptable carrier and/or excipient. In aspects, said pharmaceutical compositions are suitable for administration. Pharmaceutically-acceptable carriers and/or excipients are determined in part by the particular composition being administered, as well as by the particular method used to administer the composition. Accordingly, there is a wide variety of suitable formulations of pharmaceutical compositions for administering the instantly-disclosed Tregitope compositions (see, e.g., Remington's Pharmaceutical Sciences, ($18^{TH}$ Ed, 1990), Mack Publishing Co., Easton, PA Publ, which is herein incorporated by reference in its entirety). In aspects, the pharmaceutical compositions are generally formulated as sterile, substantially isotonic, and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, excipients, and reagents, are used interchangeably and represent that the materials are capable of administration to or upon a subject without the production of undesirable physiological effects to a degree that would prohibit administration of the composition. For example, "pharmaceutically-acceptable excipient" means, for example, an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art would be able to determine the appropriate timing, sequence and dosages of administration for particular Tregitope compositions of the present disclosure.

In aspects, preferred examples of such carriers or diluents include, but are not limited to, water, saline, Ringer's solutions, dextrose solution, and 5% human serum albumin. Liposomes and non-aqueous vehicles such as fixed oils can also be used. The use of such media and compounds for pharmaceutically active substances is well known in the art. Except insofar as any conventional media or compound is incompatible with the Tregitope compositions of the present disclosure and as previously described above (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), use thereof in the compositions is contemplated. Supplementary active compounds can also be incorporated into the compositions.

In aspects, Tregitope compositions of the present disclosure of the present disclosure (including one or more of e.g., polypeptides (which may be termed herein as "T$_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) are formulated to be compatible with their intended route of administration. The Tregitope compositions of the present disclosure can be administered by parenteral, topical, intravenous, oral, subcutaneous, intraarterial, intradermal, transdermal, rectal, intracranial, intrathecal, intraperitoneal, intranasal; vaginally; intramuscular route or as inhalants. In aspects, Tregitope compositions of the present disclosure can be injected directly into a particular tissue where deposits have accumulated, e.g., intracranial injection. In other aspects, intramuscular injection or intravenous infusion may be used for administration of Tregitope compositions of the present disclosure. In some methods, Tregitope compositions of the present disclosure are injected directly into the cranium. In some methods, Tregitope compositions of the present disclosure are administered as a sustained release composition or device, such as but not limited to a Medipad™ device.

In aspects, Tregitope compositions of the present disclosure (including one or more of e.g., polypeptides (which may be termed herein as "T$_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can optionally be administered in combination with other agents that are at least partly effective in treating various medical conditions as described herein. For example, in the case of administration into the central nervous system of a subject, Tregitope compositions of the present disclosure can also be administered in conjunction with other agents that increase passage of the agents of the invention across the blood-brain barrier.

In aspects, solutions or suspensions used for parenteral, intradermal, or subcutaneous application can include, but are not limited to, the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. Examples of excipients can include starch, glucose, lactose, sucrose, gelatin, malt, rice, flour, chalk, silica gel, water, ethanol, DMSO, glycol, propylene, dried skim milk, and the like. The composition can also contain pH buffering reagents, and wetting or emulsifying agents.

In aspects, the parenteral preparation can be enclosed in ampoules, disposable syringes or multiple dose vials made of glass or plastic.

In aspects, pharmaceutical compositions or formulations suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition is sterile and should be fluid to the extent that easy syringeability exists. It is stable under the conditions of manufacture and storage and is preserved against the contaminating action of microorganisms such as bacteria and fungi. In aspects Tregitopes formulations may include aggregates, fragments, breakdown products and post-translational modifications, to the extent these impurities bind HLA and present the same TCR face to cognate T cells they are expected to function in a similar fashion to pure Tregitopes. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound that delays absorption, e.g., aluminum monostearate and gelatin.

In aspects, sterile injectable solutions can be prepared by incorporating the Tregitope compositions of the present disclosure (including one or more of e.g., polypeptides (which may be termed herein as "T$_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Further, Tregitope compositions of the present disclosure can be administered in the form of a depot injection or implant preparation that can be formulated in such a manner as to permit a sustained or pulsatile release of the active ingredient.

In aspects, oral compositions generally include an inert diluent or an edible carrier and can be enclosed in gelatin capsules or compressed into tablets. In aspects, for the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. In aspects, the tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel or corn starch; a lubricant such as magnesium stearate or Sterotes; a glidant such as colloidal silicon dioxide; a sweetening compound such as sucrose or saccharin; or a flavoring compound such as peppermint, methyl salicylate or orange flavoring.

For administration by inhalation, Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can be delivered in the form of an aerosol spray from pressured container or dispenser that contains a suitable propellant, e.g., a gas such as carbon dioxide, or a nebulizer.

In aspects, systemic administration of the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the Tregitope may be formulated into ointments, salves, gels, or creams and applied either topically or through transdermal patch technology as generally known in the art.

In aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can also be prepared in the form of suppositories (e.g., with conventional suppository bases such as cocoa butter and other glycerides) or retention enemas for rectal delivery.

In aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) are prepared with carriers that protect the Tregitope compositions against rapid elimination from the body, such as a controlled-release formulation, including implants and microencapsulated delivery systems. Biodegradable, biocompatible polymers can be used, such as, for example, ethylene vinyl acetate, polyanhydrides, polyglycolic acid, collagen, polyorthoesters, and polylactic acid. Methods for preparation of such formulations will be apparent to those skilled in the art. The materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art (U.S. Pat. No. 4,522,811, which is herein incorporated by reference in its entirety). In aspects, the Tregitope compositions of the present disclosure can be implanted within or linked to a biopolymer solid support that allows for the slow release of the Tregitope compositions to the desired site.

In aspects, it is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the instant disclosure are dictated by and directly dependent on the unique characteristics of the binding agent and the particular therapeutic effect to be achieved, and the limitations inherent in the art of compounding such Tregitope compositions for the treatment of a subject.

In aspects, the one or more polypeptides ($T_{reg}$ activating regulatory T-cell epitope, Tregitope, or T-cell epitope polypeptide, which in aspects may be isolated, synthetic, or recombinant) as disclosed herein can also be administered to the patient by ex vivo pulsing of isolated dendritic cells (DC) with Tregitopes, followed by reinfusion of the pulsed cells into the patient. These can be prepared according to methods known to those skilled in the art (see, e.g., Butterfield, (2013), Front Immunol, 4:454 and Dissanayake et al., (2014), PLoS One, 9(3)1-10, which is herein incorporated by reference in its entirety). These reinfusions may be administered by the above methods and compositions.

Methods of Use of Tregitope Compositions

Stimulating regulatory T cells with Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can stimulate, induce, and/or expand corresponding naturally occurring $T_{Reg}$ populations (in aspects, including natural $T_{Regs}$ and/or adaptive $T_{Regs}$) and in aspects results in increased secretion of one or more of the following cytokines and chemokines: IL-10, IL-35, TGF-β, TNF-α and MCP1. In aspects, stimulation can result in the increased expression of IL-2Rα by corresponding naturally occurring $T_{Reg}$ populations (in aspects, including natural $T_{Regs}$ and/or adaptive $T_{Regs}$) and deprivation of IL-2 to effector T cells. In further aspects, stimulation can result in increased perforin granzyme by corresponding naturally occurring $T_{Reg}$ populations (in aspects, including natural $T_{Regs}$ and/or adaptive $T_{Regs}$), which allows for such Treg populations to kill T effector cells and other immune stimulatory cells. In even further aspects, such stimulation can result in the generation of immune suppressive adenosine by corresponding naturally occurring $T_{Reg}$ populations (in aspects, including natural $T_{Regs}$ and/or adaptive $T_{Regs}$). In other aspects, such stimulation can result in corresponding naturally occurring $T_{Reg}$ populations (in aspects, including natural $T_{Regs}$ and/or adaptive $T_{Regs}$) binding to and removing costimulatory molecules on dendritic cells, resulting the inhibition of dendritic cell function. Further, in aspects, such stimulation can result in $T_{Reg}$ induced upregulation of checkpoint molecules on dendritic cells and other cell populations, e.g. but not limited to endothelial cells, by corresponding naturally occurring $T_{Reg}$ populations (in aspects, including natural $T_{Regs}$ and/or adaptive $T_{Regs}$). In additional aspects, such stimulation can result in $T_{reg}$ stimulation of B-regulatory cells. B-regulatory cells ("B-regs") are cells that are responsible for the anti-inflammatory effect, that is characterized by the expression of CD1d, CDS, and the secretion of IL-10. B-regs are also identified by expression of Tim-1 and can be induced through Tim-1 ligation to promote tolerance. The ability of being B-regs was shown to be driven by many stimulatory factors such as toll-like receptors, CD40-ligand and others. However, full characterization of B-regs is ongoing. B-regs also express high levels of CD25, CD86, and TGF-β. The increased secretion of such regulatory cytokines and chemokines by regulatory T cells, as well as other activities described above, are hallmarks of regulatory T cells. In aspects, regulatory T cells activated by the Tregitope compositions of the present disclosure may express a CD4+CD25+FOXP3 phenotype. Regulatory T cells activated by the Tregitope compositions of the present disclosure directly suppress T-effector immune responses ex vivo as measured by decreased antigen-specific Th1- or Th2-associated cytokine levels, principally INF-γ, IL-4, and IL-5, and by decreased proliferation and/or effector function of antigen-specific T effector cells as measured by CFSE dilution and/or cytolytic activity. In aspects, regulatory T cells activated by the Tregitope compositions of the present disclosure directly suppress T effector immune responses in vivo as measured by decreased antigen-specific Th1- or Th2-associated cytokine levels (as measured by Elisa assay), decreased antigen-specific T effector cell levels (as measured by EliSpot assay), decreased cytolytic activity, and/or decreased antibody titers for protein antigens.

In aspects, natural regulatory T cells activated by the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) stimulate the development of adaptive $T_{Reg}$ cells. In aspects, co-incubating peripheral T cells with the Tregitope compositions of the present disclosure in the presence of antigen results in the expansion of antigen-specific CD4+/CD25+ T cells, upregulates the expression of the Foxp3 gene or Foxp3 protein in those cells and suppresses the activation of antigen-specific T effector cells in vitro. In aspects, the Tregitope compositions of the present disclosure may result in the activation and/or expansion of T regulatory type 1 (Tr1) cells. Tr1 cells have strong immunosuppressive capacity in several immune-mediated diseases (Roncarolo and Battaglia, 2007, Nat Rev Immunol 7, 585-598; Roncarolo et al., 2011, Immunol Rev 241, 145-163; Pot et al., 2011, Semin Immunol 23, 202-208). The secretion of high levels of IL-10, and the killing of myeloid antigen-presenting cells (APCs) via Granzyme B are the main mechanisms of Tr1-mediated suppression (Groux et al., 1997, Nature 389, 737-742; Magnani et al., 2011 Eur J Immunol 41, 1652-1662). Tr1 cells are distinguished from T helper ($T_H$)1, $T_H$2, and $T_H$17 cells by their unique cytokine profile and the regulatory function. Tr1 cells have been shown secrete higher levels of IL-10 than IL-4 and IL-17, the hallmark cytokines of $T_H$2 and $T_H$17 cells, respectively. Tr1 cells can also secrete low levels of IL-2 and, depending on the local cytokine milieu, can produce variable levels of IFN-γ, together, the key $T_H$1 cytokines (Roncarolo et al., 2011, Immunol Rev 241, 145-163). FOXP3 is not a biomarker for Tr1 cells since its expression is low and transient upon activation. IL-10-producing Tr1 cells express ICOS (Haringer et al., 2009, J Exp Med 206, 1009-1017) and PD-1 (Akdis et al., 2004, J Exp Med 199, 1567-1575), but these markers are not specific (Maynard et al., 2007, Nat Immunol 8, 931-941). CD49b, the a2 integrin subunit of the very-late-activation antigen (VLA)-2, has been proposed as a marker for IL-10-producing T cells (Charbonnier et al., 2006, J Immunol 177, 3806-3813); but it is also expressed by human $T_H17$ cells (Boisvert et al., 2010, Eur J Immunol 40, 2710-2719). Moreover, murine CD49$^+$ T cells secrete IL-10 (Charbonnier et al., 2006, J Immunol 177, 3806-3813) but also pro-inflammatory cytokines (Kassiotis et al., 2006, J Immunol 177, 968-975). Lymphocyte activation gene-3 (LAG-3), a CD4 homolog that binds with high affinity to MHC class II molecules, is expressed by murine IL-10-producing CD4$^+$ T cells (Okamura et al., 2009, Proc Natl Acad Sci USA 106, 13974-13979), but also by activated effector T cells (Workman and Vignali, 2005, J Immunol 174, 688-695; Bettini et al., 2011, J Immunol 187, 3493-3498; Bruniquel et al., 1998, Immunogenetics 48, 116-124; Lee et al., 2012, Nat Immunol 13, 991-999) and by FOXP3$^+$ regulatory T cells (Tregs) (Camisaschi et al., 2010, J Immunol 184, 6545-6551). It was recently shown that human Tr1 cells express CD226 (DNAM-1), which is involved in the specific killing of myeloid APCs (Magnani et al., 2011 Eur J Immunol 41, 1652-1662). In further aspects, Tregitope compositions of the present disclosure may result in the activation and/or expansion of TGF-β secreting Th3 cells, regulatory NKT cells, regulatory CD8$^+$ T cells, double negative regulatory T cells. "Th3 cells" refer to cells having the following phenotype CD4$^+$FoxP3$^+$ and capable of secreting high levels TGF-β upon activation, amounts of IL-4 and IL-10 and no IFN-γ or IL-2. These cells are TGF-β derived. "Regulatory NKT cells" refers to cells having the following phenotype at rest CD161$^+$CD56$^+$CD16$^+$ and a Vα24/Vβ11 TCR. "Regulatory CD8+ T cells" refers to cells having the following phenotype at rest CD8$^+$CD122$^+$ and capable of secreting highs levels of IL-10 upon activation. "Double negative regulatory T cells" refers to cells having the following phenotype at rest TCRαβ$^+$CD4$^-$CD8$^-$.

In aspects, the Tregitope compositions of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) are useful for regulating immune response to monoclonal antibodies, protein therapeutics, self-antigens promoting autoimmune response, allergens, transplanted tissues and in other applications where tolerance is the desired outcome. In aspects, the Tregitope compositions of the present disclosure are useful for regulating an immune response caused by Factor VIII supplements used to prevent or stop bleeding in patients suffering from Hemophilia A.

In aspects, the Tregitopes of the present disclosure can bind MHC class II molecules, engage TCR in context of MHC class II molecules and activate naturally occurring $T_{Regs}$ (in aspects, including natural $T_{Regs}$ and/or adaptive $T_{Regs}$).

Suppressing an Immune Response in a Subject in Need Thereof. In aspects, the present disclosure is directed to a method of stimulating, inducing, and/or expanding regulatory T-cells (in aspects, naturally occurring $T_{Regs}$, including natural $T_{Regs}$ and/or adaptive $T_{Regs}$) in a subject in need thereof and/or suppressing an immune response in a subject in need thereof by administering to the subject a therapeutically effect amount of a Tregitope composition (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) of the present disclosure.

In aspects, the present disclosure is directed to a method of stimulating/inducing, regulatory T-cells (e.g., naturally occurring $T_{Regs}$ (in aspects, including natural $T_{Regs}$ and/or adaptive $T_{Regs}$)) to suppress an immune response in a subject in need thereof by administering to the subject a therapeutically effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein). In aspects, the immune response is the result of one or more therapeutic treatments with at least one therapeutic protein, treatment with a vaccine (particularly in situations in which an adverse event results from the vaccination), or treatment with at least one antigen. In a particular embodiment, the immune response is the result of one or more therapeutic treatments with a Coagulation Factor VIII supplement. Thus, the administration of one or more Tregitope compositions of the present disclosure can be used to prevent the development of, or terminate, and already-established immune response to establish tolerance induction to Factor VIII (and Coagulation Factor VIII supplements) in patients suffering from Hemophilia A. In aspects, the instant disclosure provides methods of using a Tregitope composition of the present disclosure in combination with a therapeutic blood clotting protein (e.g., a Coagulation Factor VIII supplement) for the purpose of suppressing an immune response against the therapeutic blood clotting protein in a T-cell dependent manner. This combination may be administered with the Tregitope compositions of the present disclosure bound either covalently or non-covalently, or they may be administered as an admixture. In another aspect, the administration of a Tregitope composition of the present disclosure shifts one or more antigen presenting cells to a regulatory phenotype, one or more dendritic cells to a regulatory phenotype, decreases CD11c and HLA-DR expression in the dendritic cells or other antigen presenting cells.

In aspects, the present disclosure is directed to a method for repressing/suppressing an immune response in a subject, comprising administering a therapeutically effective amount of Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), wherein the Tregitope composition represses/suppresses the immune response. In aspects, the Tregitope composition represses/suppresses an innate immune response. In aspects, the Tregitope composition represses/suppresses an adaptive immune response. In aspects, the Tregitope composition represses/suppresses an effector T cell response. In aspects, the Tregitope composition represses/suppresses a memory T cell response. In aspects, the Tregitope composition represses/suppresses helper T cell response. In aspects, the Tregitope composition represses/suppresses B cell response. In aspects, the Tregitope composition represses/suppresses a nkT cell response.

In aspects, the present invention is directed to a method of suppressing an immune response, specifically an antigen specific immune response in a subject, through the administration of a therapeutically effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), wherein said Tregitope composition activates naturally occurring $T_{Regs}$ (in aspects, including natural $T_{Regs}$ and/or adaptive $T_{Regs}$, and in aspects CD4$^+$/CD25$^+$/FoxP3$^+$ regulatory T-cells) or suppresses the activation of CD4$^+$ T-cells, the proliferation of CD4$^+$ and/or CD8$^+$ T-cells, and/or suppresses the activation or proliferation of β-cells or nkT Cells. In aspects, a Tregitope composition of the present disclosure may be either covalently bound, non-covalently bound, or in admixture with a specific target antigen. In particular aspects, one or more of e.g., isolated, synthetic, or recombinant isolated, synthetic, or recombinant polypeptides ($T_{reg}$ activating regulatory T-cell epitope, Tregitope, or T-cell epitope polypeptide) and/or chimeric or fusion polypeptide compositions of the presently disclosed Tregitope compositions may be either covalently bound, non-covalently bound, or in admixture with a specific target antigen. In aspects, an administered Tregitope composition of the present disclosure that is covalently bound, non-covalently bound, or in admixture with a specific target antigen results in the diminution of immune response against the target antigen.

In aspects, the target antigen may be an autologous protein or protein fragment. In aspects, the target antigen may be an allergen. In aspects, the target antigen may be an allogenic protein or protein fragments. In aspects, the target antigen may be a biologic medicine or fragments thereof. In aspects, the target antigen is a coagulation Factor VIII supplement. In aspects, the suppressive effect is mediated by natural $T_{Regs}$. In aspects, the suppressive effect is mediated by adaptive $T_{Regs}$. In aspects, the one or more Tregitopes included in the Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) suppresses an effector T cell response. In aspects, the one or more Tregitopes of the presently-disclosed Tregitope composition suppresses an innate immune response. In aspects, the one or more Tregitopes of the presently-disclosed Tregitope composition suppresses an adaptive immune response. In aspects, the one or more Tregitopes of the presently-disclosed Tregitope composition suppresses helper T cell response. In aspects, the one or more Tregitopes of the presently-disclosed Tregitope composition suppresses a memory T cell response. In aspects, the one or more Tregitopes of the presently-disclosed Tregitope composition suppresses β cell response. In aspects, the one or more Tregitopes of the presently-disclosed Tregitope composition suppresses nkT cell response.

Designing Small Molecule Therapeutics. In one aspect, the invention provides methods of using a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) for the purpose of designing small molecule therapeutics. In one aspect, Tregitope-specific T cells are stimulated three times with pools of small molecule mixtures at a concentration of 1 μg/ml and autologous dendritic cells (DC) at 2-week intervals, followed by stimulation with heterologous DC and antigens. T cells ($1.25 \times 10^5$) and DC ($0.25 \times 10^5$) are added per well in round-bottom, 96-well plates. T cell medium is made by supplementing 500 ml of RPMI medium 1640 with 50 ml of FCS (HyClone Laboratories, Inc., Logan, Utah), penicillin, and streptomycin (GIBCO Laboratories, Gaithersburg, Md.); 20 mM Hepes (GIBCO); and 4 ml 1 N NaOH solution. The IL-2 concentration is initially 0.1 nM and gradually is increased to 1 nM during subsequent rounds of stimulation. T cell clones are derived by limiting dilution by using 0.6×10⁵ Epstein—Barr virus-transformed B cells (100 Gray) and 1.3×10⁵ heterologous peripheral blood mononuclear cells (33 Gray) as feeder cells and 1 µg/ml Difco™ phytohemagglutinin (Bacterius Ltd, Houston, Tex.) in medium containing 2 nM IL-2. Small molecules pools that stimulate the Tregitope specific T cells are then tested as individual molecules.

Cloning T Cell Receptors. In aspects, the present disclosure provides methods of using a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) for the purpose of cloning T cell receptors. Cloning of Tregitope specific T cells can be conducted by techniques known to one of skill in the art. For example, isolated PBMCs are stimulated with Tregitopes at 10 µg/ml RPMI media containing 20% HSA. IL-2 is added (10 U/ml final concentration) every other day starting on day 5. T cells are stained with tetramer pools on day 11 or 12. For each pool, 2-3×10⁵ cells are incubated with 0.5 mg of PE-labeled tetramer in 50 ml of culture medium (10 mg/ml) at 37° C. for 1 to 2 h, and then stained with anti-CD4-FITC (BD PharMingen, San Diego, Calif.) for 15 min at room temperature. Cells are washed and analyzed with a Becton Dickinson FACSCalibur flow cytometer (Becton Dickinson, San Jose, Calif.). Tetramers loaded with the corresponding single peptides are generated for those pools that give positive staining, and analysis is done on day 14 or 15. Cells that are positive for a particular tetramer are single-cell sorted into 96-well U-bottom plates by using a Becton Dickinson FACSVantage (San Jose, Calif.) on the same or following day. Sorted cells are expanded with 1.5-3×10⁵ unmatched, irradiated (5000 rad) PBMC per well as feeders with 2.5 mg/ml PHA and 10 U/ml IL-2 added 24 h later. Specificity of cloned T cells is confirmed by staining with tetramers (loaded with cognate peptide or control peptide, HA307-319) and T cell proliferation assays with 10 mg/ml of specific peptide (Novak E J et al., J Immunol, 166(11): 6665-70, which is herein incorporated by reference in its entirety). In aspects, total RNA is extracted with an RNeasy Mini Kit (Qiagene, Hilden, Del.) from the Tregitope specific T cell lines generated as described above. One microgram of total RNA is used to clone the TCR cDNAs by a rapid amplification of cDNA end (RACE) method using aGeneRacer® kit (Invitrogen, Carlsbad, CA). Before synthesizing the single-strand cDNA, the RNA is de-phosphorylated, de-capped, and ligated with an RNA oligonucleotide according to the instruction manual of 5' RACE GeneRacer® kit. SuperScript II RT® (Life Technologies Corp, Carlebad, Calif.) and GeneRacer® Oligo-dT are used for reverse transcription of the RNA Oligo-ligated mRNA to single-strand cDNAs. 5' RACE is performed by using GeneRacer® 5' (GeneRacer® Kit) as 5' primer and gene-specific primer TCRCAR (5'-GTT AAC TAG TTC AGC TGG ACC ACA GCC GCA GC-3'; SEQ ID NO: 65) or TCRCB1R (5'- CGG GTT AAC TAG TTC AGA AAT CCT TTC TCT TGA CCA TGG C-3'; SEQ ID NO: 66), or TCRCBR2 (5'-CTA GCC TCT GGA ATC CTT TCT CTT G-3'; SEQ ID NO: 67) as 3' primers for TCR α, β1, or β2 chains, respectively. The polymerase chain reaction (PCR) products are cloned into pCR2.1 TOPO vector (Invitrogen, Carlsbad, Calif.) and then transformed into One Shot TOP10 Competent Escherichia coli (Invitrogen, Carlsbad, Calif.). Plasmid DNAs are prepared from 96 individual clones from each construct for TCRα, β1, and β2 chains. Full-length insert of all the plasmids is sequenced to determine the vα/vβ usage (Zhao Y et al., (2006), J Immunother, 29(4):398-406, herein incorporated by reference in its entirety).

Methods of Preventing or Treating a Medical Condition

The present invention is directed to, for example methods of preventing or treating one or more medical conditions in a subject comprising administering a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and preventing or treating the medical condition in a subject by said step of administering. The medical condition can be, for example, primary immunodeficiencies (such as autoimmunity associated with primary immune deficiency disorders); immune-mediated thrombocytopenia, Kawasaki disease, hematopoietic stem cell transplantation in patients older than 20 years, chronic B-cell lymphocytic leukemia and pediatric HIV type 1 infections. Specific examples include: (Hematology) aplastic anemia, pure red cell aplasia, Diamond-Blackfan anemia, autoimmune hemolytic anemia, hemolytic disease of the newborn, acquired factor VIII inhibitors, acquired von Willebrand disease, immune-mediated neutropenia, refractoriness to platelet transfusion, neonatal alloimmune/autoimmune thrombocytopenia, posttransfusion purpura, thrombotic thrombocytopenia purpura/hemolytic uremic syndrome; (Infectious diseases), solid organ transplantation, surgery, trauma, burns, and HIV infection; (Neurology) epilepsy and pediatric intractable Guillain-Barré syndrome, chronic inflammatory demyelinating polyneuropathy, myasthenia gravis, Lambert-Eaton myasthenic syndrome, multifocal motor neuropathy, multiple sclerosis; (Obstetrics) recurrent pregnancy loss; (Pulmonology) asthma, chronic chest symptoms, rheumatology, rheumatoid arthritis (adult and juvenile), systemic lupus erythematosus, systemic vasculitides, dermatomyositis, polymyositis, inclusion-body myositis, wegener granulomatosis; (Miscellaneous) adrenoleukodystrophy, amyotrophic lateral sclerosis, Behçet syndrome, acute cardiomyopathy, chronic fatigue syndrome, congenital heart block, cystic fibrosis, autoimmune blistering dermatosis, diabetes mellitus, acute idiopathic dysautonomia, acute disseminated encephalomyelitis, endotoxemia, hemolytic transfusion reaction, hemophagocytic syndrome, acute lymphoblastic leukemia, lower motor neuron syndrome, multiple myeloma, human T-cell lymphotrophic virus-1-associated myelopathy, nephritic syndrome, membranous nephropathy, nephrotic syndrome, euthyroid ophthalmopathy, opsoclonus-myoclonus, recurrent otitis media, paraneoplastic cerebellar degeneration, paraproteinemic neuropathy, parvovirus infection (general), polyneuropathy, organomegaly, endocrinopathy, M-protein, and skin changes (POEMS) syndrome, progressive lumbosacral plexopathy, lyme radiculoneuritis, Rasmussen syndrome, Reiter syndrome, acute renal failure, thrombocytopenia (nonimmune), streptococcal toxic shock syndrome, uveitis and Vogt-Koyanagi-Harada syndrome.

In a particular embodiment, the present invention is directed to, for example, methods of treating allergy, autoimmune disease, transplant-related disorders such as graft versus host disease, enzyme or protein deficiency disorders, hemostatic disorders (e.g., Hemophilia A, B, or C), cancers (particularly tumor associated autoimmunity), infertility, or infections (viral, bacterial, or parasitic). The Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can be used with in conjunction with other proteins or compounds used for treating a subject with a medical condition in order to reduce adverse events or enhance the efficacy of the co-administered compound.

Application to Preventing or Treating an Antibody and/or CD4+ T cell Response Caused by Factor VIII Supplements used to Prevent or Stop Bleeding in Patients Suffering from Hemophilia A. Hemophilia is a disease characterized by excessive bleeding after a cut or injury. The cause of this excessive bleeding is failure for blood to clot properly in patients with hemophilia. Hemophilia is a genetic disorder, which means it's the result of a change in genes that was either inherited (passed on from parent to child) or happened during development in the womb. Bleeding can be external or internal. Internal bleeding of the joints (like the knees or hips) is common in children with hemophilia. Hemophilia mostly affects boys—about 1 in every 5,000-10,000. Girls who inherit the gene rarely get the condition, but as carriers of the gene they can pass it to their children.

When an injury results in bleeding, platelets begin the clotting process. Platelets release chemicals that attract additional platelets as well as activating proteins in the blood known as clotting factors, in humans, these are known as human coagulation Factors I through XIII. These proteins mix with the platelets to form fibers, which strengthen the clot and stop the bleeding. Patients suffering from hemophilia fail to produce sufficient amounts of the clotting factor that work together to clot blood. Hemophilia results from a patient being unable to produce enough Factor VIII or Factor IX to clot blood.

There are two major kinds of hemophilia: hemophilia A and hemophilia B. About 80% of cases are hemophilia A, which is a Factor VIII deficiency, hemophilia B and C occur when the body produces too little Factor IX. Hemophilia can be mild, moderate, or severe, based on the amount of the clotting factor in the blood:

Mild hemophilia: the body makes 6% to 50% of the affected clotting factor

Moderate hemophilia: the body makes 2% to 5% of the affected clotting factor

Severe hemophilia: the body makes less than 1% of the affected clotting factor In general, a patient with milder hemophilia may bleed too much only once in a while. A patient with severe hemophilia is at risk for bleeding problems much more often.

Hemophilia is a lifelong condition with no cure other than liver transplantation, a procedure that can sometimes cause health problems more serious than hemophilia itself.

Factor VIII replacement therapy helps blood to clot and prevents long-term joint damage due to bleeding. It may be administered while a bleeding episode is happening to promote clotting, or in regularly scheduled treatments to keep the blood healthy. The therapy is "infused" in the blood—given through an intravenous (IV) line either at a clinic or at home by a visiting nurse or by parents (and patients themselves) who have had training to administer this therapy. Once the clotting factor is in the blood, it begins to work quickly.

Human patients suffering from Hemophilia A, however, frequently mount an antibody response against the coagulation Factor VIII supplements prescribed to prevent or stop bleeding episodes. A patient's body views the new clotting factor as foreign and develops antibodies that block its clotting action. About a quarter of children with severe Hemophilia A develop antibodies to the clotting factor. These antibodies can make the hemophilia difficult to treat because these antibody responses diminish the efficacy of the Factor VIII treatments leading to further complications, such as severe adverse bleeding episodes and arthritis.

One strategy both for the prevention and therapy of an unwanted antibody and/or CD4+ T cell response caused by Factor VIII supplements used to prevent or stop bleeding in patients suffering from Hemophilia A is the induction of regulatory T cells. Hemophiliacs can be protected from developing an unwanted immune response when receiving Factor VIII supplements. In aspects, the present invention is directed to preventing or diminishing an autoimmune response caused by human coagulation Factor VIII supplements used to prevent or stop bleeding in patients suffering from Hemophilia A comprising administering a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), thereby treating the medical condition. The Tregitope compositions of the invention can be used with or in conjunction with other proteins or compounds (e.g., but not limited to, human coagulation Factor VIII supplements) used for treating a subject with a medical condition (e.g., but not limited to Hemophilia A) in order to reduce adverse events or enhance the efficacy of the co-administered compound.

Application to Allergy. Allergen-specific regulatory T cells play an important role in controlling the development of allergy and asthma. Naturally occurring $T_{Regs}$ (in aspects, including natural $T_{Regs}$ and/or adaptive $T_{Regs}$, and in aspects CD4⁺/CD25⁺/FoxP3⁺ regulatory T-cells) have been shown to inhibit the inappropriate immune responses involved in allergic diseases. A number of recent studies indicate that regulatory T cells play an important role in controlling the overdevelopment of T-helper type 2 biased immune responses in susceptible individuals, not only in animal models, but in humans as well. Recent studies indicate that $T_{regs}$ also suppress T cell co-stimulation by the secretion of TGF-β and IL-10, suggesting an important role of $T_{regs}$ in the regulation of allergic disorders. Impaired expansion of natural or adaptive regulatory T cells leads to the development of allergy, and treatment to induce allergen-specific $T_{regs}$ would provide curative therapies for allergy and asthma. One strategy both for the prevention and therapy of asthma is the induction of $T_{regs}$. Animals can be protected from developing asthma by immune stimulation leading to Th1 or $T_{reg}$ responses. Accordingly, Tregitope compositions of the present disclosure are useful in methods for the prevention or treatment of allergy and/or asthma. As such, in aspects, the present disclosure is directed to a method of preventing or treating allergy and/or asthma in a subject, the method comprising administering a therapeutically-effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and preventing or treating allergy and/or asthma in a subject by said step of administering.

Application to Transplantation. The Tregitope compositions of the present disclosure are useful to induce tolerance during the transplantation process, by promoting the development of cells that specifically down regulate immune responses against donor cells. Induction of Ag-specific $T_{Reg}$ cells for treating organ-specific autoimmunity is an important therapeutic development, avoiding generalized immune suppression. In murine models of bone marrow transplantation, $T_{Regs}$ promote donor bone marrow engraftment and decrease the incidence and severity of graft versus host disease without abrogating the beneficial graft versus tumor immunologic effect. These findings, in concert with observations that $T_{Regs}$ in mice and humans share phenotypic and functional characteristics, have led to active investigations into the use of these cells to decrease complications associated with human hematopoietic cell transplantation. An imbalance of $T_{Regs}$ and effector T cells contributes to the development of graft versus host disease, however, the mechanisms of immunoregulation, in particular, the allorecognition properties of $T_{Regs}$, their effects on and interaction with other immune cells, and their sites of suppressive activity, are not well understood.

Accumulating evidence from both humans and experimental animal models has implicated the involvement of $T_{Regs}$ in the development of graft versus host disease (GVHD). The demonstration that $T_{Regs}$ can separate GVHD from graft versus tumor (GVT) activity suggests that their immunosuppressive potential could be manipulated to reduce GVHD without detrimental consequence on GVT effect. Although a variety of T lymphocytes with suppressive capabilities have been reported, the two best-characterized subsets are the naturally arising, intrathymic-generated $T_{Regs}$ (natural $T_{Regs}$) and the peripherally generated, adaptive $T_{Regs}$ (adaptive $T_{Regs}$). Accordingly, Tregitope compositions of the present disclosure are useful in methods for inducing tolerance during the transplantation process. As such, in aspects, the present disclosure is directed to a method of inducing tolerance during the transplantation process in a subject, the method comprising administering a therapeutically-effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and inducing tolerance during the transplantation process in a subject by said step of administering.

Application as a Tolerizing Agent and to Autoimmunity. In aspects, Tregitope compositions of the present disclosure can be used as a tolerizing agents for immunogenic compounds (protein therapeutics) (Weber Calif. et al., (2009), Adv Drug Deliv, 61(11):965-76). This discovery has implications for the design of protein therapeutics. Thus, administration of a monoclonal antibody, autologous cytokine, or foreign protein in conjunction with a Tregitope composition of the present disclosure suppresses adverse T effector immune responses. In vivo, $T_{Regs}$ act through dendritic cells to limit autoreactive T-cell activation, thus preventing their differentiation and acquisition of effector functions. By limiting the supply of activated pathogenic cells, $T_{Regs}$ prevent or slow down the progression of autoimmune diseases. This protective mechanism appears, however, insufficient in autoimmune individuals, likely because of a shortage of $T_{Regs}$ cells and/or the development and accumulation of $T_{Reg}$-resistant pathogenic T cells over the long disease course. Thus, restoration of self-tolerance in these patients may require purging of pathogenic T cells along with infusion of $T_{Regs}$ with increased ability to control ongoing tissue injury. Organ-specific autoimmune conditions, such as thyroiditis and insulin-dependent diabetes mellitus have been attributed to a breakdown of this tolerance mechanism (Mudd Pa. et al., (2006), Scand J Immunol, 64(3):211-8). Accordingly, Tregitope compositions of the present disclosure are useful in methods for the prevention or treatment of autoimmunity. As such, in aspects, the present disclosure is directed to a method of preventing or treating autoimmunity in a subject, the method comprising administering a therapeutically-effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and preventing or treating autoimmunity in a subject by said step of administering.

Application to Diabetes. Type 1 (juvenile) diabetes is an organ-specific autoimmune disease resulting from destruction of insulin-producing pancreatic beta-cells. In non-diabetics, islet cell antigen-specific T cells are either deleted in thymic development or are converted to T regulatory cells that actively suppress effector responses to islet cell antigens. In juvenile diabetics and in the NOD mouse model of juvenile diabetes, these tolerance mechanisms are missing. In their absence, islet cell antigens are presented by human leukocyte antigen (HLA) class I and II molecules and are recognized by CD8(+) and CD4(+) auto-reactive T cells. Destruction of islet cells by these auto-reactive cells eventually leads to glucose intolerance. Co-administration of Tregitopes and islet cell antigens leads to the activation of naturally occurring T regulatory cells and the conversion of existing antigen specific effector T cell to a regulatory phenotype. In this way, deleterious autoimmune response is redirected leading to the induction of antigen-specific adaptive tolerance. Modulation of auto-immune responses to autologous epitopes by induction of antigen-specific tolerance can prevent ongoing beta-cell destruction. Accordingly, Tregitope compositions of the present disclosure are useful in methods for the prevention or treatment of diabetes. As such, in aspects, the present disclosure is directed to a method of preventing or treating diabetes in a subject, the method comprising administering a therapeutically-effective amount of Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and preventing or treating diabetes in a subject by said step of administering.

Application to Hepatitus B (HBV) infection. Chronic HBV is usually either acquired (by maternal fetal transmission) or can be a rare outcome of acute HBV infection in adults. Acute exacerbations of chronic hepatitis B (CH-B) are accompanied by increased cytotoxic T cell responses to hepatitis B core and e antigens (HBcAg/HBeAg). In a recent study, the SYFPEITHI T cell epitope mapping system was used to predict MHC class II-restricted epitope peptides from the HBcAg and HbeAg (Feng IC et al., (2007), J Biomed Sci, 14(1):43-57). MHC class II tetramers using the high scoring peptides were constructed and used to measure $T_{Reg}$ and CTL frequencies. The results showed that $T_{Reg}$ cells specific for HBcAg declined during exacerbations accompanied by an increase in HBcAg peptide-specific cytotoxic T cells. During the tolerance phase, FOXp3-expressing $T_{Reg}$ cell clones were identified. These data suggest that the decline of HbcAg $T_{Reg}$ T cells accounts for the spontaneous exacerbations on the natural history of chronic hepatitis B virus infection. Accordingly, Tregitope compositions of the present disclosure are useful in methods for the prevention or treatment of viral infections. As such, in aspects, the present disclosure is directed to a method of preventing or treating a viral infection (e.g., HBV infection) in a subject, the method comprising administering a therapeutically-effective amount of a Tregitope composition of the present disclosure ((including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), and preventing or treating said viral infection in a subject by said step of administering.

Application to SLE. A $T_{Reg}$ epitope that plays a role in Systemic Lupus Erythematosis (SLE) or Sjögren's syndrome has been defined. This peptide encompasses residues 131-151 (RIHMVYSKRSGKPRGYAFIEY; SEQ ID NO: 68) of the spliceosome protein. Binding assays with soluble HLA class II molecules and molecular modeling experiments indicated that the epitope behaves as promiscuous epitope and binds to a large panel of human DR molecules. In contrast to normal T cells and T cells from non-lupus autoimmune patients, PBMCs from 40% of randomly selected lupus patients contain T cells that proliferate in response to peptide 131-151. Alteration of the ligand modified the T cell response, suggesting that several populations of T cells responding to this peptide exist, among which may be $T_{Reg}$ cells. T regulatory epitopes have also been defined in Sjögren's syndrome. Accordingly, Tregitope compositions of the present disclosure administered in combination with the Tregitope of SEQ ID NO: 68 are useful in methods for the prevention or treatment of SLE. As such, in aspects, the present disclosure is directed to a method of preventing or treating SLE in a subject, the method comprising administering a therapeutically-effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) in combination with the Tregitope of SEQ ID NO: 68, and preventing or treating SLE in a subject by said step of administering.

Application to Autoimmune Thyroiditis. Autoimmune Thyroiditis is a condition that occurs when antibodies arise to self-thyroid peroxidase and/or thyroglobulin, which cause the gradual destruction of follicles in the thyroid gland. HLA DR5 is closely associated with the disease. Accordingly, Tregitope compositions of the present disclosure administered in combination with thyroid peroxidase and/or thyroglobulin TSHR or portions thereof are useful in methods for the prevention or treatment of autoimmune thyroiditis. As such, in aspects, the present disclosure is directed to a method of preventing or treating autoimmune thyroiditis in a subject, the method comprising administering a therapeutically-effective amount of a Tregitope composition of the present disclosure ((including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) in combination with thyroid peroxidase and/or thyroglobulin TSHR or portions thereof, and preventing or treating autoimmune thyroiditis in a subject by said step of administering. In further aspects, Tregitope compositions of the present disclosure administered in combination with TSHR or other Graves' disease antigens or portions thereof are useful in methods for the prevention or treatment of Grave's disease. Graves' disease is an autoimmune disorder that is characterized by antibodies to self-thyroid stimulating hormone receptor (TSHR) leading to leading to hyperthyroidism, or an abnormally strong release of hormones from the thyroid gland. Several genetic factors can influence susceptibility to Graves' disease. Females are much more likely to contract the disease than males; White and Asian populations are at higher risk than black populations and HLA DRB1-0301 is closely associated with the disease. As such, in aspects, the present disclosure is directed to a method of preventing or treating Grave's disease in a subject, the method comprising administering a therapeutically-effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) in combination with TSHR or other Graves' disease antigens or portions thereof, and preventing or treating Grave's disease in a subject by said step of administering.

Ex Vivo Expansion and/or Stimulation of T-Regulatory Cells Using Tregitope Compositions. In aspects, the present disclosure provides ex vivo methods for the expansion of regulatory T-cells. In one embodiment, the invention provides a method of expanding regulatory T-cells in a biological sample, the method comprising: (a) providing a biological sample from a subject; (b) isolating regulatory T-cells from the biological sample; and contacting the isolated regulatory T-cells with an effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) under conditions wherein the T-regulatory cells increase in number to yield an expanded regulatory T-cells, thereby expanding the regulatory T-cells in the biological sample. In aspects, the method further comprises the step of administration of the expanded regulatory T-cells to a subject. In aspects, the subject administered the expanded regulatory T-cells is the same individual from which the original biological sample was obtained, e.g., by autologous transplantation of the expanded Tregitope (Ruitenberg J J et aL, (2006), BMC Immunol, 7:11).

In aspects, the present disclosure provides ex vivo methods for stimulation of regulatory T-cells in a biological sample, the method comprising: (a) providing a biological sample from a subject; (b) isolating regulatory T-cells from the biological sample; and contacting the isolated regulatory T-cells with an effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) under conditions wherein the T-regulatory cells are stimulated to alter one or more biological function, thereby stimulating the regulatory T-cells in the biological sample. In aspects, the method further comprises the step of administration of the stimulated regulatory T-cells to a subject. In aspects, the subject administered the stimulated regulatory T-cells is the same individual from which the original biological sample was obtained, e.g., by autologous transplantation of the expanded Tregitope.

Ex Vivo Pulsing of Antigen Presenting Cells using Tregitope Compositions. In aspects, the present disclosure provides ex vivo methods for antigen presenting cells (e.g., dendritic cells, macrophages, etc.) in a biological sample, the method comprising: (a) providing a biological sample from a subject; (b) isolating antigen presenting cells from the biological sample; and contacting the isolated antigen presenting with an effective amount of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) under conditions wherein the antigen presenting cells are stimulated to alter one or more biological function (e.g., to present the Tregitopes and/or skew the antigen presenting cells to a be tolerogenic (which in aspects can further include cytokine treatment of the antigen presenting cells to induce such a tolerogenic state), thereby stimulating the antigen presenting cells in the biological sample. In aspects, the method further comprises the step of administration of the stimulated antigen presenting cells to a subject. In aspects, the subject administered the stimulated antigen presenting cells is the same individual from which the original biological sample was obtained, e.g., by autologous transplantation of the stimulated antigen presenting cells.

In Vitro Uses of Tregitope Compositions. In aspects, the present disclosure provides the use of a Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) as reagents in the study of regulatory T-cell function in in vitro studies and experimental models.

Kits. The methods described herein can be performed, e.g., by utilizing pre-packaged kits comprising at least one Tregitope composition of the present disclosure (including one or more of e.g., polypeptides (which may be termed herein as "$T_{reg}$ activating regulatory T-cell epitope", "Tregitope", or "T-cell epitope polypeptide") having a sequence comprising, consisting of, or consisting essentially of one or more of SEQ ID NOS: 1-14 (in aspects, the polypeptides may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein), which can be conveniently used, e.g., in clinical settings to treat subjects exhibiting symptoms or family history of a medical condition described herein. In one embodiment, the kit further comprises instructions for use of the at least one Tregitope composition of the instant disclosure to treat subjects exhibiting symptoms or family history of a medical condition described herein.

Exemplification

The examples that follow are not to be construed as limiting the scope of the invention in any manner. In light of the present disclosure, numerous embodiments within the scope of the claims will be apparent to those of ordinary skill in the art.

(1) In-Silico Identification of a Tregitope Composition

T cells specifically recognize epitopes presented by antigen presenting cells (APCs) in the context of MHC (Major Histocompatibility Complex) Class II molecules. These T-helper epitopes can be represented as linear sequences comprising 7 to 30 contiguous amino acids that fit into the MHC Class II binding groove. A number of computer algorithms have been developed and used for detecting Class II epitopes within protein molecules of various origins (De Groot A S et al., (1997), AIDS Res Hum Retroviruses, 13(7):539-41; Schafer J R et al., (1998), Vaccine, 16(19): 1880-4; De Groot A S et. al., (2001), Vaccine, 19(31):4385-95; De Groot A S et al., (2003), Vaccine, 21(27-30):4486-504). These "in silico" predictions of T-helper epitopes have been successfully applied to the design of vaccines and the de-immunization of therapeutic proteins, i.e. antibody-based drugs, Fc fusion proteins, anticoagulants, blood factors, bone morphogenetic proteins, engineered protein scaffolds, enzymes, growth factors, hormones, interferons, interleukins, and thrombolytics (Dimitrov D S, (2012), Methods Mol Biol, 899:1-26). The preferred "therapeutic protein" of the instant invention is human Coagulation Factor VII or Factor VIII.

The EpiMatrix™ system (EpiVax, Providence, R.I.) is a set of predictive algorithms encoded into computer programs useful for predicting class I and class II HLA ligands and T cell epitopes. The EpiMatrix™ system uses 20×9 coefficient matrices in order to model the interaction between specific amino acids (20) and binding positions within the HLA molecule (9). In order to identify putative T cell epitopes resident within any given input protein, the EpiMatrix™ System first parses the input protein into a set of overlapping 9-mer frames where each frame overlaps the last by eight amino acids. Each frame is then scored for predicted affinity to one or more common alleles of the human HLA molecule; typically DRB1*0101, DRB1*0301, DRB1*0401, DRB1*0701, DRB1*0801, DRB1*1101, DRB1*1301, and DRB1*1501 (Mack et al., (2013), Tiss Antig, 81(4):194-203). Briefly, for any given 9-mer peptide specific amino acid codes (one for each of 20 naturally occurring amino acids) and relative binding positions (1-9) are used to select coefficients from the predictive matrix. Individual coefficients are derived using a proprietary method similar to, but not identical to, the pocket profile method first developed by Sturniolo (Sturniolo T et al., 1999, Nat Biotechnol, 17(6):555-61, herein incorporated by reference in its entirety). Individual coefficients are then summed to produce a raw score. EpiMatrix™ raw scores are then normalized with respect to a score distribution derived from a very large set of randomly generated peptide sequences. The resulting "Z" scores are normally distributed and directly comparable across alleles.

EpiMatrix™ peptide scoring. It was determined that any peptide scoring above 1.64 on the EpiMatrix™ "Z" scale (approximately the top 5% of any given peptide set) has a significant chance of binding to the MHC molecule for which it was predicted. Peptides scoring above 2.32 on the scale (the top 1%) are extremely likely to bind; most published T cell epitopes fall within this range of scores. Previous studies have also demonstrated that EpiMatrix™ accurately predicts published MHC ligands and T cell epitopes (De Groot A S, Martin W. Reducing risk, improving outcomes: bioengineering less immunogenic protein therapeutics. Clin Immunol. 2009 May; 131(2):189-201.doi: 10.1016/j.clim.2009.01.009. Epub 2009 Mar 6., herein incorporated by reference in its entirety).

Identification of promiscuous T cell Epitope Clusters. Potential T cell epitopes are not randomly distributed throughout protein sequences but instead tend to "cluster." T cell epitope "clusters" range from 9 to roughly 30 amino acids in length and, considering their affinity to multiple alleles and across multiple frames, contain anywhere from 4 to 40 binding motifs. Following epitope mapping, the result set produced by the EpiMatrix™ algorithm is screened for the presence of T cell epitope clusters and EpiBars™ by using a proprietary algorithm known as Clustimer™. Briefly, the EpiMatrix™ scores of each 9-mer peptide analyzed are aggregated and checked against a statistically derived threshold value. High scoring 9mers are then extended one amino acid at a time. The scores of the extended sequences are then re-aggregated and compared to a revised threshold value. The process is repeated until the proposed extension no longer improves the overall score of the cluster. Tregitope(s) identified in the present studies were identified by the Clustimer-™ algorithm as T cell epitope clusters. They contain significant numbers of putative T cell epitopes and EpiBars™ indicating a high potential for MHC binding and T cell reactivity.

Example 1. Identification of a Tregitope Composition

Hemophiliac patients produce truncated or mutated Factor VIII (FVIII) proteins or no FVIII protein at all. As a result, therapeutic FVIII is sometimes recognized as "foreign" by the immune system of patients suffering from hemophilia; resulting in the activation of FVIII specific CD4+ T cells and the development of anti-FVIII antibodies. This "Anti-Drug Antibody" response occurs in 25-30% of Hemophilia A patients treated with recombinant FVIII, increasing morbidity and lowering the quality of life (Waters B and Lillicrap D, (2009), J Thromb Haemost, 7(9):1446-56, herein incorporated by reference in its entirety).

FVIII and Factor V (FV) are homologous glycoproteins that are cofactors for proteolytic activation in the coagulation cascade. They share a conserved domain structure of (A1-A2-B-A3-C1-C2) and also share 35% amino acid identity in the A and C domains (Pipe SW et al., J Biol Chem, 273(14):8537-44, herein incorporated by reference in its entirety). Regulatory T cells ($T_{Reg}$), recognizing regulatory T cell epitopes (Tregitopes) present in the amino acid sequence of FV, cross react with homologous regulatory T cell epitopes present in the amino acid sequence of FVIII. Tregitopes derived from FV may be useful for the purpose of suppressing anti-therapeutic immune response targeting FVIII, particularly in FVIII deficient hemophiliacs.

9-mer peptides present in FV which are ligands to HLA DRB1*1501 (a known risk factor for hemophilia) and which can be related to homologous sequences present in FVIII provided said FVIII-derived homologues are also putative ligands to DRB1*1501 and at least four of the five T cell receptor (TCR) contact residues present in those peptides (relative positions 2, 3, 5, 7, and 8) are shared between the FV-derived putative epitope and its FVIII-derived homologue were identified. The complete amino acid sequence of human FV (Genbank accession: NP_000121.2) was parsed into overlapping 9-mer frames and scored using the EpiMatrix™ system as described previously. The complete amino acid sequence of human FVIII (Genbank accession: NP_000123.1) was parsed into overlapping 9-mer frames and scored using the EpiMatrix™ system as described previously.

A purpose built computer program was used to screen putative DRB1*1501 ligands derived from FV against a set of putative DRB1*1501 ligands derived from FVIII. Ten of the putative epitopes identified in FV were matched to TCR homologues in FVIII. Each of the FV-derived ligands and its FVIII-derived homologue(s) were then screened against the Immune Epitope database (IEDB) (National Institute of Allergy and Infectious Diseases (NIAID) Bethesda, MD) by conventional means in order to identify any previously validated epitopes present in the experimental set. The results of in-silico analysis are presented in FIG. 20. Three peptides were eliminated from further consideration due to the presence of a poor P1 binding anchor in either the FV derived peptide or the FVIII-derived homologue: SEQ ID NO: 3, FV 932 (SEQ ID NO: 32 and extended peptide SEQ ID NO: 33), and FV 2188 (SEQ ID NO: 50 and extended peptide SEQ ID NO 51). Two additional peptides were eliminated due to poor conservation within the murine versions of FV and/or FVIII; suggesting use in animal based models would be problematic: FV 179 (SEQ ID NO: 16 and extended peptide SEQ ID NO 17) and FV 2130 (SEQ ID NO: 46 and extended peptide SEQ ID NO 47). Peptide FV 1660 (SEQ ID NO: 36 and extended peptide SEQ ID NO 37) was eliminated due to its close homology to a previously selected peptide FV 435 (SEQ ID NO: 3 and extended peptide SEQ ID NO: 10). The remaining four peptides were selected for further testing. In order to ensure a high affinity bond between peptide ligands and Class II HLA, 9-mer peptides must be extended to include n- and c-terminal "flanks" of at least 2 to 3 amino acids in length. Three amino acids to the n- and c-terminal flanks of each of the four peptides were selected for further analysis. The synthesized peptides are designated SEQ ID NO: 1 (ILTIHFTGHSFIYGK); SEQ ID NO: 2 (IHSIHFSGHVFTVRK); SEQ ID NO: 3 (KIVFKNMASRPYSIY); SEQ ID NO: 5 (ESNIMSTINGYVPES); and SEQ ID NO: 7 (SHEFHAINGMIYSLP).

In a second analysis, FV-FVIII peptide pairs matched at all five TCR contact positions were identified. High EpiMatrix™ Z-scores for HLA DRB1*1501 were not required. The only requirement was that both peptides in a given pair score high for at least one matched DRB1 allele. The returned peptides sets are presented in FIG. 21. Based on this analysis, two additional peptides were selected for further testing: SEQ ID NO: 4 (FAVFDENKSWYLEDN) and SEQ ID NO: 6 (EKDIHSGLIGPLLI).

(2) Methods for the Assessment of Tregitope Binding to Soluble MHC.

Synthesis of peptides. The Tregitopes of the invention can be produced by direct chemical synthesis or by recombinant methods (J Sambrook et al., Molecular Cloning: A Laboratory Manual, ($2^{ED}$, 1989), Cold Spring Harbor Laboratory Press, Cold Springs Harbor, NY (Publ), herein incorporated by reference in its entirety). Sample Tregitopes were prepared using Fmoc-chemical (9-fluoronylmethoxycarbonyl synthesis, under the guidance and direction of the Inventors of the present invention at $21^{st}$ Century Biochemicals (Marlborough, Mass.). In certain aspects, the Tregitopes were capped with an n-terminal acetyl and c-terminal amino group. HPLC, mass spectrometry and UV scan (ensuring purity, mass and spectrum, respectively) analysis of the selected Tregitopes indicated >80% purity.

An amino acid analysis of SEQ ID NO:1 ILTIHFTGHSFIYGK was conducted by a third-party contractor (New England Peptide, Inc., Gardner, Mass.) confirming the predicted composition (data not shown).

Mass Spectrum and Analytical HPLC analysis was performed by a second independent contractor ($21^{St}$ Century Biochemicals, Inc., Marlboro, Mass.) further confirming the composition of the Tregitope (data not shown).

Figure 1D:
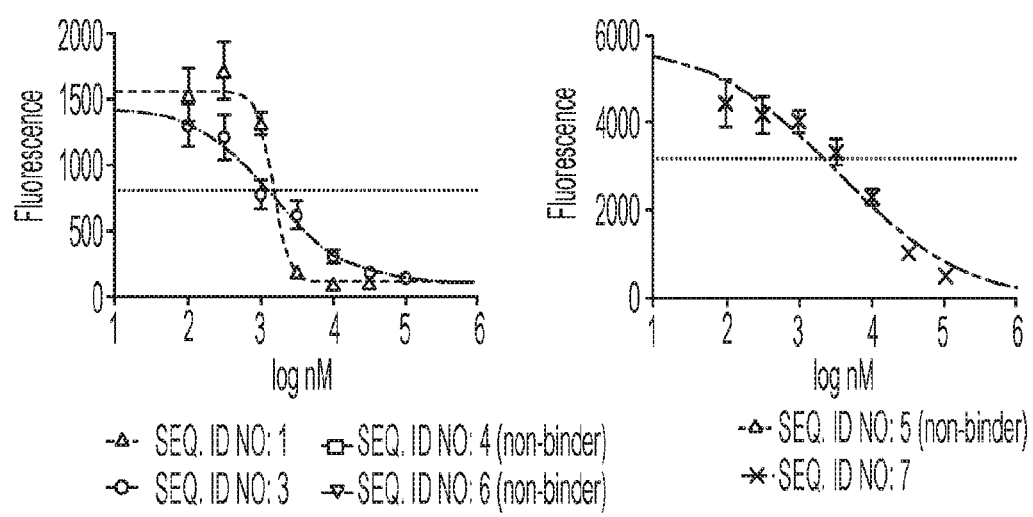
Figure 1E:
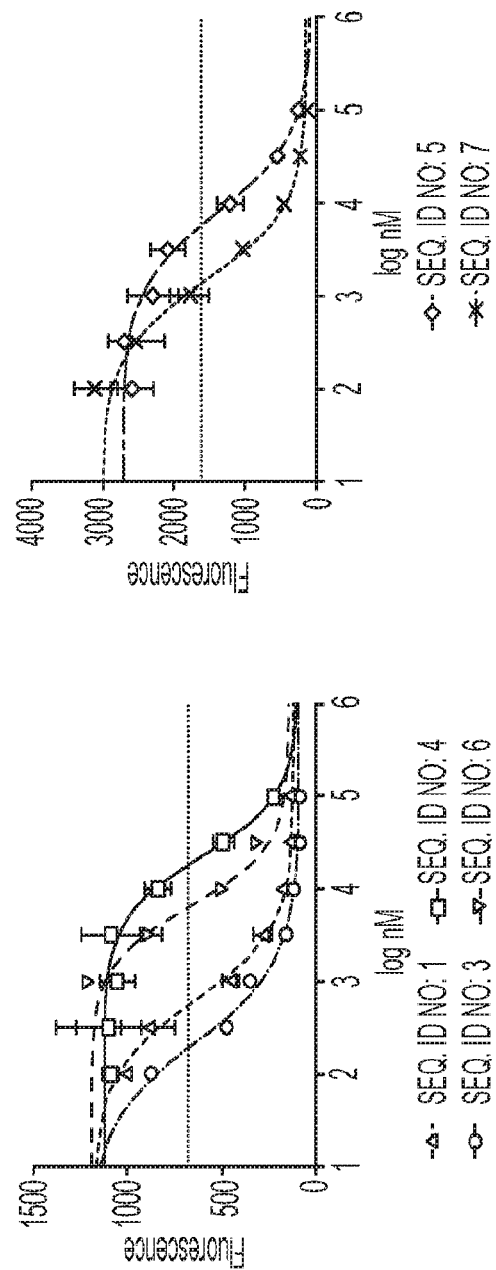

HLA Binding Assay. Binding activity was analyzed at EpiVax (Providence, R.I.). The binding assay used (Steere A C et al., (2006), J Exp Med, 2003(4):961-71) yielded an indirect measure of peptide-MHC affinity. Soluble HLA molecules were loaded onto a 96-well plate with the unlabeled experimental Tregitopes and labeled control peptide. Once the binding mixture reached steady equilibrium (at 24 hours), the HLA-Tregitope complexes were captured on an ELISA plate coated with anti-human DR antibody and detected with a Europium-linked probe for the label (PerkinElmer, Waltham, Mass.). Time-resolved fluorescence measuring bound labeled control peptide is assessed by a Specthe results for the HLA DRB1 *0301 assay. FIG. 1C summarizes the results for the HLA DRB1 *0701 assay for the selected FV peptides, FIG. 1D summarizes the results for HLA DRB1 *1101 assay for selected FV peptides, and FIG. 1E report summarizes the results for HLA DRB1* 1501.

TABLE 1

Peptides Selected for HLA Binding

| | | Max EPX Score for HLA DRB1 | | | | |
|---|---|---|---|---|---|---|
| Peptide ID | Peptide Sequence | *0101 | *0301 | *0701 | *1101 | *1501 |
| SEQ ID NO: 1 | ILTIHFTGHSFIYGK | 1.25 | 1.45 | 2.00 | 0.79 | 2.12 |
| SEQ ID NO: 3 | KIVFKNMASRPYSIY | 2.91 | 2.45 | 2.01 | 2.91 | 2.01 |
| SEQ ID NO: 4 | FAVFDENKSWYLEDN | 1.86 | 1.36 | 2.05 | 1.61 | 1.56 |
| SEQ ID NO: 5 | ESNIMSTINGYVPES | 1.60 | 1.13 | 2.32 | 1.27 | 2.02 |
| SEQ ID NO: 6 | EKDIHSGLIGPLLI | 1.64 | 1.82 | 2.19 | 0.77 | 1.71 |
| SEQ ID NO: 7 | SHEFHAINGMIYSLP | 2.29 | 1.75 | 1.38 | 1.99 | 2.19 | traMax® M5 unit (Spectramax, Radnor, Pa.). Binding of experimental Tregitopes was expressed as the percent inhibition of the labeled control peptide (experimental fluorescence/control fluorescence multiplied by 100). The percent inhibition values for each experimental Tregitope (across a range of molar concentrations) were used to calculate the concentration at which it inhibits 50% of the labeled control Tregitope's specific binding, i.e. the Tregitope's $IC_{50}$.

The experimental Tregitopes were solvated in DMSO. The diluted Tregitopes were then mixed with binding reagents in aqueous buffering solution, yielding a range of final concentrations from 100,000 nM down to 100 nM. Tregitopes were then assayed against a panel of five common Class II HLA alleles: HLA-DRB1*0101, HLA-DRB1*0301, HLA-DRB1*0701, HLA-DRB1*1101, and HLA-DRB1*1501. From the percent inhibition of labeled control peptide at each concentration, $IC_{50}$ values were derived for each Tregitope/allele combination using linear regression analysis.

In this assay, the experimental Tregitopes are considered to bind with very high affinity if they inhibit 50% of control peptide binding at a concentration of 100 nM or less, high affinity if they inhibit 50% of control peptide binding at a concentration between 100 nM and 1,000 nM, and moderate affinity if they inhibit 50% of control peptide binding at a concentration between 1,000 nM and 10,000 nM. Low affinity peptides inhibit 50% of control peptide binding at concentrations between 10,000 nM and 100,000 nM. Peptides that fail to inhibit at least 50% of control peptide binding at any concentration below 100,000 nM and do not show a dose response are considered non-binders (NB).

Example 2. Peptide Characterization by Binding to HLA Class II Molecules

Soluble MHC binding assays were performed on the Tregitopes of the invention according to the methods described previously. $IC_{50}$ values (nM) were derived from a six-point inhibition curve. The list of synthesized Tregitopes used in binding assays is presented in Table 1. FIGS. 1A-C shows the binding curves for certain Tregitopes against the selected Class II HLA alleles. FIG. 1A summarizes the results for HLA DRB1 *0101 assay, FIG. 1B summarizes A summary of HLA binding results is presented in FIG. 25. EpiMatrix™ Predictions, calculated $IO_{50}$ values, and results classifications are reported for each Tregitope and HLA allele. Tregitope-allele combinations predicted to be cross-reactive between FV and FVIII are indicated. Of these Tregitope-allele interactions, 14/16 were shown to bind HLA indicating that these Tregitopes will generate measurable responses in human PBMC assays. Based on these findings, four Tregitopes were selected for further testing: SEQ ID NO: 3, SEQ ID NO: 5, SEQ ID NO: 1, and SEQ ID NO: 7. Tregitopes SEQ ID NO: 4 and SEQ ID NO: 6 were set aside due to their highly-restricted HLA binding profiles.
(3) Methods for Assessing the Phenotype of Peptide-Exposed APC Surface expression of Class II HLA (HLA-DR) and CD86 by professional antigen presenting cells (APCs) is one way APCs modulate T cell response. Expression of Class II HLA surface marker is down-regulated in response to Tregitopes, and in particular to, the control Tregitope 167 (21$^{st}$ Century Biochemicals, Marlboro, Mass.). Additionally, reduced expression of surface marker CD86 correlates positively with enhanced $T_{Reg}$ function (Zheng Y et al., J Immunol, 2004, 172(5):2778-84). In this assay, candidate Tregitopes, including the selected Tregitopes, were tested for their ability to down-regulate the expression of Class II HLA and the co-stimulatory molecule CD86 on the surface of professional APCs, specifically dendritic cells.

Each of the four Tregitopes selected for further testing were individually tested for regulatory potential using a proprietary APC phenotyping assay previously developed at EpiVax (EpiVax, Providence, R.I.). Previously harvested and frozen PBMC were thawed and suspended in chRPMI by conventional means. Under the direction and guidance of the Inventors from EpiVax, HLA typing was conducted on small, extracted samples of cellular material, provided to EpiVax, by Hartford Hospital (Hartford, Conn.). On assay day 0, 0.5×10$^6$ cells were extracted, screened for the presence of surface marker CD11c (a marker specific to dendritic cells) and analyzed for the presence of surface markers HLA-DR and CD86 by flow cytometry. The remaining cells were plated (4.0×10$^6$ cell per ml in chRPMI plus 800 ul media) and stimulated (50 μg/mL) with one of the four selected peptides or positive and negative controls including buffer only (negative control), Tregitope 167 (positive control, SEQ ID NO: 15) ($21^{st}$ Century Biochemicals, Marlboro, Mass.), Flu-HA 306-318 (negative control) ($21^{ST}$ Century Biochemicals, Marlboro, Mass.) and Ova 323-339 (negative control) ($21^{st}$ Century Biochemicals, Marlboro, Mass.). Plated cells were incubated for seven days at 37° C. On assay day 7, incubated cells were screened by flow cytometry for the presence of surface marker CD11c. CD11c positive cells were then analyzed for the presence of surface markers HLA-DR and CD86. The experimental peptides were tested in samples drawn from five different human donors.

Prior to March 2015, all whole blood samples used in the experiments were sourced from healthy donors under IRB 07115 protocol (Clinical Partners, Johnston, R.I.). Leukocytes were isolated using a conventional ficoll separation gradient (Noble P B and Cutts J H, Can Vet J, 1967, 8(5):110-11). After April 2015, Leukocyte Reduction Filters were obtained from the Rhode Island Blood Center (Providence, R.I.) to filter the white blood cells from whole blood obtained from healthy donors. After the whole blood was run through the filters, the filters were flushed in the opposite direction to push collected white blood cells out of the filter. The white blood cells were then isolated using a conventional ficoll separation gradient. The collected white blood cells were thereafter frozen for future use. When needed for use in an assay, the frozen white blood cells were thawed using conventional methods. For the GvHD studies discussed below, PBMCs were obtained from HemaCare, Van Nuys, CA and the experiments were performed at Lifespan Hospital (Providence, R.I.).

Figure 3A:
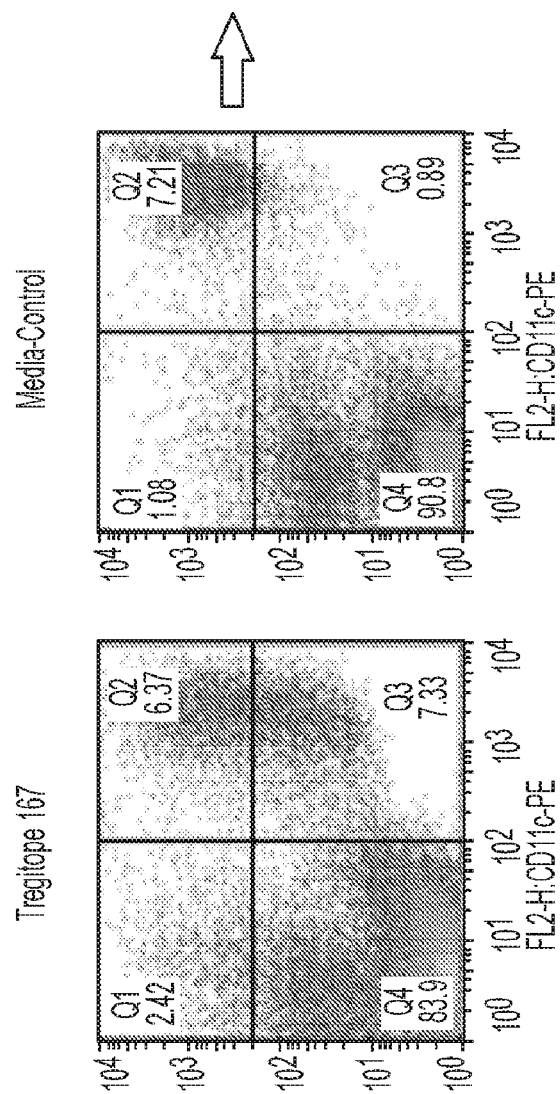
Figure 4:
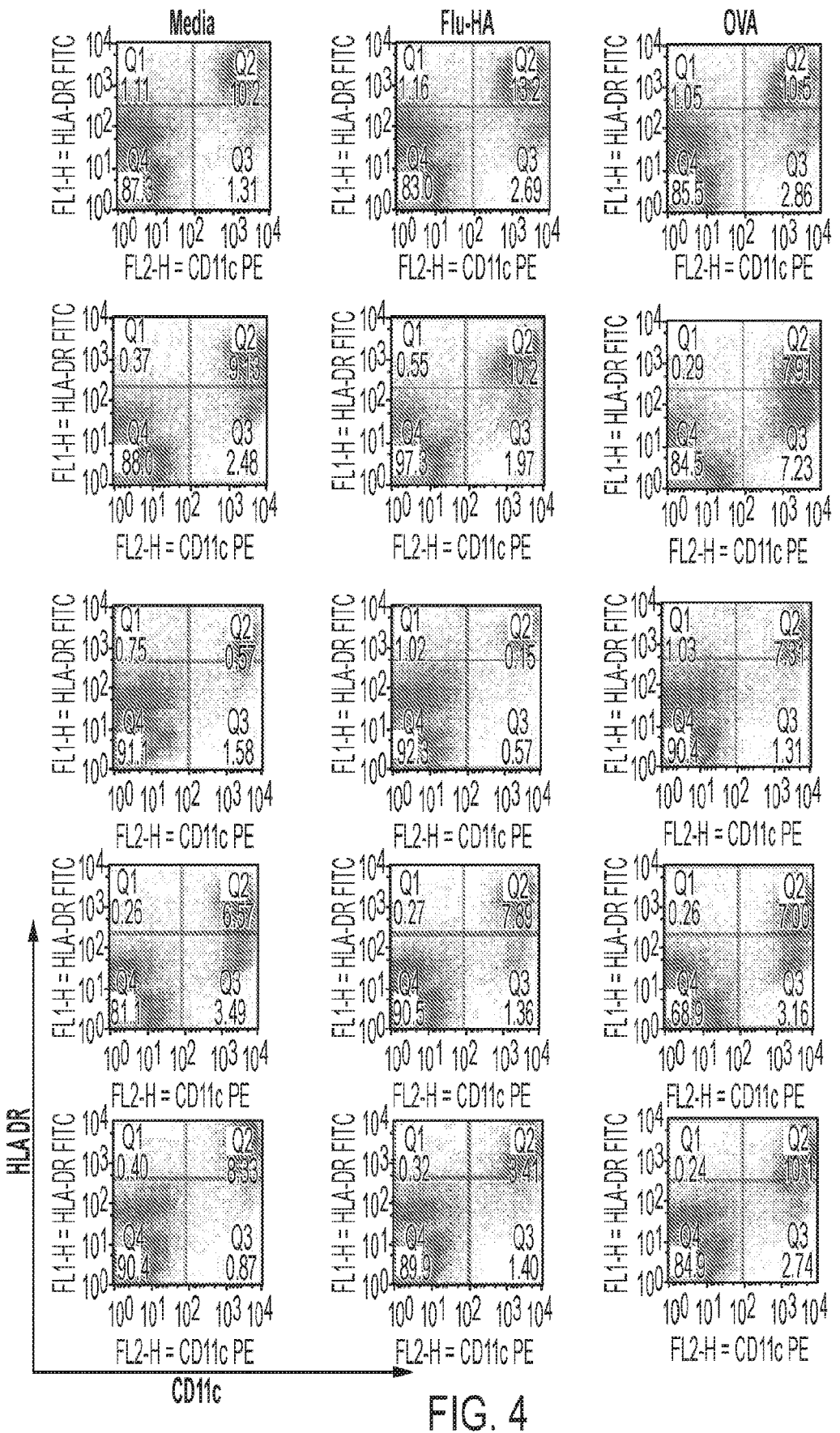
FIG. 4 is a series of dot plots representing the surface expression of CD11 vs HLA-DR analyzed on assay day 7 across the five donors in the presence of various peptide stimulants. $T_{Reg}$ 167 (shown as 167 in the figure) was used as a control and has the sequence PAVLQSSGLYSLSLSSVVTVPSSSLGTQ (SEQ ID NO: 15).
Figure 4:
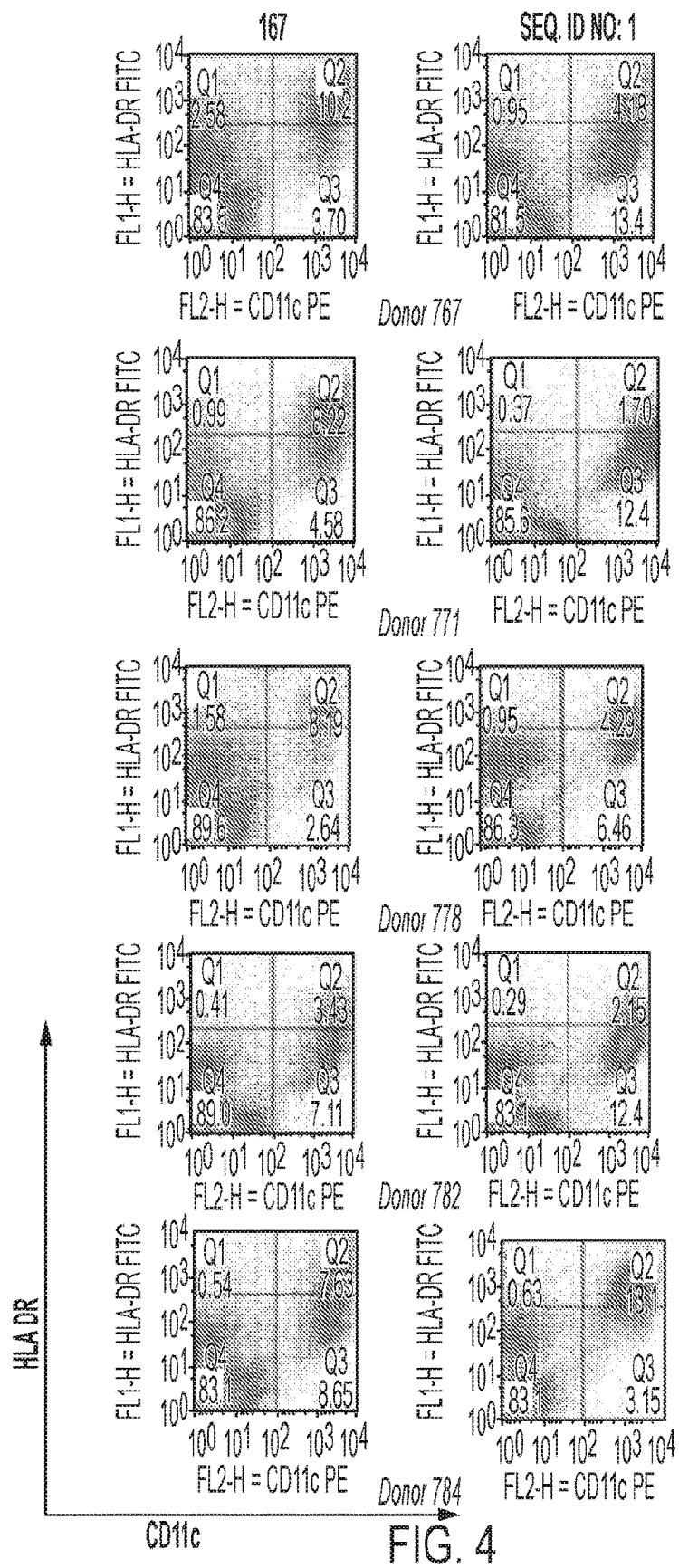
Figure 4:
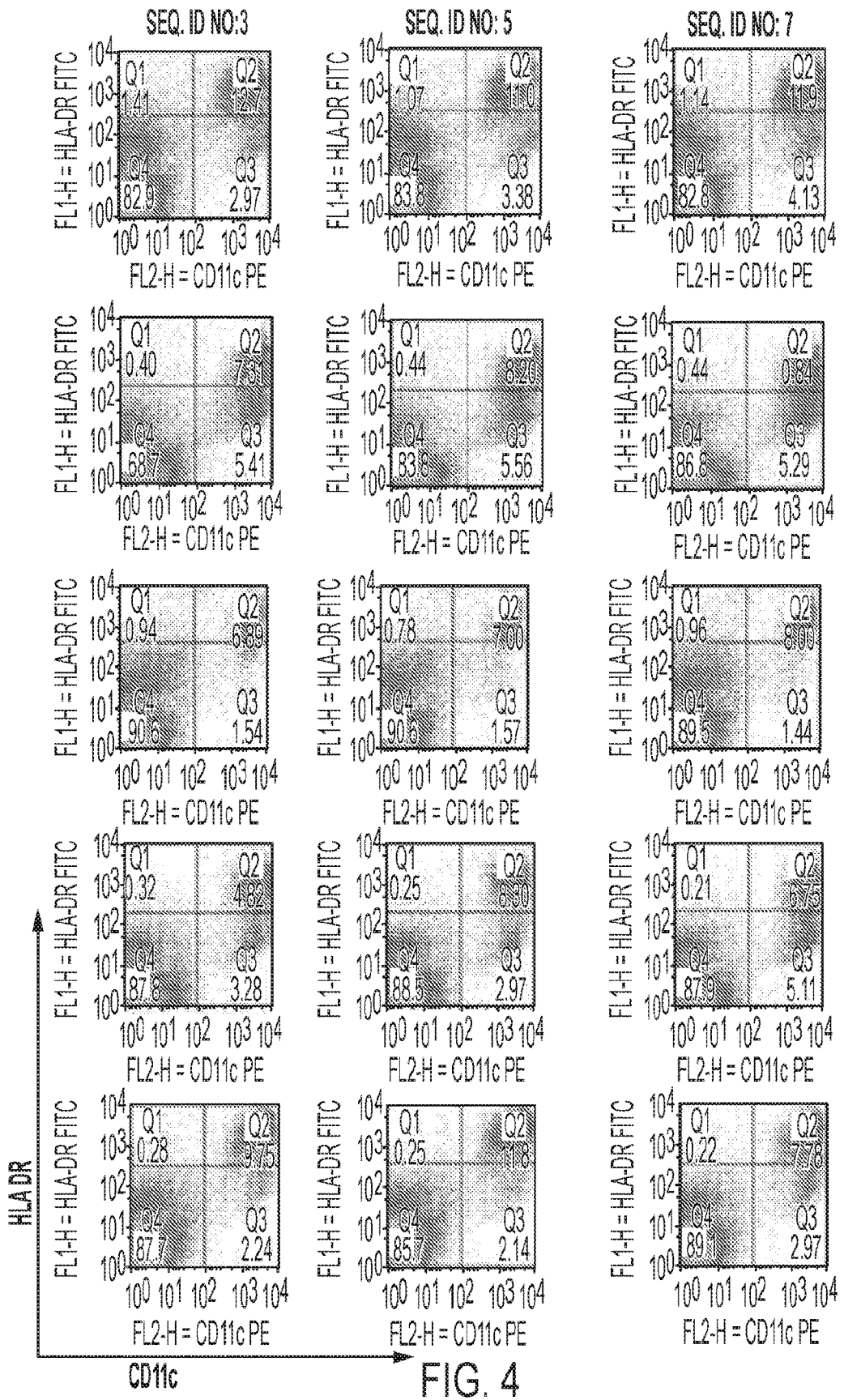

Exposure to putative Tregitopes on the phenotypes of dendritic cells was measured by multiple means. First, for each experimental condition, dot-plots, contrasting surface expression of CD11c and HLA-DR, were produced (FIG. 4). Dot-plots of cells exposed to all control and experimental peptides were overlaid onto dot-plots produced from control cells exposed to only the culture media. The overlay provided an effective method to visually observe shifts in HLA-DR distribution between Tregitope stimulated and unstimulated CD11c-high cells (see FIG. 2A, depicts an overlay of HLA-DR/CD11c dot plots for SEQ ID NO. 15 (Tregitope 167, dark gray) and media control (light gray) highlights the shift in observed HLA-DR expression). Observed shifts in the distribution of HLA-DR were reported as a qualitative measure. Next, the change in intensity of HLA-DR expression for the CD11c-high segment of each dot-plot was calculated using the equation of FIG. 2B. Percent change in intensity of HLA-DR expression equals Mean Florescence Index (MFI) of HLA-DR expression for peptide exposed cells minus MFI of HLA-DR expression for media exposed cells divided by MFI of HLA-DR expression for media exposed cells, times 100 ($^{HLA-DR}MFI_{peptide}-^{HLA-DR}MFI_{media}/^{HLA-DR}MFI_{media}*100$). FIG. 2C is a bar graph showing the % Δ in HLA-DR MFI for each peptide stimulant. Next, the percent change in the percentage of HLA-DR-low cells present among the CD11c high population was calculated for each peptide relative to media control (FIG. 3A-C). Percent change in the percentage of HLA-DR-low cells was calculated using the equation of FIG. 3C, and equals the percent of HLA-DR-low for peptide exposed cells minus the percent of HLA-DR-low for media exposed cells divided by percent of HLA-DR-low for media exposed cells times 100 ($^{HLA-DR}\%_{peptide}-^{HLA-DR}\%_{peptide}/^{HLA-DR}\%_{peptide}*100$). In this assay, a negative change in observed HLA-DR MFI and a positive change in percentage of HLA-DR-low cells present in the CD11c-high population indicated reduced expression of HLA and a shift to a regulatory APC phenotype. FIG. 3A is a plot of HLA-DR versus CD11c for SEQ ID NO. 15 (Tregitope 167, which was used as a control and has the formula PAVLQSSGLYSLSLSSVVTVPSSSLGTQ) and the media control. FIG. 3B is a bar graph that plots the % of HLA+ and HLA− each peptide stimulant where the vehicle is media.

Figure 5:
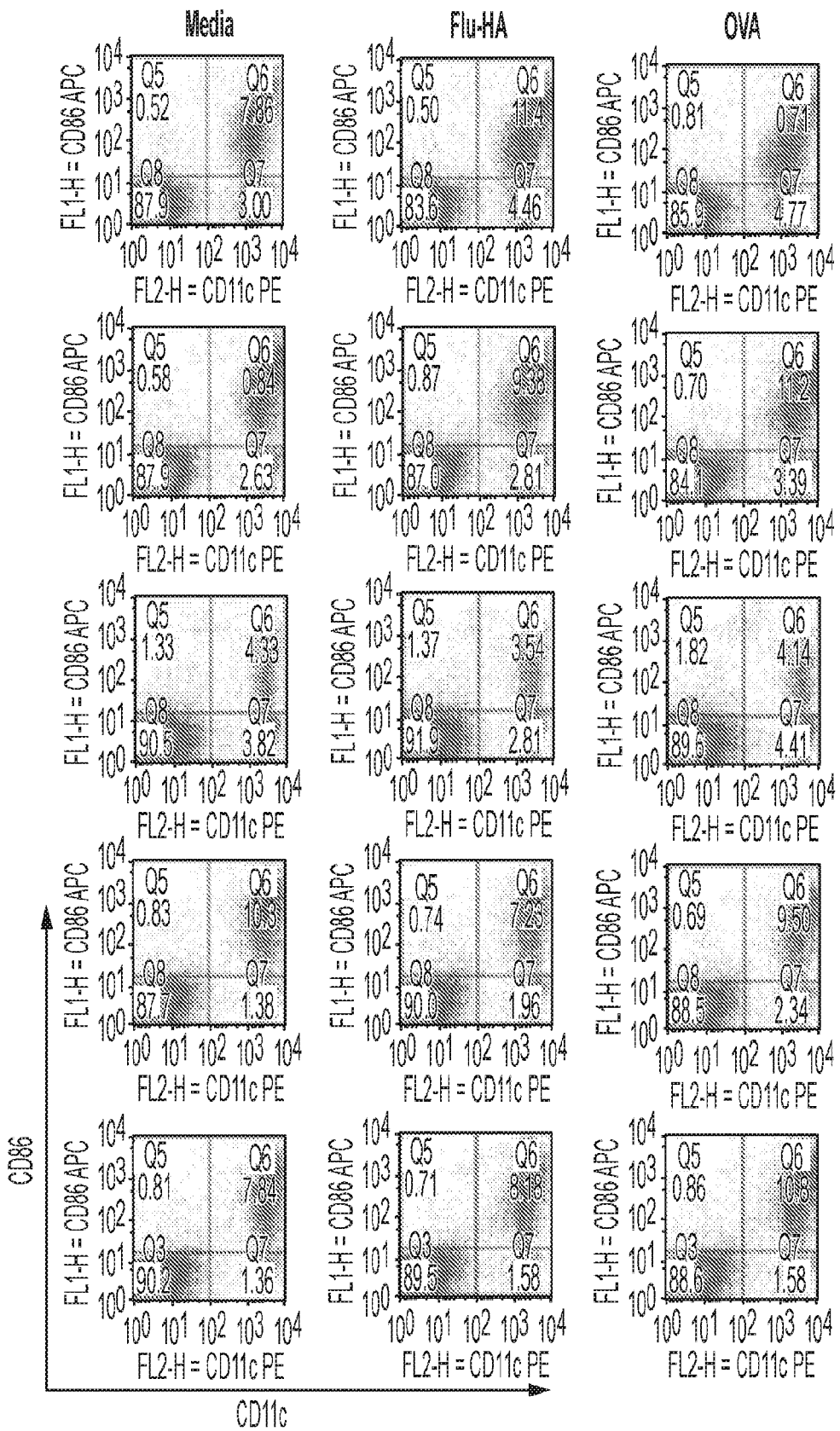
FIG. 5 is a series of dot plots representing the surface expression of CD11c vs CD86 analyzed on assay day 7 across the five donors in the presence of various peptide stimulants. $T_{Reg}$ 167 (shown as 167 in the figure) was used as a control and has the sequence PAVLQSSGLYSLSLSSVVTVPSSSLGTQ (SEQ ID NO: 15).
Figure 5:
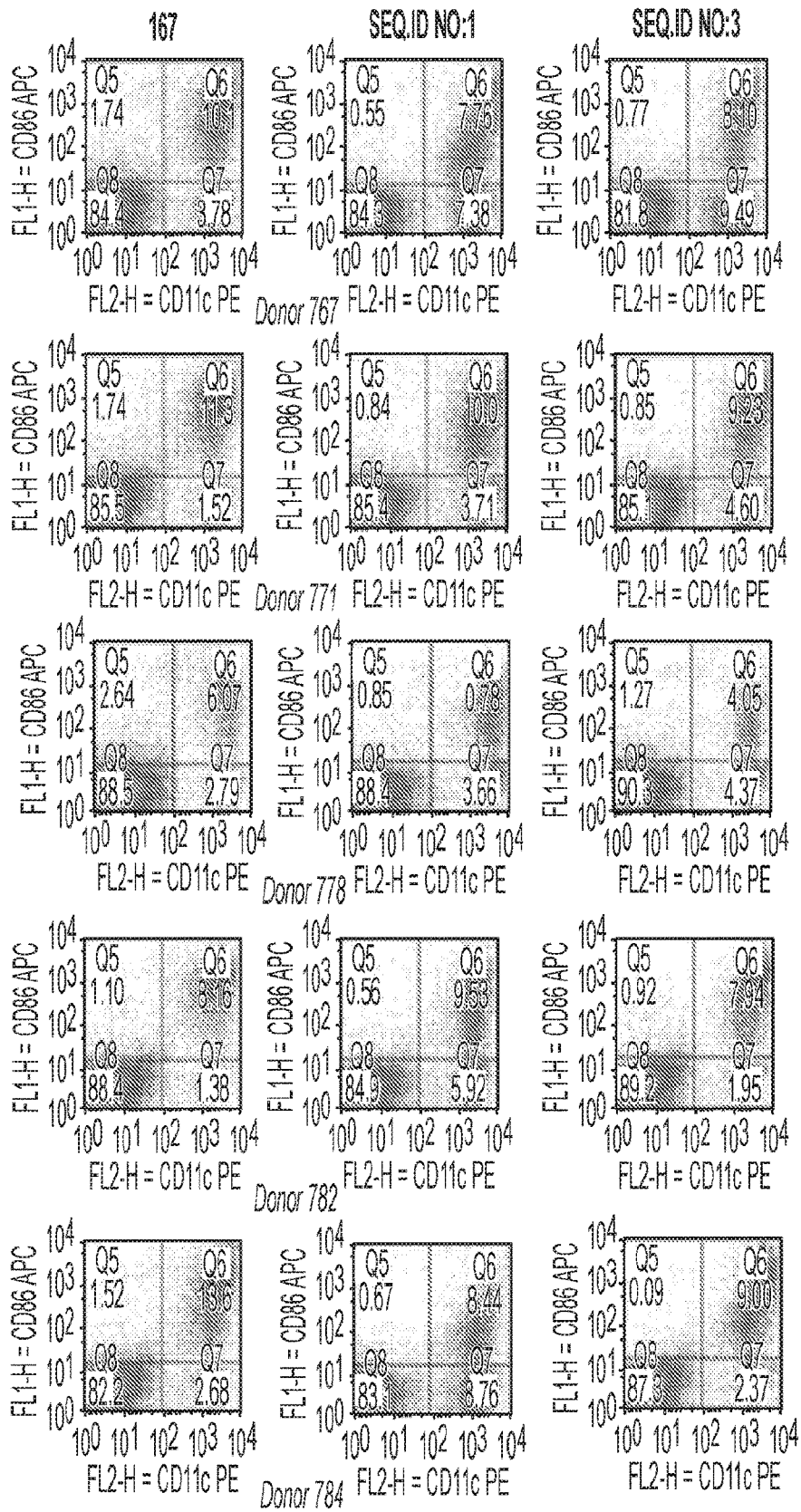
Figure 5:
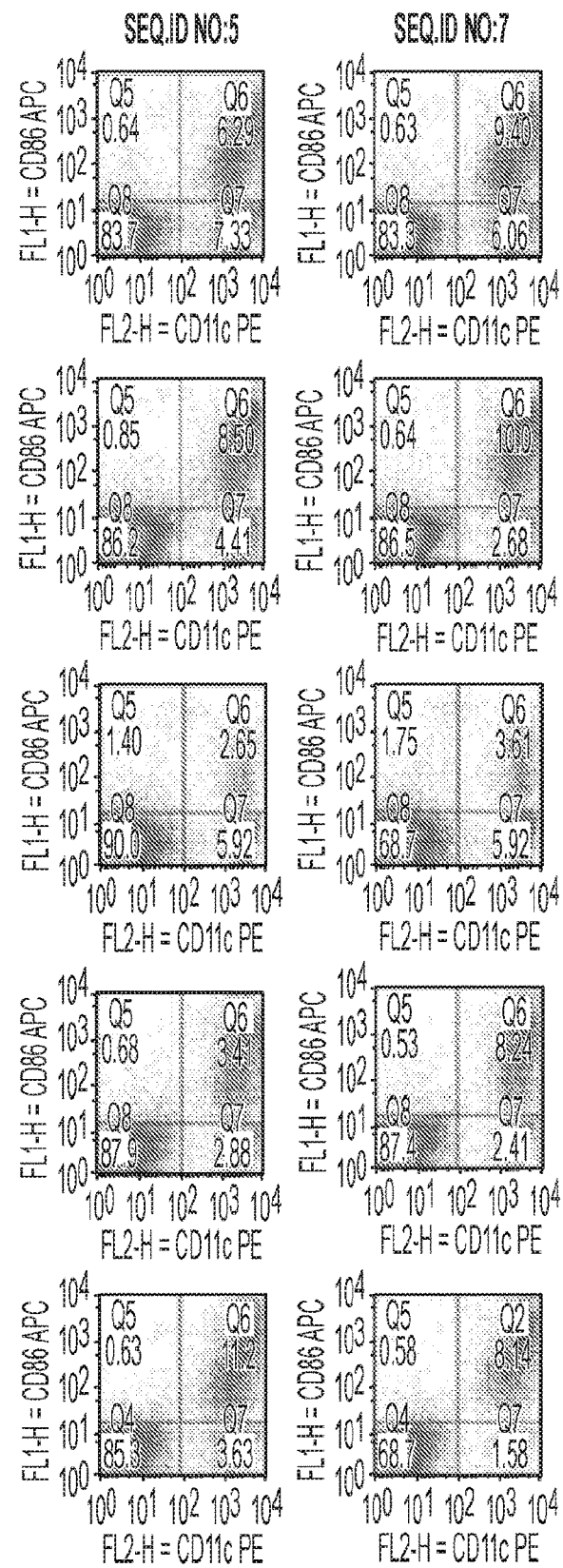

A similar process was used to assess the impact Tregitope exposure on surface expression of CD86; a costimulatory molecule known to promote T cell activation. First, for each experimental condition, dot-plots contrasting surface expression of CD11c and CD86 were produced (FIG. 5). Dot-plots of cells exposed to all control and experimental Tregitopes were overlaid onto dots-plots produced from control cells exposed to only the culture media. The overlay provided an effective method to visually observe shifts in CD86 distribution between Tregitope stimulated and un-stimulated CD11c-high cells. (data not shown). Observed shifts in the distribution of CD86 were reported as a qualitative measure. Next, the change in intensity of CD86-high expression for the CD11c-high segment of each dot-plot was calculated. Percent change in intensity of CD86-high expression equals Mean Florescence Index (MFI) of CD86 expression for peptide exposed cells minus MFI of CD86-high expression for media exposed cells divided by MFI of CD86 expression for media exposed cells, times 100 ($^{CD86-high}MFI_{peptide}-^{CD86-high}MFI_{peptide}/^{CD86-high}MFI_{peptide}*100$). (data not shown). Next, the percent change in the percentage of CD86-low cells present among the CD11c high population was calculated. Percent change in the percentage of CD86-high cells equals the percent of CD86-high for peptide exposed cells minus the percent of CD86-high for media exposed cells divided by percent of CD86-high for media exposed cells, times 100 ($^{CD86-low}\%_{peptide}-^{CD86-low}\%_{peptide}/^{CD86-low}\%_{peptide}*100$). In this assay, a negative change in observed CD86 MFI and a positive change in percentage of CD86-low cells present in the CD11c-high population indicates reduced expression of CD86 and a shift to a regulatory APC phenotype.

Example 3. Characterization of Peptide Exposed APC

Dendritic cell phenotyping assays were performed on the selected Tregitopes according to the methods described previously. Dot-plots corresponding to each experimental condition tested in each of five human donors are presented in FIG. 4 and FIG. 5.

FIG. 4 is a series of dot plots representing the surface expression of CD11 vs HLA-DR analyzed on assay day 7 across the five donors in the presence of various peptide stimulants. The downward movement of the CD11c+/HLA-DR+ population (upper right quadrant of FIG. 4) was apparent in the samples treated with SEQ ID NO: 1 as compared to media control indicating an acquired regulatory phenotype. Tregitope 167 (SEQ ID NO. 15, positive control) and some of the other FV peptides responded similarly, but the observed shift is more prominent with SEQ ID NO: 1.

FIG. 5 is a series of dot plots representing the surface expression of CD11c vs CD86 analyzed on assay day 7 across the five donors in the presence of various peptide stimulants. An increase in CD86-low cells present in the samples treated with SEQ ID NO: 1, when compared to media control, indicated a shift to the acquired regulatory phenotype. FIG. 22 summarizes the results obtained through the dendritic cells phenotyping assays described previously.

As presented in FIG. 22, exposure to claimed Tregitope SEQ ID NO: 1, decreased expression of HLA-DR in all five subjects tested. Further, in four out of five subjects, exposure to Tregitope SEQ ID NO: 1 increased the percent of CD86-low present among the CD11c-high cohort. Both trends indicated a shift towards an acquired regulatory phenotype.
(4) Methods for Assessing Peptide Effects on Proliferation of Regulatory T Cells Previous studies performed by EpiVax (Providence, R.I.) demonstrated increased proliferation of regulatory T cells following exposure to known Tregitope including positive control Tregitope 167 (SEQ ID NO: 15, 21s$^r$ Century Biochemicals, Marlboro, Mass.). In this assay, candidate Tregitopes, including the Tregitopes of the instant disclosure, were tested for their ability to induce proliferation among CD4+CD25+ FoxP3+ regulatory T cells. Previously harvested and frozen PBMC were thawed and suspended in conditioned chRPMI (3.3x10$^6$ cells/mL) by conventional means. Cells were stained with CFSE (Cat #: 65-0850-84, Affymetrix, Santa Clara, Calif.) and plated at 300,000 cells per well. Plates were incubated overnight (37° C. in 5% $CO_2$). On assay day 1, SEQ ID NO: 1 and SEQ ID NO: 3 (control peptide) were reconstituted in sterile DMSO yielding a final stock concentration of 20 mg/mL. Previous titration experiments performed at EpiVax (EpiVax, Providence, R.I.) have established that stimulation with 0.5 μg/ml Tetanus Toxoid (TT) (Astarte Biologics, Bothell, Wash.) elicits a measurable CD4+ effector memory T cells response in PBMC drawn from healthy control donors (Rhode Island Blood Center, Providence, R.I.). Tetanus Toxoid stock (100 μg/mL) (Astarte Biologics, Bothell, Wash.) was diluted in conditioned chRPMI yielding a working concentration of 1 ug/mL. Plated cells were then stimulated with either 100 μL of conditioned chRPMI (negative control), 100 μL Tetanus Toxoid solution (positive control) (Astarte Biologics, Bothell, Wash.), 100 μL of a dilution of 2991 μL Tetanus Toxoid solution plus 9 μL SEQ ID NO: 1 solution, 100 μL of a dilution of 2997 μL Tetanus Toxoid solution plus 3 μL SEQ ID NO: 1 solution, or 1004 of a dilution of 6998.24 Tetanus Toxoid solution plus 1.84 SEQ ID NO: 1 solution. In parallel, control wells with identical number of the same cells were incubated with SEQ ID NO: 3 peptide solutions prepared as described for SEQ ID NO: 1. All plates were then incubated for six additional days. On assay day five, 1004 of supernatant was removed from each well and replaced with freshly conditioned chRPMI.

We selected highly activated regulatory T cells displaying elevated levels of FoxP3, CD25, Granzyme B and proliferation. The gating strategy for highly activated regulatory T cells is shown in FIGS. 6A-B (which depict a representative result using Donor 157), in which CD4+ T cells are gated for elevated CD25, Granzyme B, FoxP3, and low CFSE (proliferation). FIG. 6A shows the results of the representative assay with no added TT, while FIG. 6B shows the results of the representative assay with 0.5 μg/ml TT.

Figure 7:
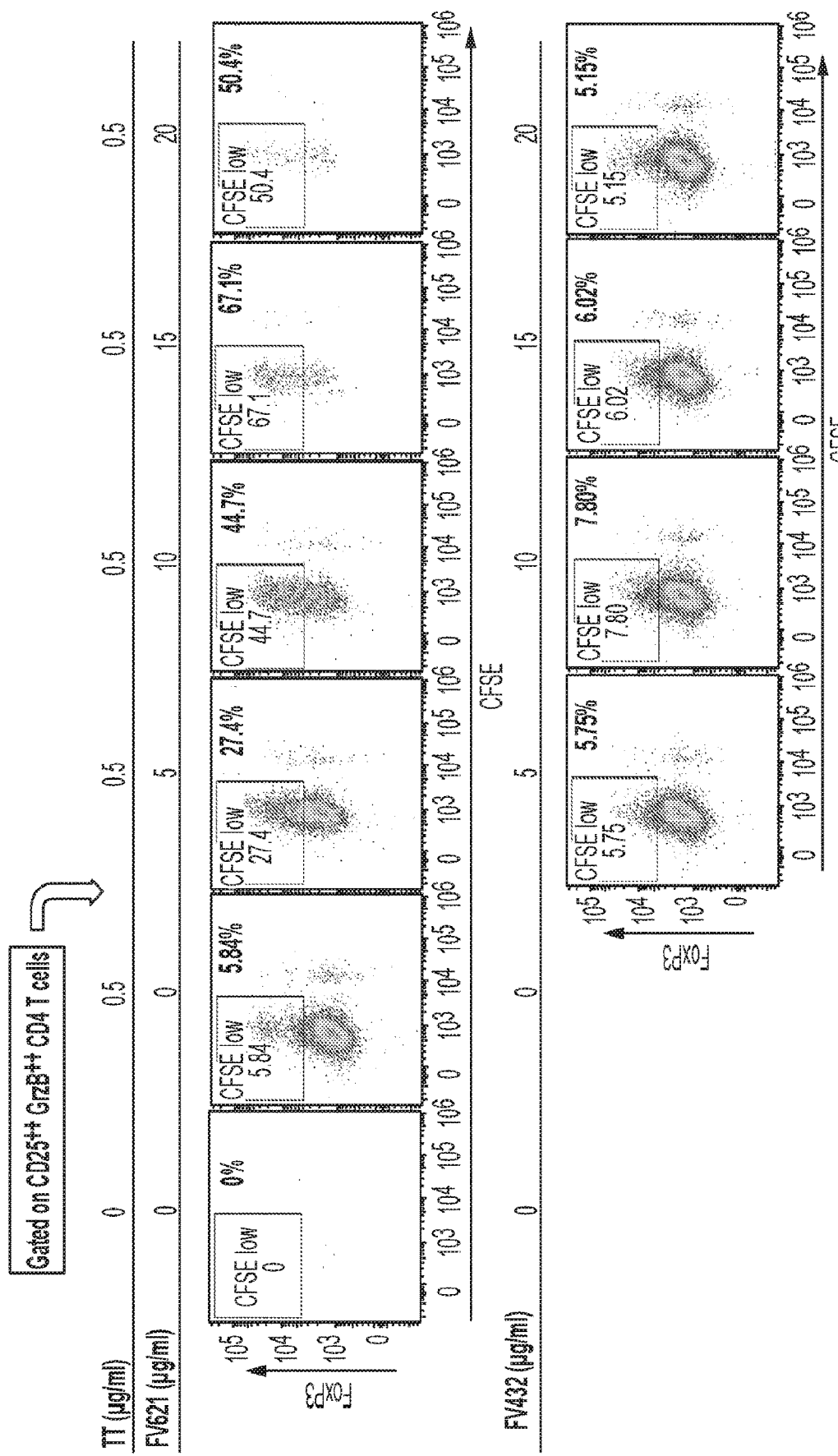
FIG. 7 demonstrates that gating of highly activated Granzyme B positive CD4+ T cells (CD25+ Granzyme B+) shows that a subset of these cells is composed of highly proliferative regulatory T cells (CFSE low FoxP3++). SEQ ID NO: 1 (shown as FV621) increases the relative proportion of this population (FIG. 7, top row), while SEQ ID NO: 3 (shown as FV432) has no significant effect (FIG. 7, bottom row). Data in the figure corresponds to Donor 135.
Figure 17A:
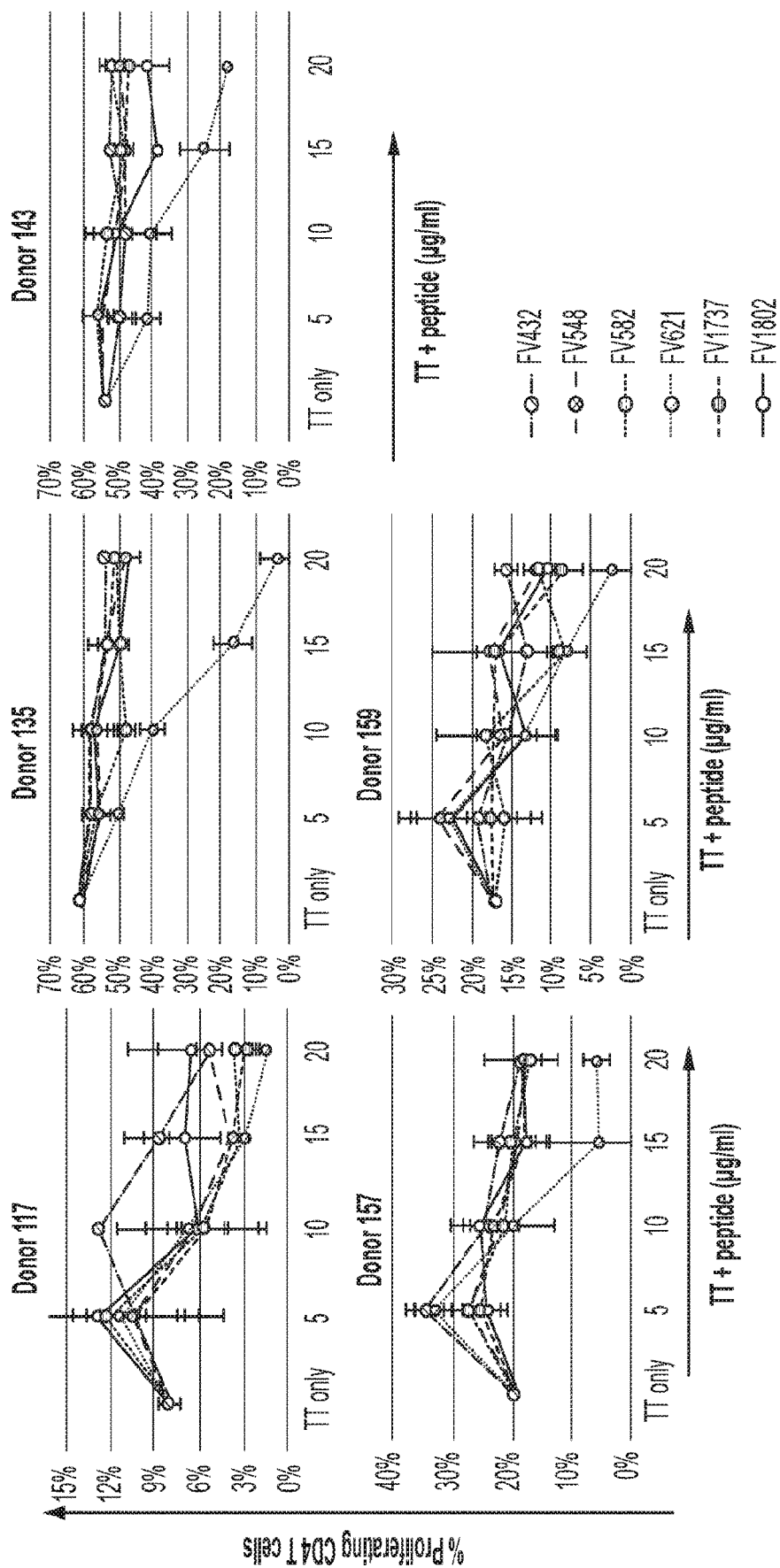
FIGS. 17A-B demonstrate that the inhibitory effect of the Tregitopes of the instant disclosure on activated (proliferating) CD4+ effector T cells responding to Tetanus Toxoid (FIG. 17A) mirrors that of highly activated (Granzyme B+) regulatory T cells (FIG. 17B) across donors covering a broad range of HLA-DRB1 haplotypes. For each donor, values are normalized to 100%=TT only, no Tregitope of the instant disclosure. As shown in both FIG. 17A and FIG. 17B, SEQ ID NO: 1 is shown as FV621, SEQ ID NO: 3 is shown as FV432, SEQ ID NO: 4 is shown as FV548, SEQ ID NO: 5 is shown as FV582, SEQ ID NO: 6 is shown as FV1737, and SEQ ID NO: 7 is shown as FV1802.
Figure 17B:
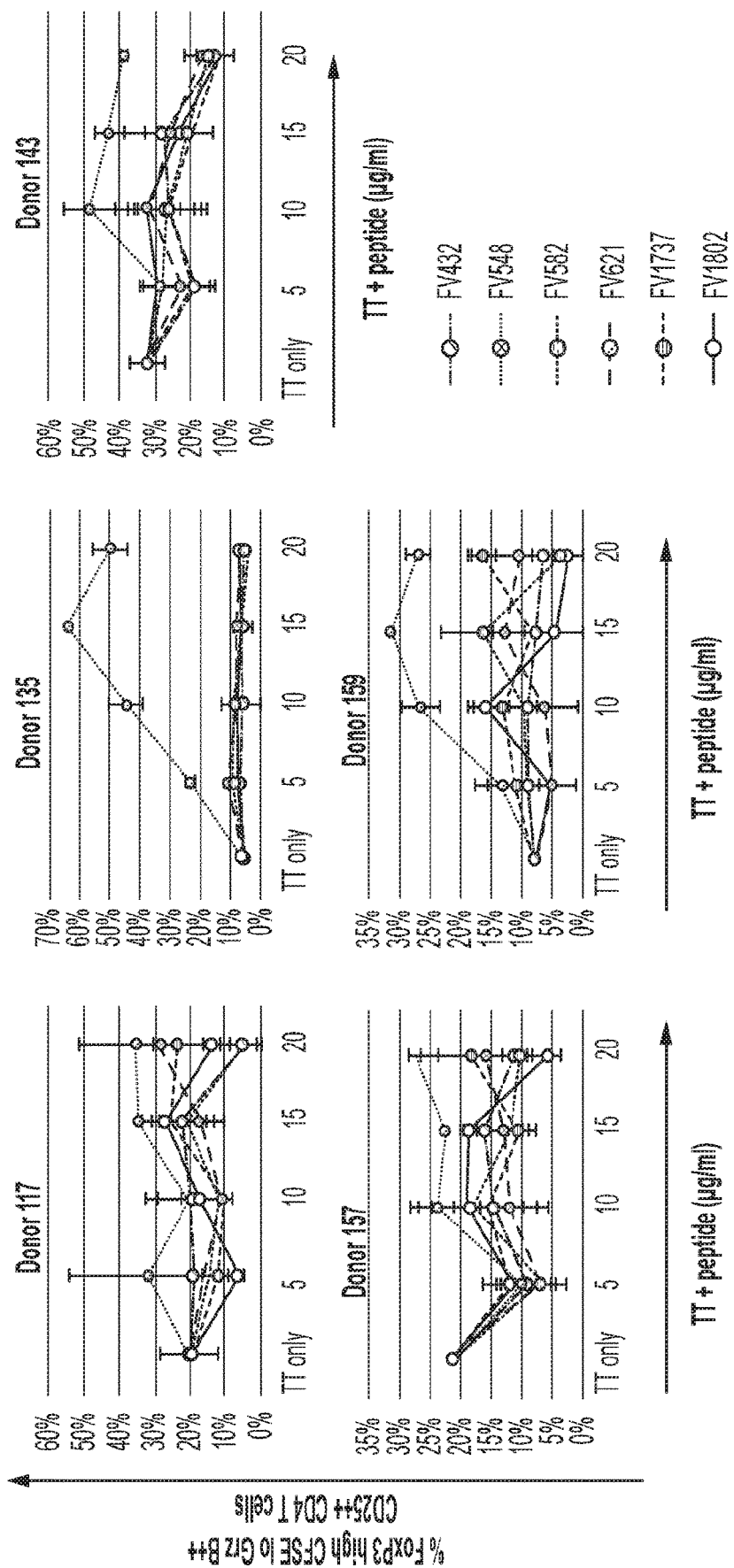
Figure 23:
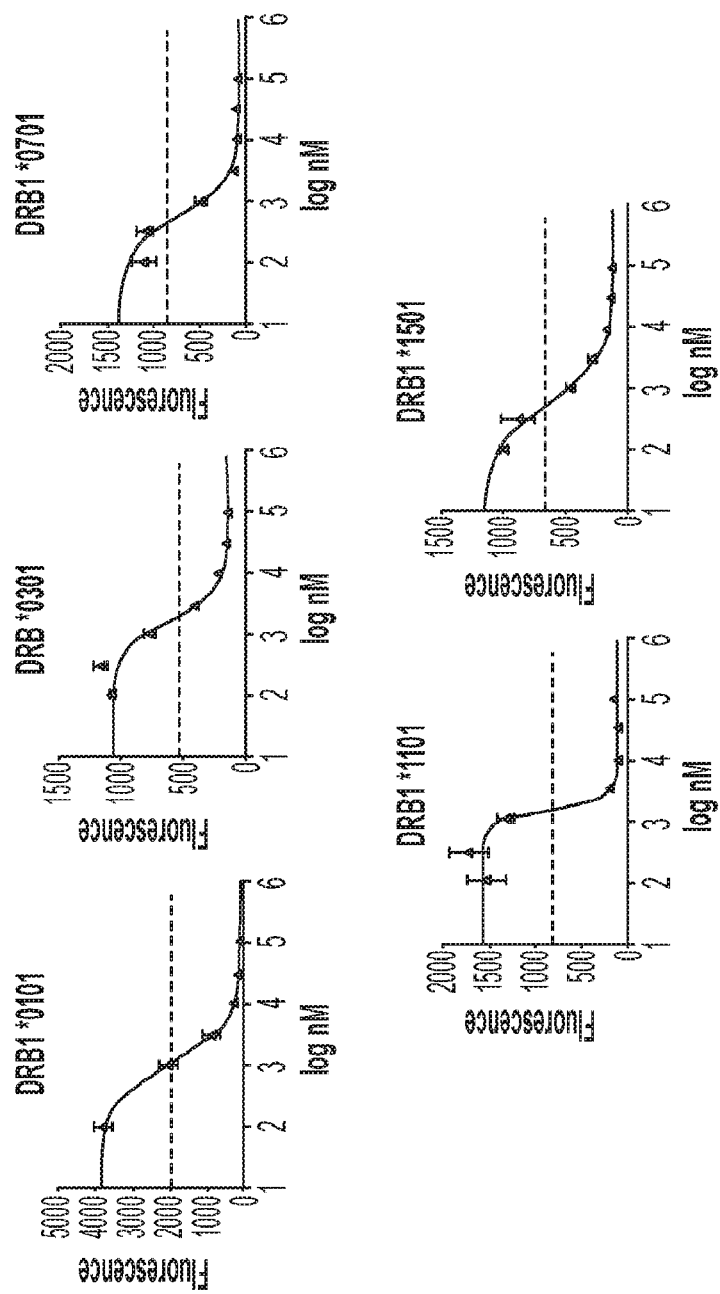
FIG. 23 shows the HLA binding results for SEQ ID NO: 1 across five HLA-DR1 types, which indicates a high affinity of binding for SEQ ID NO: 1 across multiple HLA Class II types.
Figure 24A:
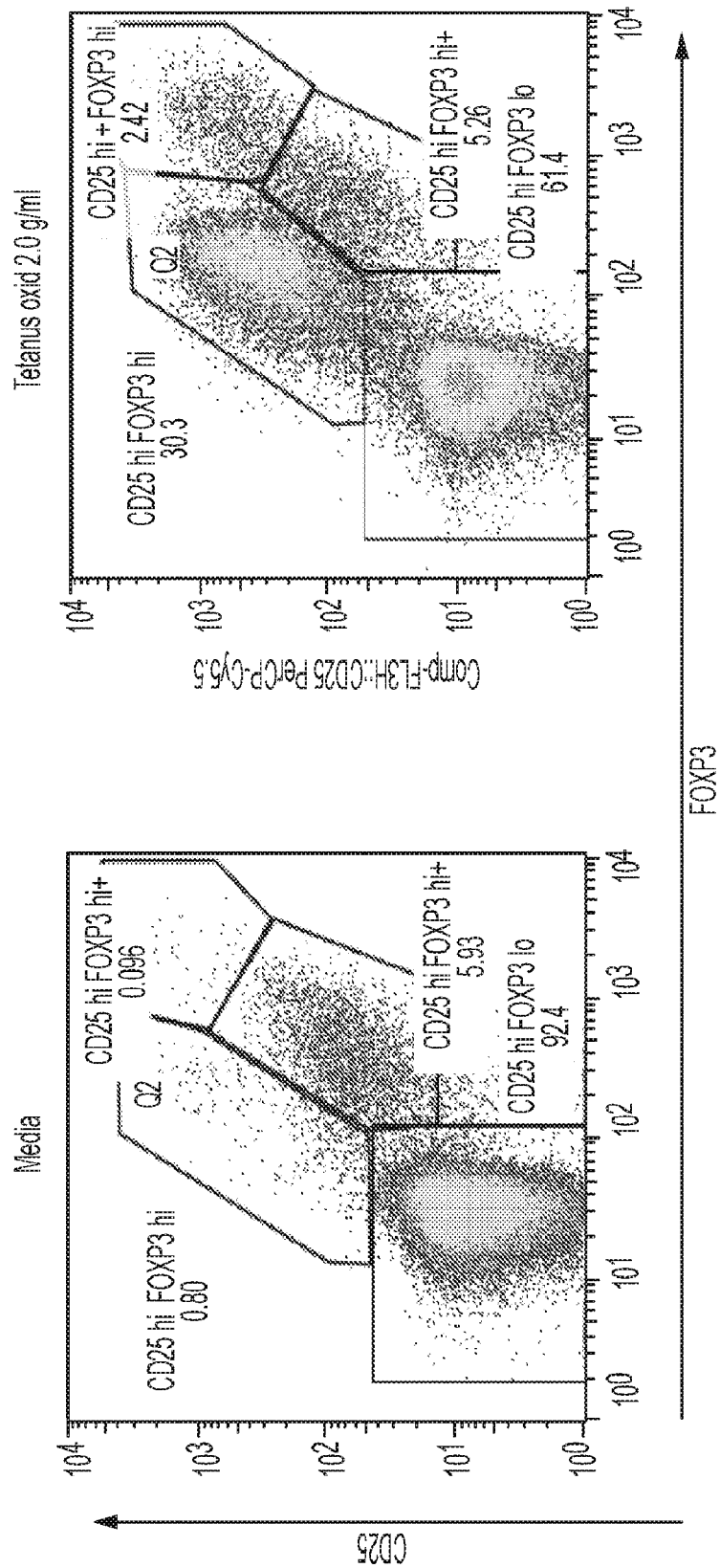
FIGS. 24A-D demonstrate the gating strategy employed for the Bystander Suppression Assay and highlights the regulatory and activation markers in CD4 T cells stimulated by TT, and demonstrating that the major proliferations population corresponds to the T effector memory phenotype (CD45RA-low/CCR7-low).
Figure 24B:
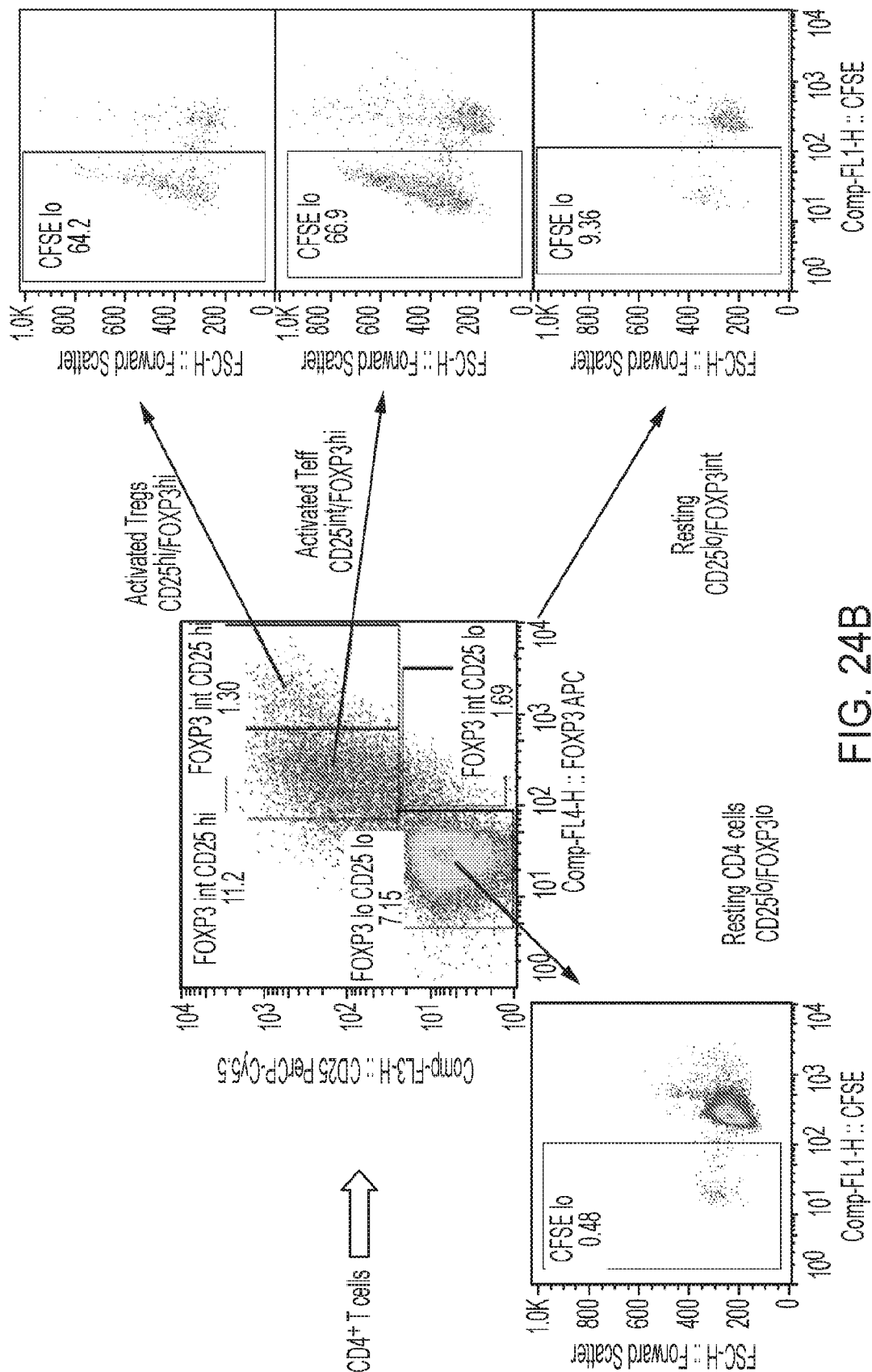
Figure 24C:
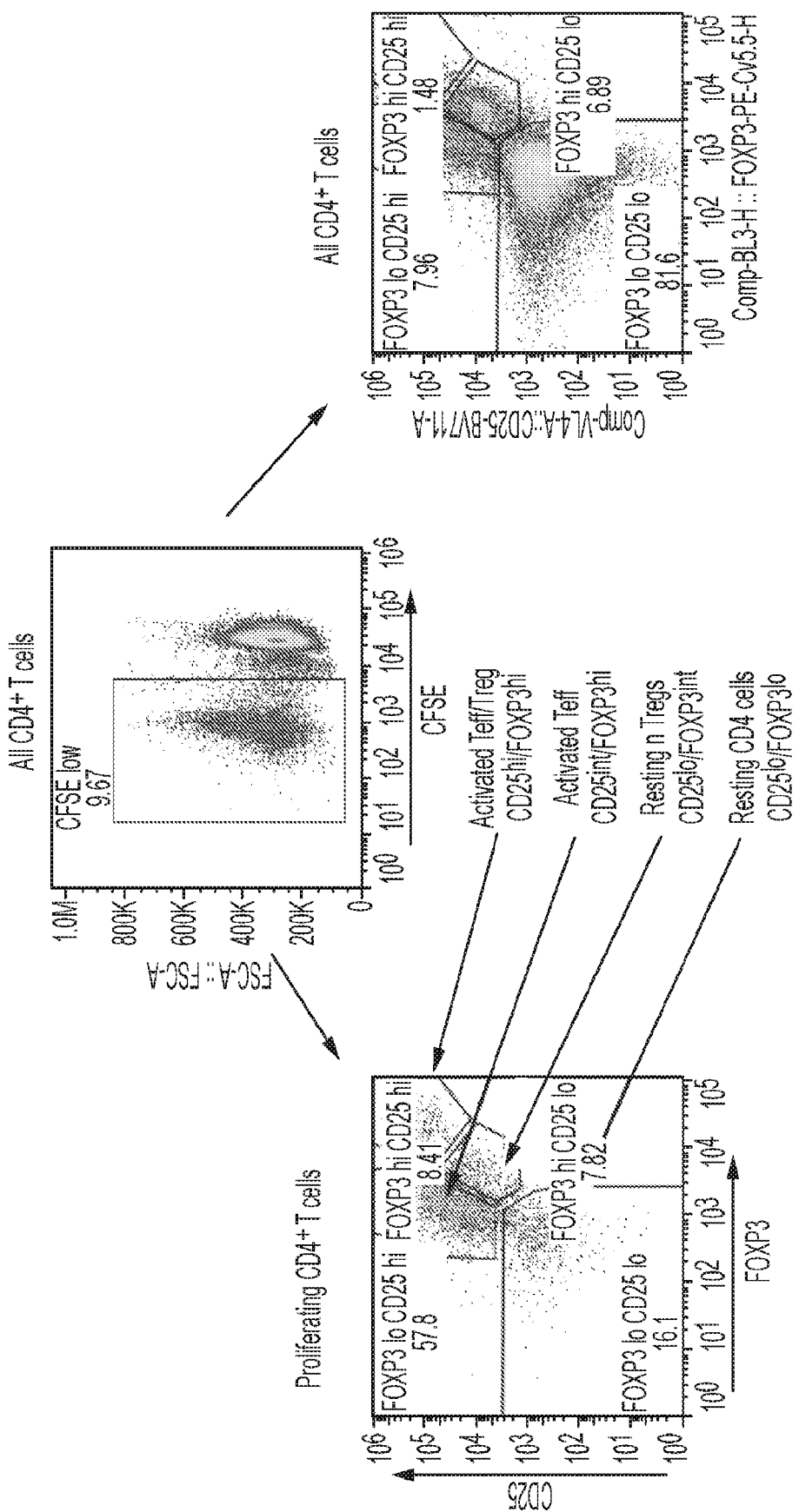
Figure 24D:
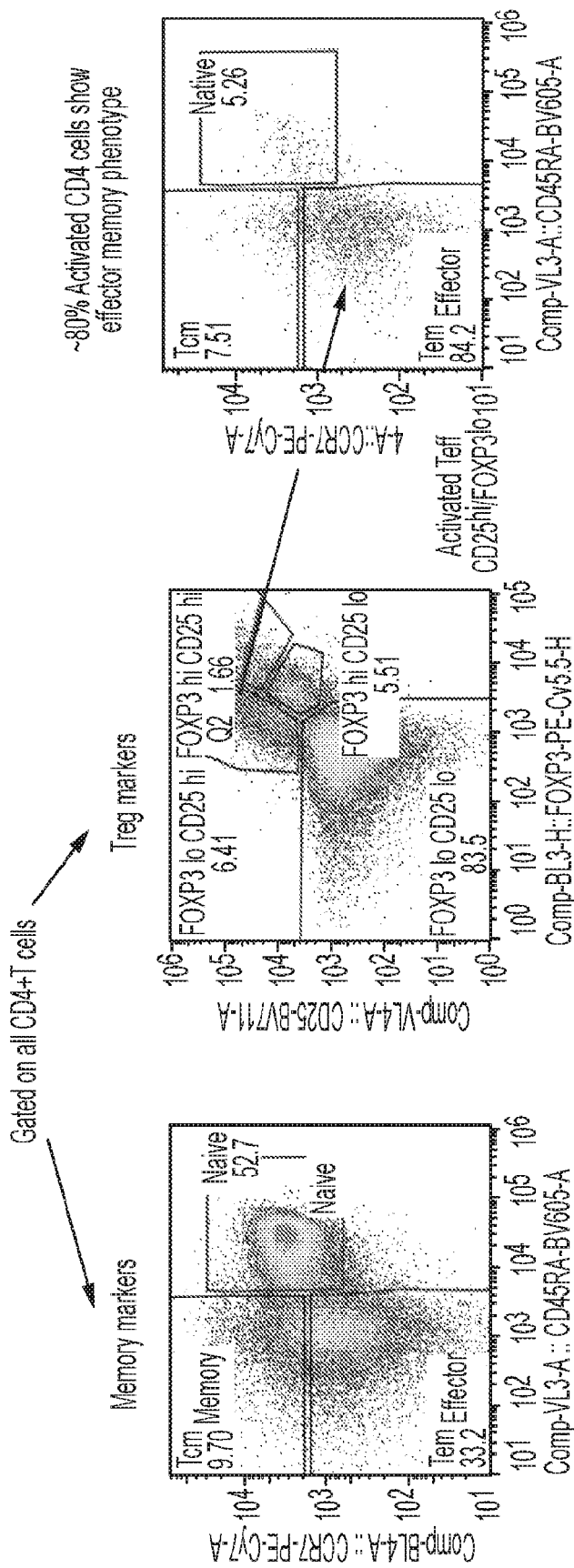

Example 4. SEQ ID NO: 1 Strongly Induces a Population of Highly Proliferative, Activated Regulatory T Cells Regulatory T cell proliferation assays were performed on the Tregitopes of the present disclosure according to the methods described previously. As depicted in FIG. 7, gating on highly activated Granzyme B positive CD4$^+$ T cells (CD25$^+$ Granzyme B$^+$) (as shown in FIGS. 6A-B), shows that a subset of them is composed of highly proliferative regulatory T cells (CFSE low FoxP3+). SEQ ID NO: 1 increases the relative proportion of this population, while SEQ ID NO: 3 has no significant effect. Data in the figure corresponds to Donor 135. The increase in this population of highly activated, Granzyme B positive regulatory T cells correlates closely with the degree of effector T cell inhibition shown by different Tregitopes of the present disclosure across multiple donors (FIGS. 17A-B), markedly increasing in relative numbers only in those cases where the Tregitopes of the present disclosure have an inhibitory effect on effector CD4$^+$ cells. This is suggestive of the involvement of cytotoxic regulatory T cells in the inhibitory mechanism of SEQ ID NO: 1. In total, this data demonstrates that SEQ ID NO: 1 strongly induces a population of highly proliferative, activated regulatory T cells rich in Granzyme B.
(5) Methods for Assessing Peptide Effects on Proliferation of CD4+ Effector T cells CD4+ effector memory T cells contained within PBMC cell populations can be induced to proliferate in response to stimulation with known T cell epitopes. EpiVax (Providence, R.I.) has demonstrated that SEQ ID NO: 1 binds multiple HLA molecules and that SEQ ID NO: 1 can induce a regulatory phenotype in exposed APC (Clinical Partners, Johnston, R.I.). Results of the competitive inhibition HLA binding assay provides an indirect measure of peptide-MHC affinity (Steere A C et al., J Exp Med, (2006), 203(4):961-71, herein incorporated by reference in its entirety). Binding of experimental Tregitopes is expressed as the percent inhibition of the labeled control peptide (experimental fluorescence/control fluorescence multiplied by 100). The percent inhibition values for each experimental Tregitope (across a range of molar concentrations) are used to calculate the concentration at which it inhibits 50% of the labeled control peptide's specific binding. This value is referred to as the $IC_{50}$. FIG. 23 shows the HLA binding results while Table 3 shows $IC_{50}$ for SEQ ID NO: 1 across five HLA-DR1 types, which indicates a high affinity of binding for SEQ ID NO: 1 across multiple HLA Class II types.

TABLE 3

HLA Binding results across multiple HLA alleles, showing $IC_{50}$ for SEQ ID NO: 1.

| | | | HLA-DRB1 allele and $IC_{50}$ | | | | |
|---|---|---|---|---|---|---|---|
| Peptide | Sequence | Features | *0101 | *0301 | *0701 | *1101 | *1501 |
| SEQ ID NO: 1 | Ac-ILTIHFTGHSFIYGK-amide | $IC_{50}$ | 1.078 | 2.067 | 472 | 1.528 | 549 |

Figure 9:
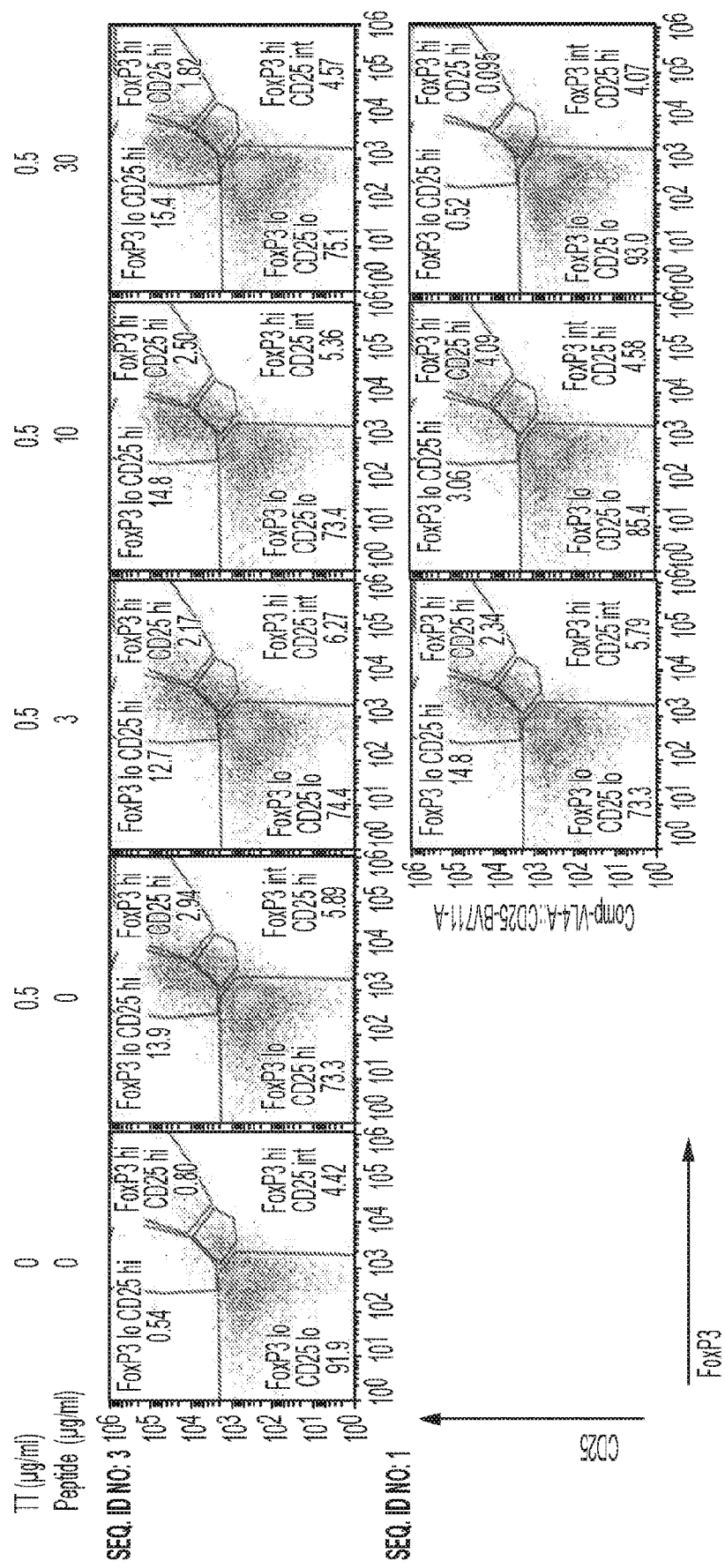
FIG. 9 depicts the activation of CD4+ T cells upon stimulation with tetanus toxoid (TT) and suppression by peptide SEQ ID NO: 1 (bottom row) and control peptide SEQ ID NO: 3 (top row).
Figure 10:
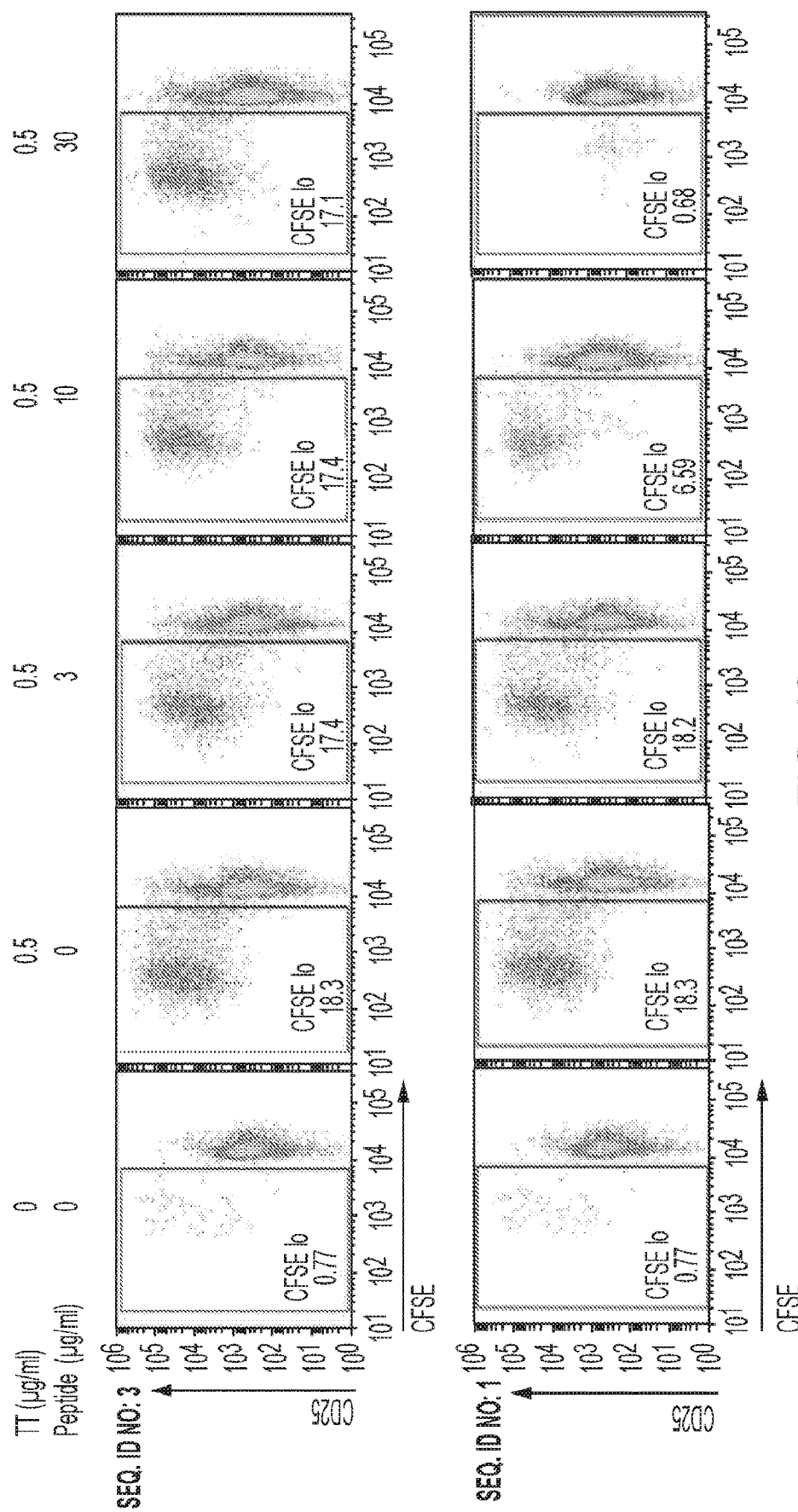
FIG. 10 reports the proliferation of CD4+ T cells upon stimulation with TT and suppression of same by peptide SEQ ID NO: 1 (bottom row) and control peptide SEQ ID NO: 3 (top row).
Figure 11:
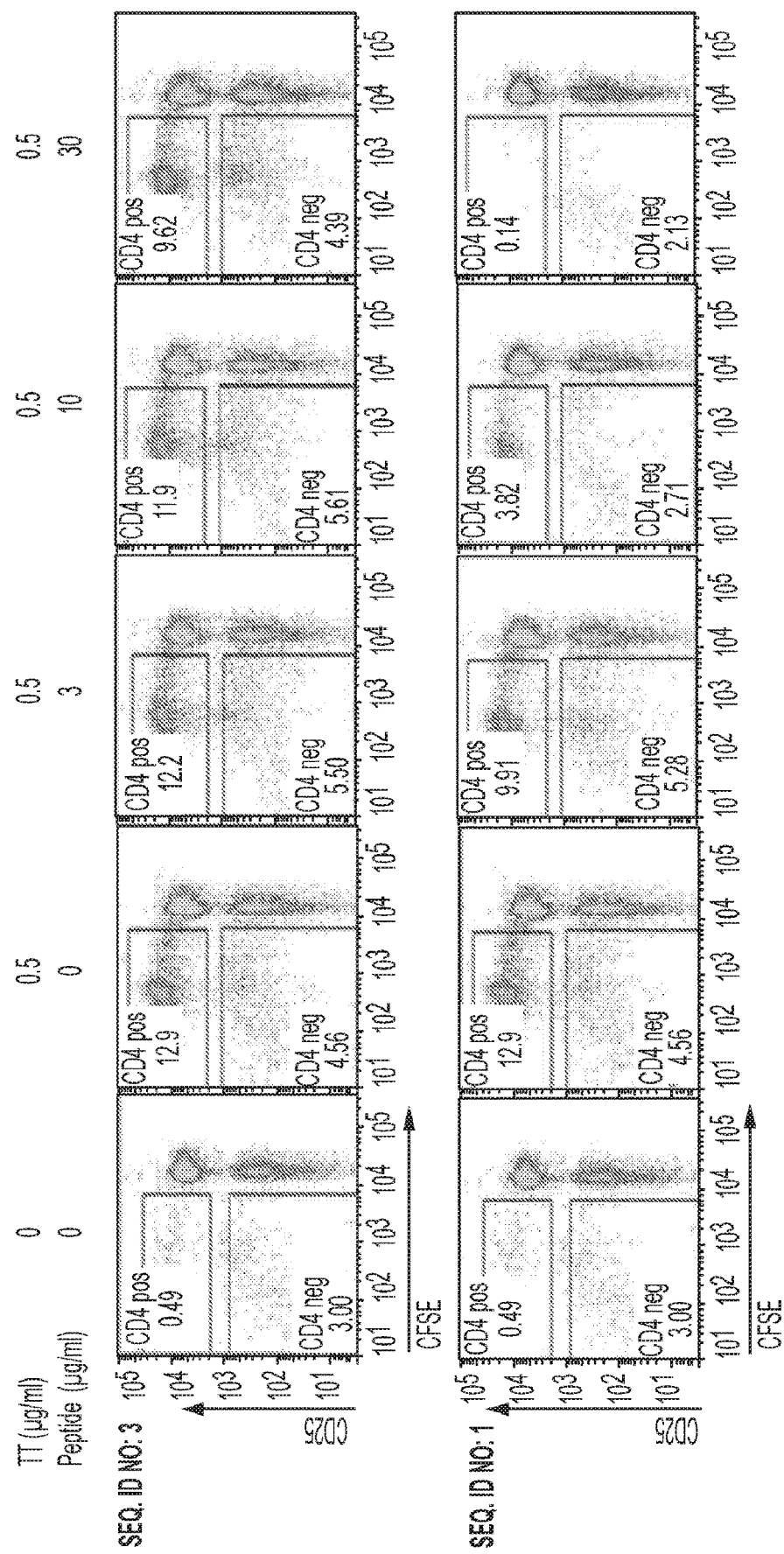
FIG. 11 depicts the activation of CD4+ T cells upon stimulation with tetanus toxoid (TT) and suppression by peptide SEQ ID NO: 1 (bottom row) and control peptide SEQ ID NO: 3 (top row).

The purpose of this experiment was to establish the ability of SEQ ID NO: 1 to suppress the proliferation of antigen stimulated CD4+ effector memory T cells by either direct (engagement and activation of $T_{Reg}$) or indirect (modulation of APC phenotype) means. For the initial study, SEQ ID NO: 3 was used as a negative control (FIGS. 9-11). In subsequent studies, the performance of SEQ ID NO: 1 was compared to its FVIII derived homologue SEQ ID NO: 2 (FIG. 13).

Previously harvested and frozen PBMC were thawed and suspended in conditioned chRPMI ($3.3 \times 10^6$ cells/mL) by conventional means. Cells were stained with CFSE (Cat #: 65-0850-84, Affymetrix, Santa Clara, Calif.) and plated at 300,000 cells per well. Plates were incubated overnight (37° C. in 5% $CO_2$). On assay day 1, SEQ ID NO: 1 and SEQ ID NO: 3 (control peptide) were reconstituted in sterile DMSO yielding a final stock concentration of 20 mg/mL. Previous titration experiments performed at EpiVax (EpiVax, Providence, R.I.) have established that stimulation with 0.5 μg/ml Tetanus Toxoid (TT) (Astarte Biologics, Bothell, Wash.) elicits a measurable CD4+ effector memory T cells response in PBMC drawn from healthy control donors (Rhode Island Blood Center, Providence, R.I.). Tetanus Toxoid stock (100 μg/mL) (Astarte Biologics, Bothell, Wash.) was diluted in conditioned chRPMI yielding a working concentration of 1 ug/mL. Plated cells were then stimulated with either 100 μL of conditioned chRPMI (negative control), 100 μL Tetanus Toxoid solution (positive control) (Astarte Biologics, Bothell, Wash.), 100 μL of a dilution of 2991 μL Tetanus Toxoid solution plus 9 μL SEQ ID NO: 1 solution, 100 μL of a dilution of 2997 μL Tetanus Toxoid solution plus 3 μL SEQ ID NO: 1 solution, or 100 μL of a dilution of 6998.2 μL Tetanus Toxoid solution plus 1.8 μL SEQ ID NO: 1 solution. In parallel, control wells with identical number of the same cells were incubated with SEQ ID NO: 3 peptide solutions prepared as described for SEQ ID NO: 1. All plates were then incubated for six additional days. On assay day five, 100 μL of supernatant was removed from each well and replaced with freshly conditioned chRPMI.

Figure 8A:
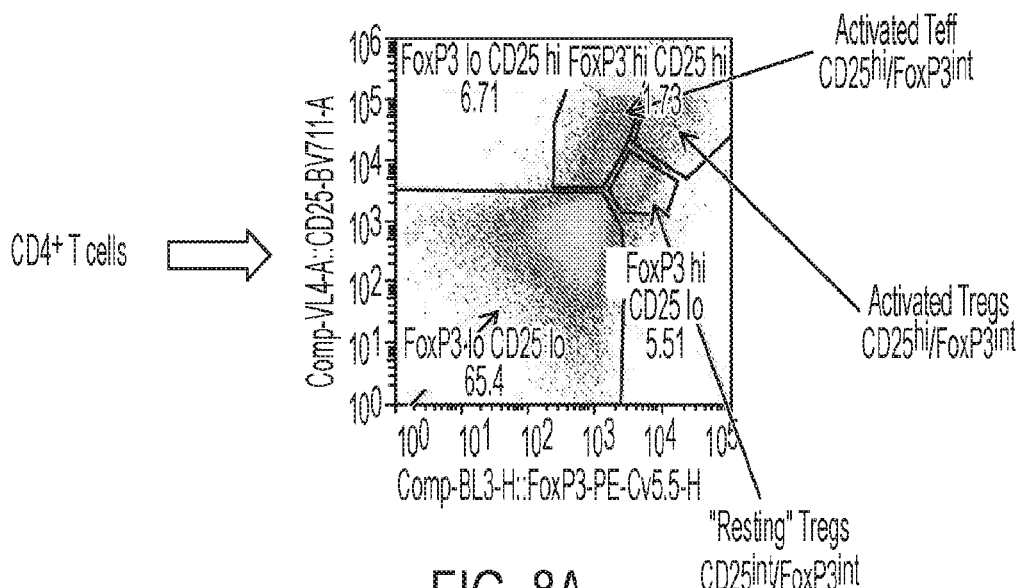
FIGS. 8A-B depicts the gating strategy for two measures of CD4+ T cell activation.

On assay day seven, cells were removed from incubation. Cells were labeled for live/dead discrimination, for surface markers CD127, CCR7, CD4, CD45RA, and CD25 and for intracellular FoxP3. Stained cells were further prepared for FACS analysis by conventional means. Cells were first gated to eliminate aggregates and dead cells. Live cells were gated for CD4 T cells and all subsequent analysis was done on this population. The activated Teffector population was identified as the $CD4_+/CD25$-high/FoxP3-intermediate ($CD4^+/CD25^{hu}/FoxP3^{int}$) (FIG. 8A). In a parallel analysis of this identified T effector cell population, it was shown that proliferation of this major population also corresponds to a CD45RA-low and CCR7-low effector memory T cells:

FIGS. 24A-D, demonstrate the gating strategy employed for the Bystander Suppression Assay and highlights the regulatory and activation markers in CD4 T cells stimulated by TT, and demonstrating that the major proliferations population corresponds to the T effector memory phenotype (CD45RA-low/CCR7-low).

Figure 8B:
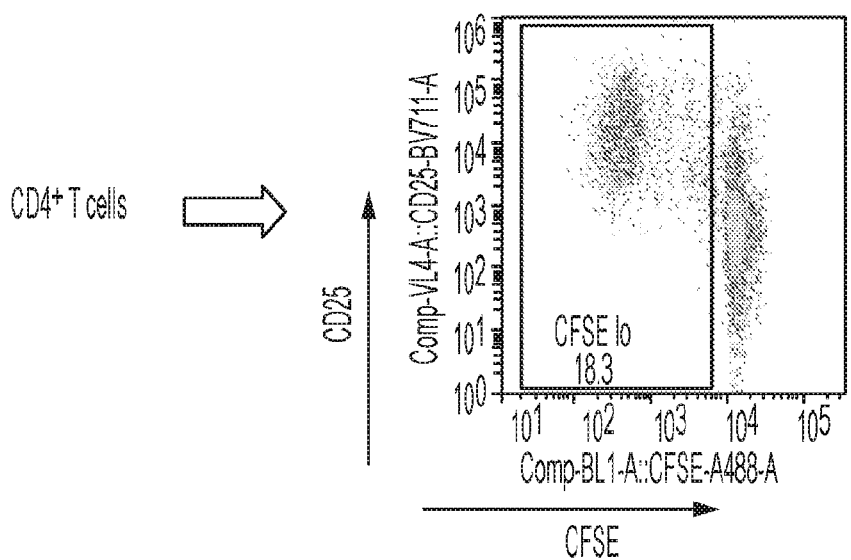

Proliferation of $CD4_+/CD25$-high ($CD4^+/CD25^{hi}$) T cells was estimated from the dilution of the CFSE stain (Cat #: 65-0850-84, Affymetrix, Santa Clara, Calif.) and % proliferation determined by the CFSE-low)($CFSE^{lo}$ population (FIG. 8B).

Example 5A. Peptide SEQ ID NO: 1 Suppressed Proliferation and Activation of CD4+ Effector T Cells The change in activation (FIG. 9) and proliferation (FIG. 10) of CD4+ effector cells when the proliferation stimulant (Tetanus Toxoid) is co-delivered with SEQ ID NO: 1 was measured and the proliferative response of $CD4_+$ T cells, comprised mainly of T effector memory cells, was characterized.

Figure 18:
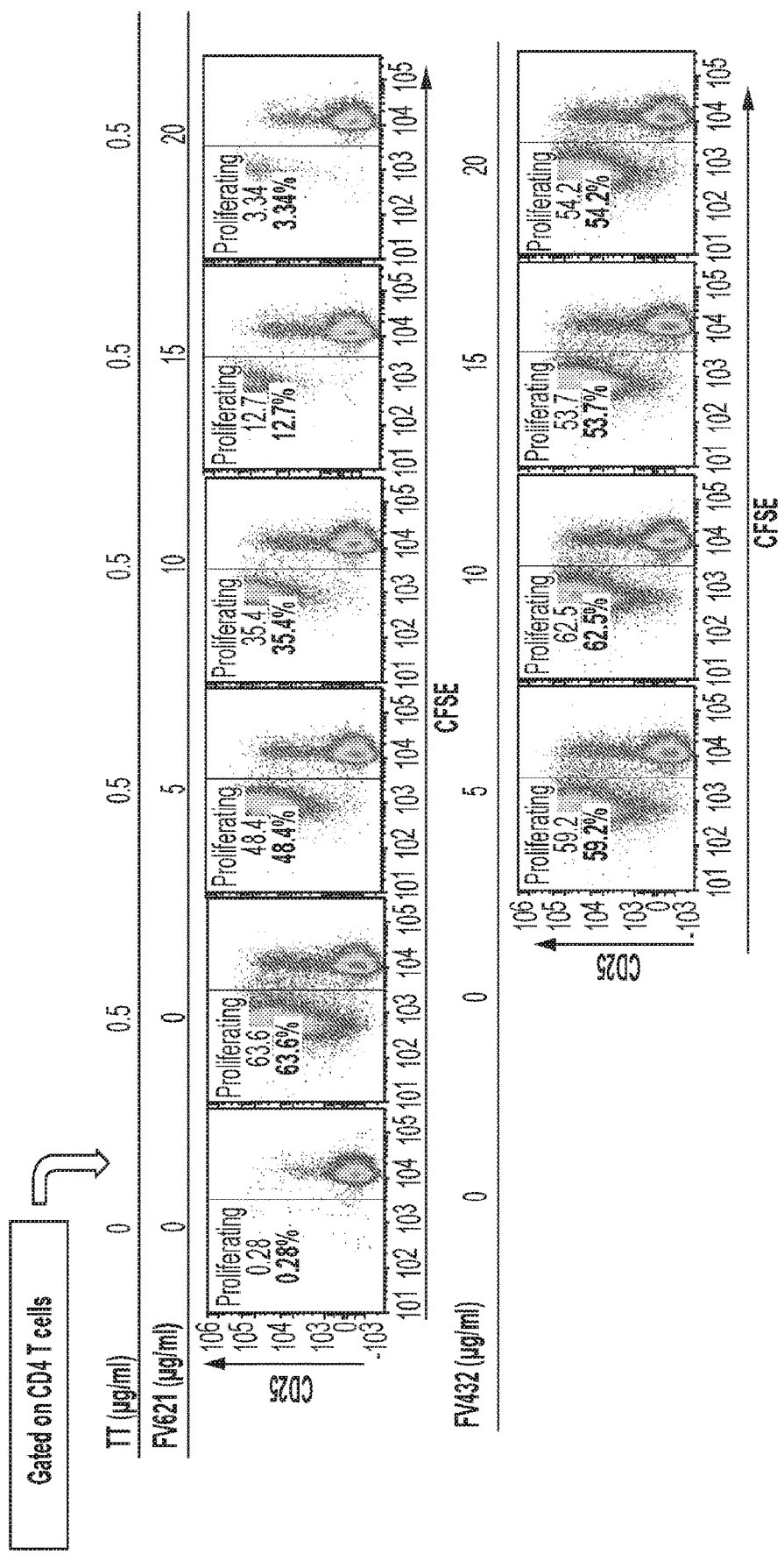
FIG. 18 shows that Tetanus Toxoid stimulated a population of activated (CD25 high) CD4 T cells to proliferate (CFSE low) (with approximately 90% of the activated cells also proliferating (data not shown)) and further shows that this population of highly activated cells is actively suppressed by SEQ ID NO:1 (shown as FV621) in a dose-dependent manner (FIG. 18, top row), while SEQ ID NO: 3 (shown as FV432) shows no significant inhibitory effect on activated CD4 cells (FIG. 18, bottom row).

T cell proliferation assays were performed on the Tregitopes of the present disclosure according to the methods described previously. Dot plots corresponding to each experimental condition tested for activation and proliferation are presented in FIG. 9 and FIG. 10, respectively. FIG. 9 shows that, in donor 114, peptide SEQ ID NO: 1 strongly suppressed a population of activated effector $CD4_+$ T cells ($CD4_+/CD25$-high/FoxP3-intermediate, shown as $CD4^+/CD25^{hi}/FoxP3^{int}$) reacting to Tetanus Toxoid (FIG. 9, lower row) in a dose-dependent manner, while control peptide SEQ ID NO: 3 had no appreciable effect (FIG. 9, upper row). In the same experiment, the proliferation of total $CD4_+$ T cells activated by peptide SEQ ID NO: 1 (CFSE low cells, shown as $CFSE^{lo}$, in FIG. 10) was strongly suppressed by peptide SEQ ID NO: 1 (FIG. 10, lower row) in a dose-dependent manner, while control peptide SEQ ID NO: 3 had little to no effect (FIG. 10, upper row). FIG. 18 demonstrates that Tetanus Toxoid stimulated a population of activated (CD25 high) CD4 T cells to proliferate (CFSE low), with approximately 90% of the activated cells also proliferating (data not shown). This population of highly activated cells is actively suppressed by SEQ ID NO:1 (shown as FV621) in a dose-dependent manner (FIG. 18, upper row), while SEQ ID NO: 3 (shown as FV432) shows no significant inhibitory effect on activated CD4 cells (FIG. 18, lower row).

Further, gating on CD4+ and CD4– live cells demonstrated that the inhibitory effect of SEQ ID NO: 1 on cell proliferation was more pronounced on the CD4+ population than on the CD4– population (FIG. 11). SEQ ID NO: 1 suppressed proliferation of CD4– T cells in a dose dependent manner (FIG. 11, lower row). Negative control peptide SEQ ID NO: 3 showed little inhibitory effect on the CD4– populations (FIG. 11, upper row).

Example 5B. Peptide SEQ ID NO: 1 and its FVIII Homologue Suppressed Proliferation of CD4+ Effector T Cells Additionally, the inhibitory effects of the Factor V derived Tregitope (SEQ ID NO: 1) with its Factor VIII homologue (SEQ ID NO: 2) on the $CD4_+$ T cell effector memory response to TT in PBMCs in normal donors was compared, analyzed and evaluated. FIG. 12 shows an alignment of peptides SEQ ID NO: 1 and SEQ ID NO: 2 displaying the homology between both peptide sequences.

Figure 13A:
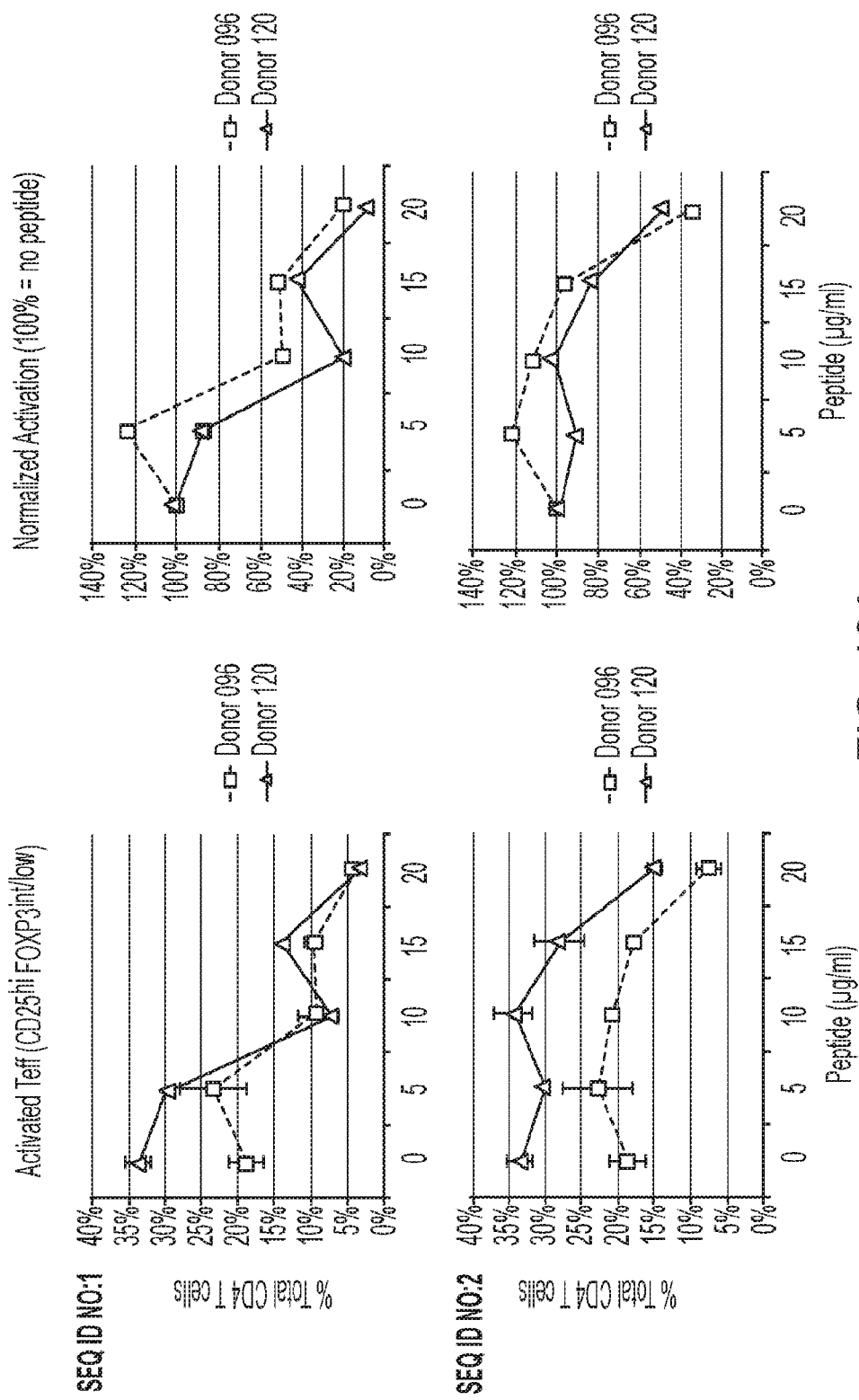
FIGS. 13A-B depicts the comparative inhibition of CD4+ T cell activation (FIG. 13A) and CD4+ T cell proliferation (FIG. 13B) by peptides SEQ ID NO: 1 (top row of both FIG. 13A and FIG. 13B) and SEQ ID NO: 2 (bottom row of FIG. 13A and FIG. 13B) across two donors.

A study designed to evaluate the effect of peptides SEQ ID NO: 1 and SEQ ID NO: 2 on the recall response to TT of PBMCs derived from two normal donors was undertaken. The protocol used is previously described. Tregitope concentrations ranged from 5, 10, 15, and 20 ug/ml. SEQ ID NO: 1 inhibited CD4+ T cell activation and proliferation of $T_{eff}$ responding to TT in a concentration-dependent manner (FIG. 13A (upper two panels) and FIG. 13B (upper two panels), respectively). As shown in FIG. 13A, for Donor 096, CD4+ T cell activation was reduced by 80% at 20 ug/ml (11 mM). Also as shown in FIG. 13A, for Donor 120, $CD4_+$ T cell activation was reduced by 90% at 20 ug/ml (11 mM). SEQ ID NO. 2 when added with TT, inhibited both CD4+ T cell memory responses (CD4+ T cell activation and proliferation of $T_{eff}$) in a concentration-dependent manner (FIG. 13A (lower two panels) and FIG. 13B (lower two panels), respectively). As shown in FIG. 13A, for donor 096, $CD4_+$ T cell activation was reduced by 70% at 20 ug/ml (11 mM).

Figure 13B:
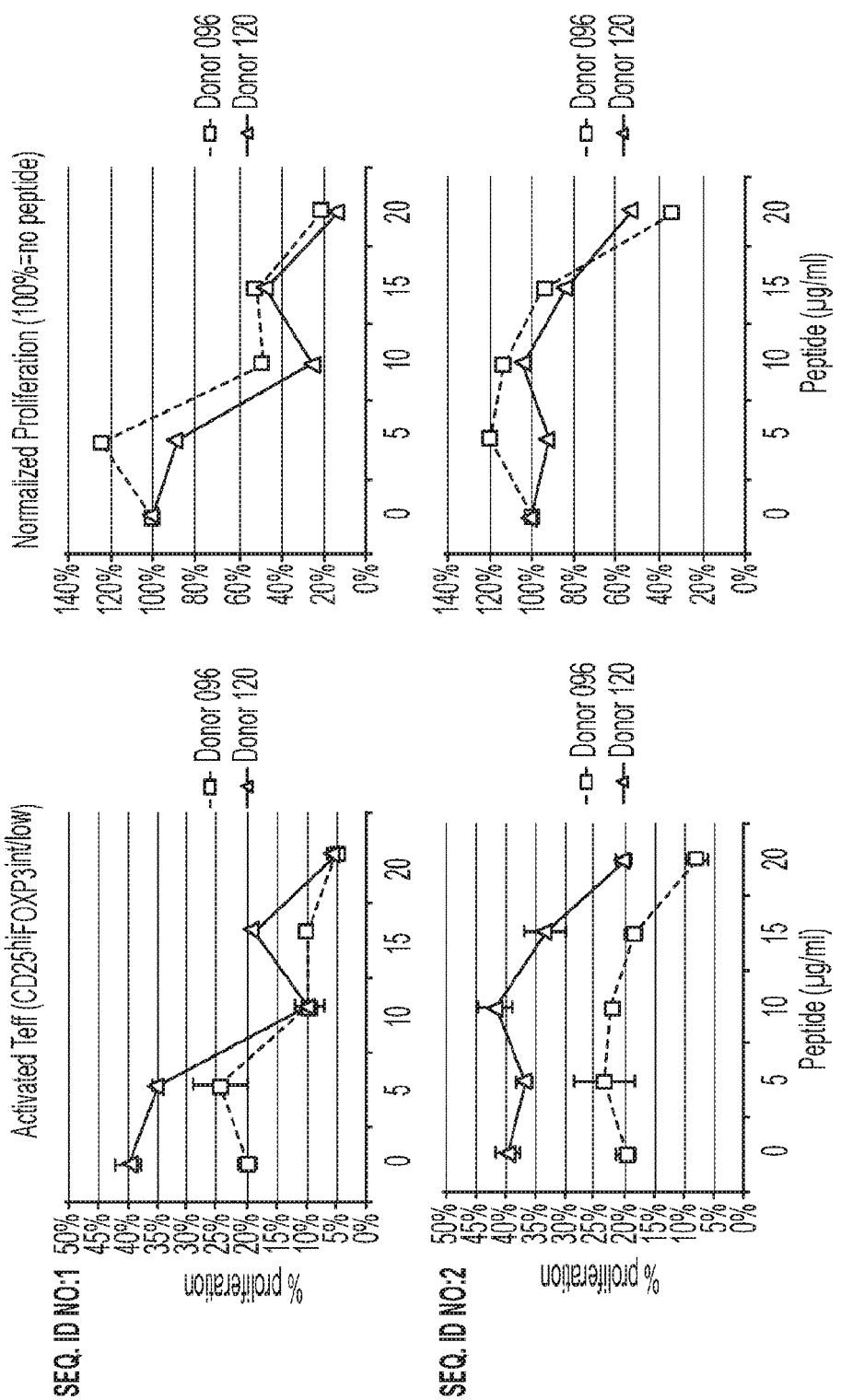

Also as shown in FIG. 13A, for Donor 120, CD4₊ T cell activation was reduced by 50% at 20 ug/ml (11 mM). As shown in FIG. 13B, in general, Donor 120 responded with a 5-20% stronger inhibitor effect (for both CD4+ proliferation and $T_{eff}$ activation) for a given peptide concentration of either SEQ ID NO: 1 (upper two panels) or SEQ ID NO. 2 (lower two panels) across the range of concentrations tested. The similarity in peptide sequence between the SEQ ID NO: 1 and its SEQ ID NO: 2 homolog, along with their parallel T cell inhibitory function, evidences that antigen-specific tolerance to FV is a useful method to stimulate tolerance to a homologous replacement protein, such as FVIII in Hemophilia A patients. In this assay, both SEQ ID NO: 1 and SEQ ID NO: 2 suppressed proliferation of CD4+ T cells and activated T effector T cells in a dose dependent manner.

(6) Methods for Assessing SEQ ID NO: 1 Peptide Effects on CD8+ Effector T Cells.

CD8+ effector memory T cells contained within PBMC cell populations can be induced to proliferate in response to stimulation with known class I T cell epitopes. SEQ ID NO: 1 binds multiple HLA alleles and induces a regulatory phenotype in exposed APC (Clinical Partners, Johnston, R.I.) (the gating strategy employed allows for the identification of the APC fraction in PBMC collected from the whole blood donors). The results of this assay establish the ability of SEQ ID NO: 1 to suppress the proliferation of antigen stimulated $CD8_+$ T effector memory T cells by either direct (engagement and activation of $T_{Reg}$) or indirect (modulation of APC phenotype) means.

T cell proliferation assays were performed on the Tregitopes of the present disclosure according to the methods described previously. PBMCs from two healthy donors were thawed and suspended in conditioned chRPMI ($3.3 \times 10^6$ cells/mL) by conventional means. Cells were stained with CFSE (Cat #: 65-0850-84, Affymetrix, Santa Clara, CA) and plated at 300,000 cells per well. Plates were incubated overnight (37° C. in 5% $CO_2$). On assay day 1, SEQ ID NO: 1 was re-constituted in sterile DMSO yielding a final stock concentration of 20 mg/mL. Intermediate solutions of SEQ ID NO: 1 at twice the final concentration in chRPMI were prepared as described previously. Final concentration of SEQ ID NO: 1 tested from 2.5, 5, 10 and 20 ug/ml. As a CD8+ stimulating antigen, the CEF peptide pool which consists of 23 MHC class I restricted viral epitopes derived from human cytomegalovirus, Epstein-Barr virus and influenza virus was used. CEF peptides were added to the wells (data shown for 2 μg/mL) with cells and media (control) or SEQ ID NO: 1 at 0, 1, 2 or 4 ug/ml. All plates were incubated for six additional days. On assay day 5, 100 uL of supernatant was removed from each well and replaced with freshly conditioned chRPMI.

Conventional methods were used to stain cells for live/dead marker, extracellular markers CD4, CD8α and CD25, CD127, CD45RA and CCR7, and intracellular marker FoxP3. After FACS analysis, cells were gated to eliminate aggregates and dead cells. On the live cells population, CD8a and CD4 cells were gated separately and each population was analyzed for proliferation (CFSE low population) or activation (CD25-high/FoxP3 low/intermediate, shown as FoxP3int_lo CD25hi) as explained previously.

Figure 14:
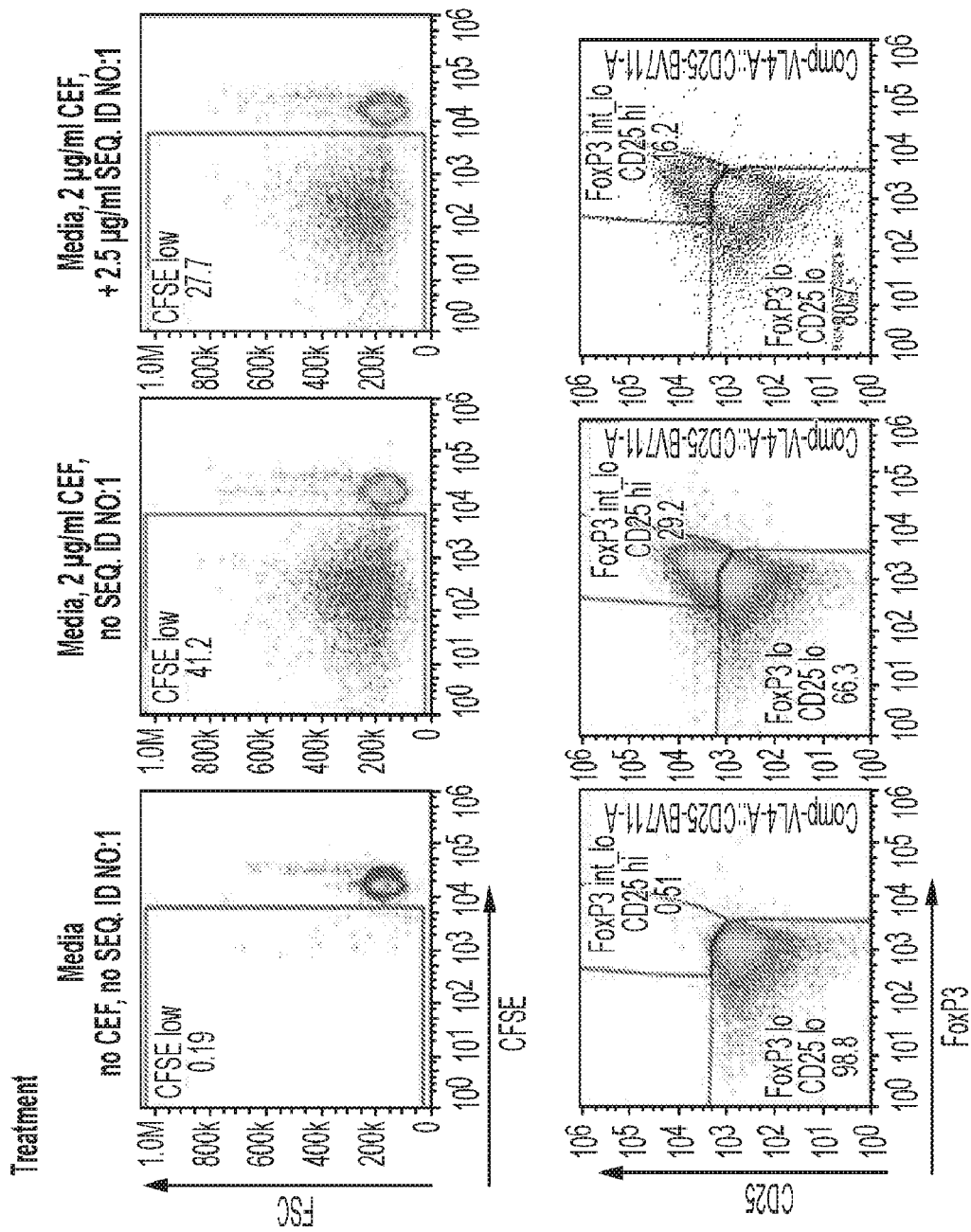
FIG. 14 illustrates the effect of SEQ ID NO: 1 on CD8+ T cell proliferation (top row) and activation (bottom row) for Donor 121.
Figure 14:
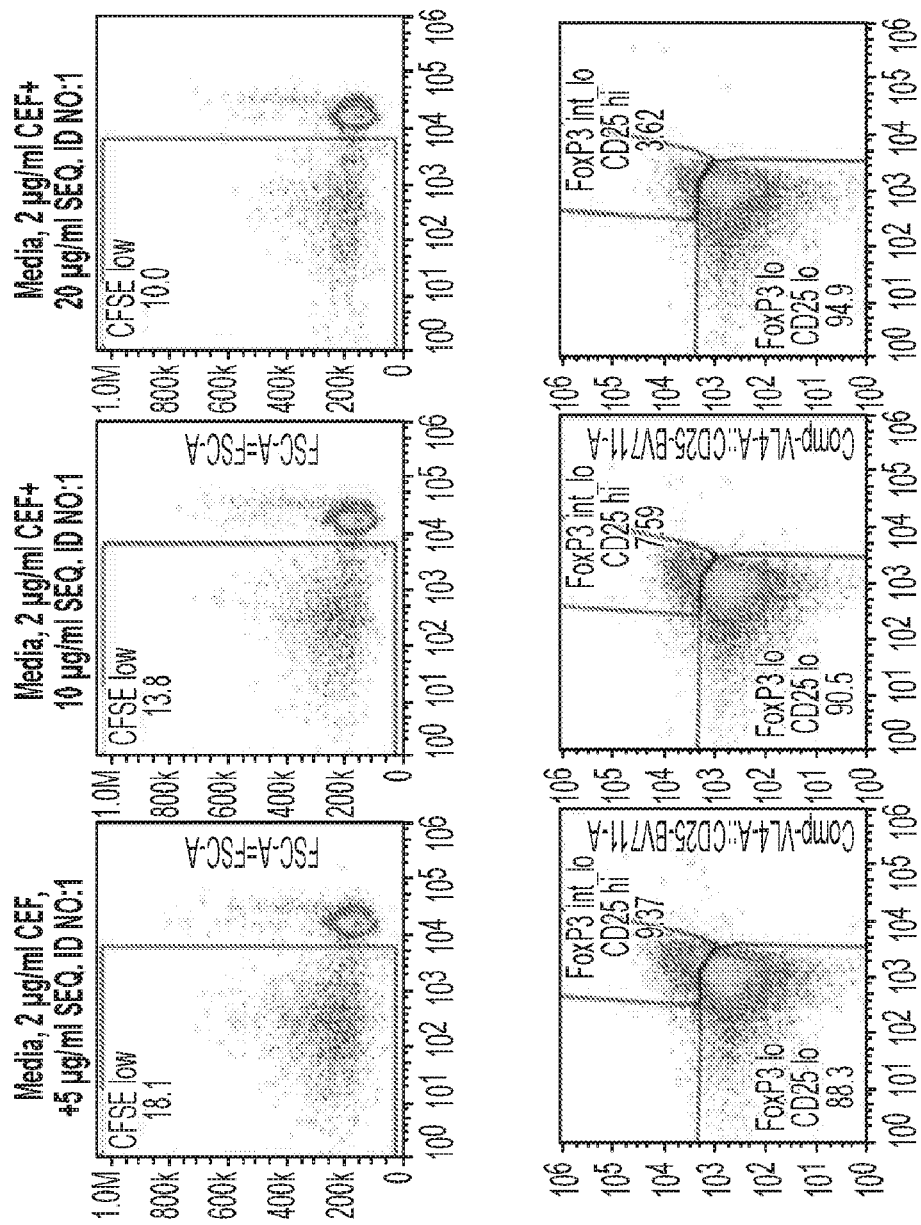
Figure 15:
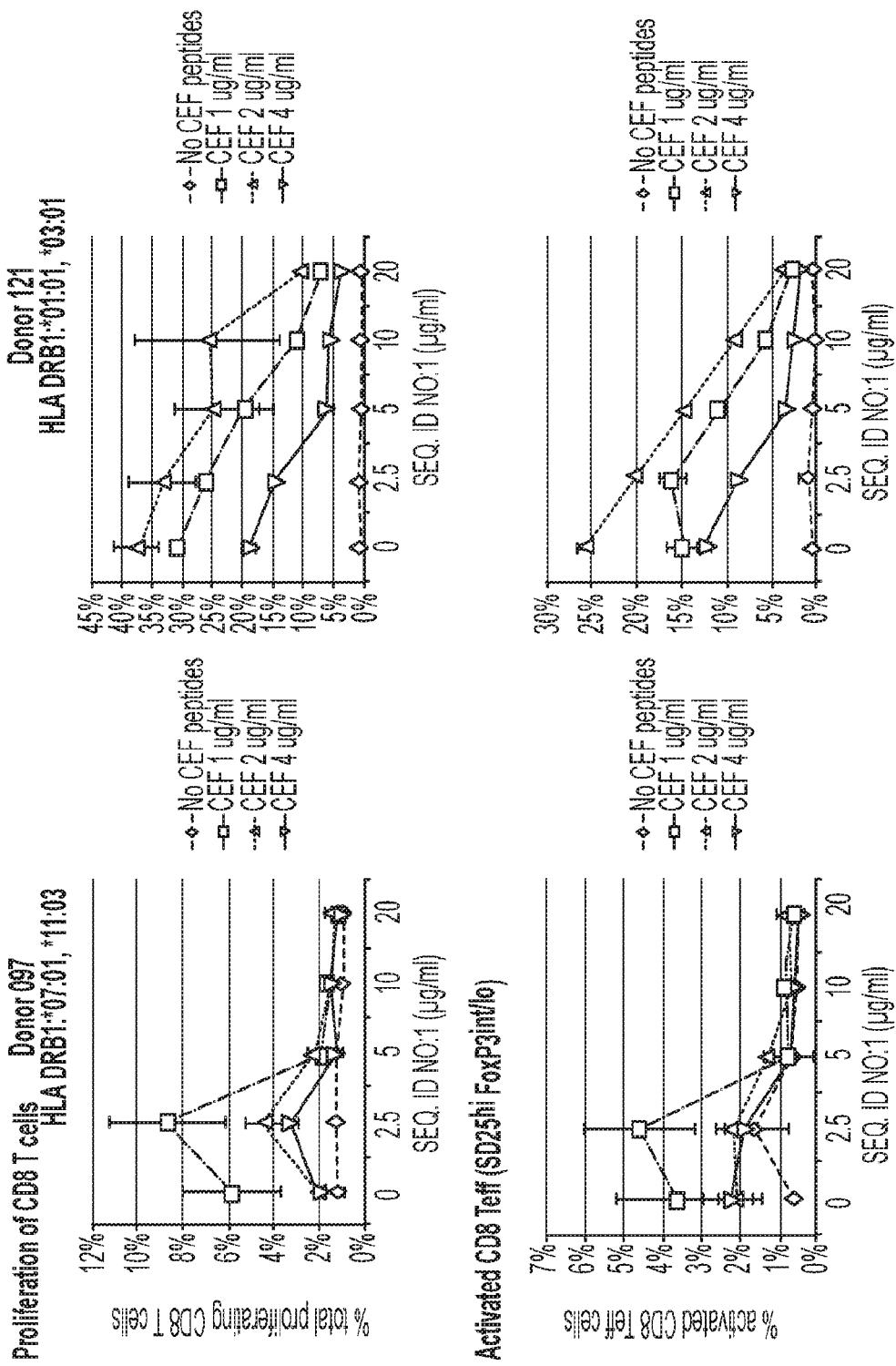
FIG. 15 shows the effect of peptide SEQ ID NO: 1 on CD8+ T cell proliferation (top row) and activation (bottom row) for Donors 097 and 121.

Example 6. Peptide SEQ ID NO: 1 Suppressed Proliferation of CD8+ Effector T Cells The potential inhibition of $CD8_+$ T cell response by SEQ ID NO: 1 when PBMC from healthy donors are stimulated with CEF peptides mixture was tested. FIG. 14 shows that SEQ ID NO: 1 strongly inhibits the $CD8_+$ T cell proliferative response to CEF peptides (upper row), as well as activation of $CD8_+$ cells (lower row). FIG. 15 shows that the percent of proliferating $CD8_+$ T cells (CFSE low) (upper two panels) and the percent of activated $CD8_+$ T effector cells ($CD25^{hi}$ $FoxPr^{int/lo}$) (lower two panels), decreases with increasing concentrations of SEQ ID NO: 1, demonstrating that SEQ ID NO: 1 also has an inhibitory effect on the $CD8_+$ T cell population. In both cases, SEQ ID NO: 1 strongly inhibited the response in a dose-dependent manner.

(7) Methods for Assessing Peptide Effects on Immune Response (GvHD)

Bone marrow transplant is a procedure whereby unhealthy bone marrow is replaced with donated healthy bone marrow. Bone marrow transplants can be used to treat patients with life-threatening blood cancers like leukemia (Vincente D et al., (2007), Bone Marrow Transplant, 40(4): 349-54), diseases which result in bone marrow failure like aplastic anemia (Champlin RE et al., (2007), Blood, 109 (10):4582-5), and other immune system or genetic diseases (Chinen J and Bucley R H, (2010), J Allergy Clin Immunol, 125(2 Suppl 2):S324-35). Graft versus host disease (GvHD) is known as a major complication in bone marrow transplantation and is characterized by immediate and high mortality after onset (Lee SJ et al., (2003), Biol Blood Marrow Transplant, 9(4):215-33). In GvHD, severe tissue damage is caused by donor lymphocytes as they make their way from transplanted donor tissue to HLA-mismatched recipient tissues. Symptoms include severe damage in various organs such as skin, lungs, liver and intestines caused by infusion in the recipient (Goker H et al., (2001), Exp Hematol, 29(3):259-77).

It was observed by EpiVax (Providence, R.I.) that transplantation of human peripheral blood mononuclear cells (PBMCs) (obtained from leukopaks (Hemacare, Van Nuys, CA)) into an immune deficient mouse causes a GvHD-like syndrome resulting in death by 20-50 days. In this model, T cells contained within the transplanted PBMC infiltrate the host mouse's skin, liver, intestine, lungs and kidneys causing severe damage and ultimately death. Immunodeficient mouse strain NOD-scid IL-2Rγ$^{null}$ (NSG-Jax stock #005557) (The Jackson Laboratory, Bar Harbor, Me.) mice and transplants of human PBMC were used to assess the impact of SEQ ID NO: 1 on the progression of GvHD. On assay day −1, mice were grouped by weight into matched treatment and control groups (Table 7) and then irradiated with 100 cGy from an X-ray irradiator source (Lifespan Hospital, Providence, R.I.). After 6 hours of irradiation, mice subjects received 10 million hPBMCs IV via the tail vein. The mice in Group 8 received irradiation, but no PBMCs. Starting on assay day 0 and continuing through assay day 25, subject mice were dosed according to schedule outlined in Table 4.

Clinical observations, including weight loss, posture, activity, and appearance of hair coat and skin, were made three times per week. A subject mouse was euthanized if it exhibited a >20% weight loss from the starting date or exhibited a combination of the following clinical signs: (i) a 10-20% weight loss from the starting date (ii) coldness to touch (iii) lethargy with a hunched posture and scruffy coat.

TABLE 4

Experimental groups and dosing schedule for GVHD study

| Group | Mice | PBMC | Test Articles | Dose amount | Dosing frequency |
|---|---|---|---|---|---|
| 1 | 3 | + | PBS (disease control) | 300 μl PBS | Days 0, 2, 4, 7, 10, 15, 20, 25 |
| 2 | 10 | + | PBS + DMSO (vehicle) | 0.5% DMSO | Days 0, 2, 4, 7, 10, 15, 20, 25 |

TABLE 4-continued

Experimental groups and dosing schedule for GVHD study

| Group | Mice | PBMC | Test Articles | Dose amount | Dosing frequency |
|---|---|---|---|---|---|
| 6 | 10 | + | SEQ ID NO: 1 | 20 μg | Days 0, 2, 4, 7, 10, 15, 20, 25 |
| 7 | 7 | + | IVIG (positive control) | 50 mg | Days 0, 7, 14, 21, 28 |
| 8 | 3 | − | None (control group) | NA | |

Figure 16B:
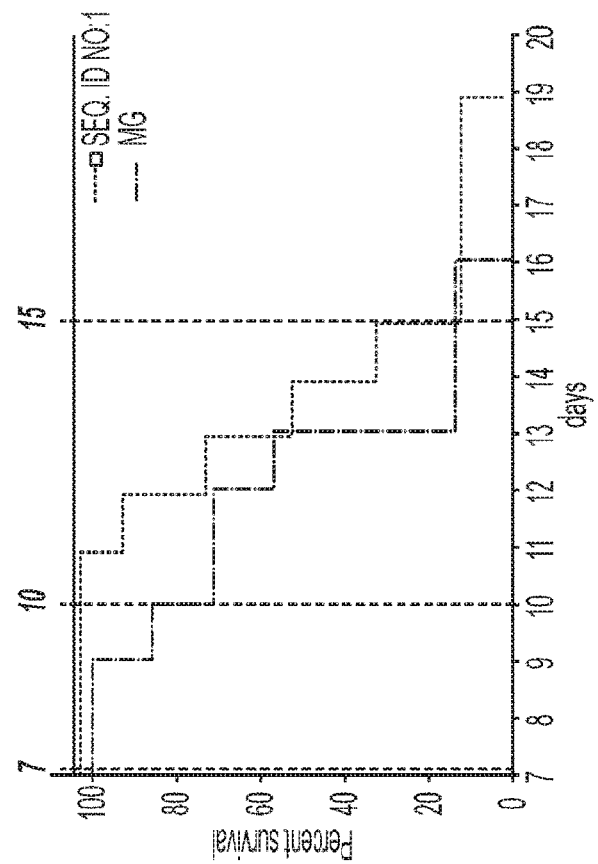
FIGS. 16A-B summarize the survival plots for peptide SEQ ID NO: 1 showing a favorable survival profile over both negative controls (FIG. 16A) and positive controls (FIG. 16B).
Figure 16A:
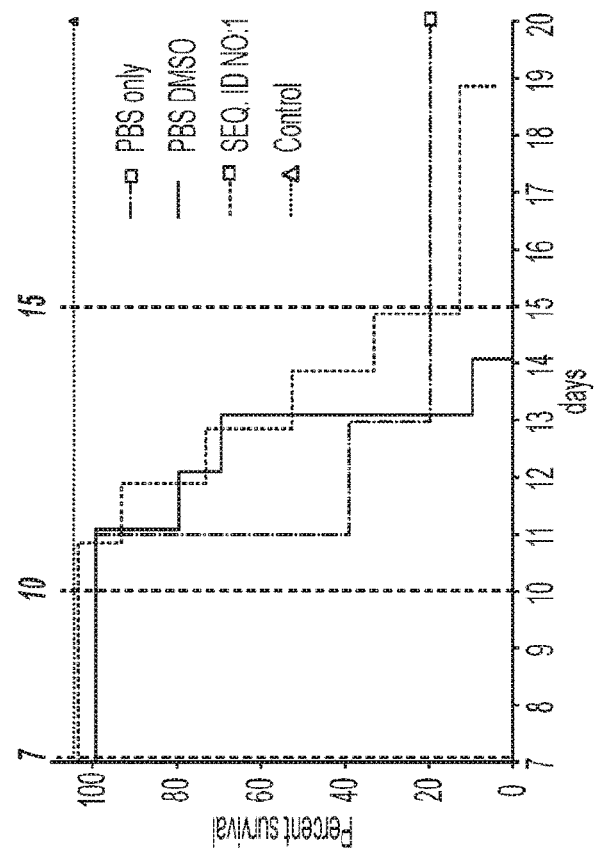

Example 7. SEQ ID NO: 1 Inhibited the Development of GvHD in Xenogenic GvHD Model The transplantation of human lymphocytes into immunodeficient mice and subsequent treatment with SEQ ID NO: 1 enabled the assessment of SEQ ID NO: 1 on immune function in this in vivo model. SEQ ID NO: 1 suppressed T-cell activation thus slowing the progression of the disease. The main evaluation criteria used to evaluate was survival of the test subjects. A delay in the development of GvHD for the group treated with SEQ ID NO: 1 was observed as suggested by the Kaplan-Meiers Survival Curve. FIGS. 16A-B evidence that treatment with SEQ ID NO: 1 resulted in extended survival relative to negative controls (FIG. 16A) and the positive control IVIG (FIG. 16B).

Example 8. Generation of a FVIII-Tregitope Construct

Fusion of Tregitope with an immunogenic protein can lead to the induction of peripheral tolerance of the immunogenic protein. Clotting Factor VIII is immunogenic in people with severe hemophilia A. In one exemplary method of producing such constructs, chimeric constructs comprised of the coding sequence of Factor VIII and Tregitope are produced (Sambrook et al., Molecular Cloning: A Laboratory Manual, 2 ed., Cold Spring Harbor Laboratory Press, (1989)). Briefly, the Factor VIII coding region fused at the carboxy-terminus and/or amino-terminus to a Tregitope is generated by annealing overlapping oligos and sub-cloned into an expression plasmid. A Tregitope may also be inserted into Factor VII, e.g. by mutagenesis (i.e., site-directed mutagenesis). The plasmids are transfected into DG44 CHO cells and stable transfectants selected. The chimeric protein is purified over an immunoaffinity column and evaluated for tolerogenicity. Tables 5-8 illustrates exemplary embodiments of such proteins (e.g., a chimeric protein).

TABLE 5

Factor VIII-Tregitope: SEQ ID NO: 69 (Tregitope bold)

MQIELSTCFFLCLLRFCFSATRRYYLGAVELSWDYMQSDLGELPVDARFP
PRVPKSFPFNTSVVYKKTLFVEFTDHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKM
HTVNGTVNRSLPGLIGCHRKSVYWHVIGMGTTPEVHSIFLEGHTFLVRNH
RQASLEISPITFLTAQTLLMDLGQFLLFCHISSHQHDGMEAYVKCDSCPE
EPQLRMKNNEEAEDYDDDLTDSEMDVVRFDDDNSPSFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE

TABLE 5-continued

Factor VIII-Tregitope: SEQ ID NO: 69 (Tregitope bold)

NRSWYLTENIQRFLPNPAGVQLEDPEFQASNIMHSINGYVFDSLQLSVCL
HEVAYWYILSIGAQTDFLSVFFSGYTFKHKMVYEDTLTLFPFSGETVFMS
MENPGLWILGCHNSDFRNRGMTALLKVSSCDKNTGDYYEDSYEDISAYLL
SKNNAIEPRSFSQNSRHPSTRQKQFNATTIPENDIEKTDPWFAHRTPMPK
IQNVSSSDLLMLLRQSPTPHGLSLSDLQEAKYETFSDDPSPGAIDSNNSL
SEMTHFRPQLHHSGDMVFTPESGLQLRLNEKLGTTAATELKKLDFKVSST
SNNLISTIPSDNLAAGTDNTSSLGPPSMPVHYDSQLDTTLFGKKSSPLTE
SGGPLSLSEENNDSKLLESGLMNSQESSWGKNVSSTESGRLFKGKRAHGP
ALLTKDNALFKVSISLLKTNKTSNNSATNRKTHIDGPSLLIENSPSVWQN
ILESDTEFKKVTPLIHDRMLMDKNATALRLNHMSNKTTSSKNMEMVQQKK
EGPIPPDAQNPDMSFFKMLFLPESARWIQRTHGKNSLNSGQGPSPKQLVS
LGPEKSVEGQNFLSEKNKVVVGKGEFTKDVGLKEMVFPSSRNLFLTNLDN
LHENNTHNQEKKIQEEIEKKETLIQENVVLPQIHTVTGTKNFMKNLFLLS
TRQNVEGSYDGAYAPVLQDFRSLNDSTNRTKKHTAHFSKKGEEENLEGLG
NQTKQIVEKYACTTRISPNTSQQNFVTQRSKRALKQFRLPLEETELEKRI
IVDDTSTQWSKNMKHLTPSTLTQIDYNEKEKGAITQSPLSDCLTRSESIP
QANRSPLPIAKVSSFPSIRPIYLTRVLFQDNSSNLPAASYRKKDSGVQES
SHFLQGAKKNNLSLAILTLEMTGDQREVGSLGTSATNSVTYKKVENTVLP
KPDLPKTSGKVELLPKVHIYQKDLFPTETSNGSPGHLDLVEGSLLQGTEG
AIKWNEANRPGKVPFLRVATESSAKTPSKLLDPLAWDNHYGTQIPKEEWK
SQEKSPEKTAFKKKDTILSLNACESNHAIAAINEGQNKPEIEVTWAKQGR
TERLCSQNPPVLKRHQREITRTTLQSDQEEIDYDDTISVEMKKEDFDIYD
EDENQSPRSFQKKTRHYFIAAVERLWDYGMSSSPHVLRNRAQSGSVPQFK
KVVFQEFTDGSFTQPLYRGELNEHLGLLGPYIRAEVEDNIMVTFRNQASR
PYSFYSSLISYEEDQRQGAEPRKNFVKPNETKTYFWKVQHHMAPTKDEFD
CKAWAYFSDVDLEKDVHSGLIGPLLVCHTNTLNPAHGRQVTVQEFALFFT
IFDETKSWYFTENMERNCRAPSNIQMEDPTFKENYRFHAINGYIMDTLFG
LVMAQDQRIRWYLLSMGSNENIHSIHFSGHVFTVRKKEEYKMALYNLYPG
VFETVEMLPSKAGIWRVECLIGEHLHAGMSTLFLVYSNKCQTPLGMASGH
IRDFQITASGQYGQWAPKLARLHYSGSINAWSTKEPFSWIKVDLLAPMII
HGIKTQGARQKFSSLYISQFIIMYSLDGKKWQTYRGNSTGTLMVFFGNVD
SSGIKHNIFNPPIIARYIRLHPTHYSIRSTLRMELMGCDLNSCSMPLGME
SKAISDAQITASSYFTNMFATWSPSKARLHLQGRSNAWRPQVNNPKEWLQ
VDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDL
YILTIHFTGHSFIYGK

TABLE 6

Factor VIII-Tregitope: SEQ ID NO: 70 (Tregitope bold)

ILTIHFTGHSFIYGKMQIELSTCFFLCLLRFCFSATRRYYLGAVELSWDY
MQSDLGELPVDARFPPRVPKSFPFNTSVVYKKTLFVEFTDHLFNIAKPRP
PWMGLLGPTIQAEVYDTVVITLKNMASHPVSLHAVGVSYWKASEGAEYDD
QTSQREKEDDKVFPGGSHTYVWQVLKENGPMASDPLCLTYSYLSHVDLVK
DLNSGLIGALLVCREGSLAKEKTQTLHKFILLFAVFDEGKSWHSETKNSL
MQDRDAASARAWPKMHTVNGTVNRSLPGLIGCHRKSVYWHVIGMGTTPEV
HSIFLEGHTFLVRNHRQASLEISPITFLTAQTLLMDLGQFLLFCHISSHQ
HDGMEAYVKCDSCPEEPQLRMKNNEEAEDYDDDLTDSEMDVVRFDDDNSP
SFIQIRSVAKKHPKTWVHYIAAEEEDWDYAPLVLAPDDRSYKSQYLNNGP
QRIGRKYKKVRFMAYTDETFKTREAIQHESGILGPLLYGEVGDTLLIIFK
NQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQI
MSDKRNVILFSVFDENRSWYLTENIQRFLPNPAGVQLEDPEFQASNIMHS
INGYVFDSLQLSVCLHEVAYWYILSIGAQTDFLSVFFSGYTFKHKMVYED
TLTLFPFSGETVFMSMENPGLWILGCHNSDFRNRGMTALLKVSSCDKNTG
DYYEDSYEDISAYLLSKNNAIEPRSFSQNSRHPSTRQKQFNATTIPENDI
EKTDPWFAHRTPMPKIQNVSSSDLLMLLRQSPTPHGLSLSDLQEAKYETF
SDDPSPGAIDSNNSLSEMTHFRPQLHHSGDMVFTPESGLQLRLNEKLGTT
AATELKKLDFKVSSTSNNLISTIPSDNLAAGTDNTSSLGPPSMPVHYDSQ
LDTTLFGKKSSPLTESGGPLSLSEENNDSKLLESGLMNSQESSWGKNVSS
TESGRLFKGKRAHGPALLTKDNALFKVSISLLKTNKTSNNSATNRKTHID
GPSLLIENSPSVWQNILESDTEFKKVTPLIHDRMLMDKNATALRLNHMSN
KTTSSKNMEMVQQKKEGPIPPDAQNPDMSFFKMLFLPESARWIQRTHGKN
SLNSGQGPSPKQLVSLGPEKSVEGQNFLSEKNKVVVGKGEFTKDVGLKEM
VFPSSRNLFLTNLDNLHENNTHNQEKKIQEEIEKKETLIQENVVLPQIHT
VTGTKNFMKNLFLLSTRQNVEGSYDGAYAPVLQDFRSLNDSTNRTKKHTA
HFSKKGEEENLEGLGNQTKQIVEKYACTTRISPNTSQQNFVTQRSKRALK
QFRLPLEETELEKRIIVDDTSTQWSKNMKHLTPSTLTQIDYNEKEKGAIT
QSPLSDCLTRSESIPQANRSPLPIAKVSSFPSIRPIYLTRVLFQDNSSNL
PAASYRKKDSGVQESSHFLQGAKKNNLSLAILTLEMTGDQREVGSLGTSA
TNSVTYKKVENTVLPKPDLPKTSGKVELLPKVHIYQKDLFPTETSNGSPG
HLDLVEGSLLQGTEGAIKWNEANRPGKVPFLRVATESSAKTPSKLLDPLA

TABLE 6-continued

Factor VIII-Tregitope: SEQ ID NO: 70 (Tregitope bold)

WDNHYGTQIPKEEWKSQEKSPEKTAFKKKDTILSLNACESNHAIAAINEG
QNKPEIEVTWAKQGRTERLCSQNPPVLKRHQREITRTTLQSDQEEIDYDD
TISVEMKKEDFDIYDEDENQSPRSFQKKTRHYFIAAVERLWDYGMSSSPH
VLRNRAQSGSVPQFKKVVFQEFTDGSFTQPLYRGELNEHLGLLGPYIRAE
VEDNIMVTFRNQASRPYSFYSSLISYEEDQRQGAEPRKNFVKPNETKTYF
WKVQHHMAPTKDEFDCKAWAYFSDVDLEKDVHSGLIGPLLVCHTNTLNPA
HGRQVTVQEFALFFTIFDETKSWYFTENMERNCRAPSNIQMEDPTFKENY
RFHAINGYIMDTLFGLVMAQDQRIRWYLLSMGSNENIHSIHFSGHVFTVR
KKEEYKMALYNLYPGVFETVEMLPSKAGIWRVECLIGEHLHAGMSTLFLV
YSNKCQTPLGMASGHIRDFQITASGQYGQWAPKLARLHYSGSINAWSTKE
PFSWIKVDLLAPMIIHGIKTQGARQKFSSLYISQFIIMYSLDGKKWQTYR
GNSTGTLMVFFGNVDSSGIKHNIFNPPIIARYIRLHPTHYSIRSTLRMEL
MGCDLNSCSMPLGMESKAISDAQITASSYFTNMFATWSPSKARLHLQGRS
NAWRPQVNNPKEWLQVDFQKTMKVTGVTTQGVKSLLTSMYVKEFLISSSQ
DGHQWTLFFQNGKVKVFQGNQDSFTPVVNSLDPPLLTRYLRIHPQSWVHQ
IALRMEVLGCEAQDLY

TABLE 7

Factor VIII-Tregitope: SEQ ID NO: 71 (Tregitope bold)

MQIELSTCFFLCLLRFCFSATRRYYLGAVELSWDYMQSDLGELPVDARFP
PRVPKSFPFNTSVVYKKTLFVEFTDHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKM
HTVNGTVNRSLPGLIGCHRKSVYWHVIGMGTTPEVHSIFLEGHTFLVRNH
RQASLEISPITFLTAQTLLMDLGQFLLFCHISSHQHDGMEAYVKCDSCPE
EPQLRMKNNEEAEDYDDDLTDSEMDVVRFDDDNSPSFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCL
HEVAYWYILSIGAQTDFLSVFFSGYTFKHKMVYEDTLTLFPFSGETVFMS
MENPGLWILGCHNSDFRNRGMTALLKVSSCDKNTGDYYEDSYEDISAYLL
SKNNAIEPRSFSQNSRHPSTRQKQFNATTIPENDIEKTDPWFAHRTPMPK
IQNVSSSDLLMLLRQSPTPHGLSLSDLQEAKYETFSDDPSPGAIDSNNSL
SEMTHFRPQLHHSGDMVFTPESGLQLRLNEKLGTTAATELKKLDFKVSST
SNNLISTIPSDNLAAGTDNTSSLGPPSMPVHYDSQLDTTLFGKKSSPLTE
SGGPLSLSEENNDSKLLESGLMNSQESSWGKNVSSTESGRLFKGKRAHGP
ALLTKDNALFKVSISLLKTNKTSNNSATNRKTHIDGPSLLIENSPSVWQN
ILESDTEFKKVTPLIHDRMLMDKNATALRLNHMSNKTTSSKNMEMVQQKK
EGPIPPDAQNPDMSFFKMLFLPESARWIQRTHGKNSLNSGQGPSPKQLVS
LGPEKSVEGQNFLSEKNKVVVGKGEFTKDVGLKEMVFPSSRNLFLTNLDN
LHENNTHNQEKKIQEEIEKKETLIQENVVLPQIHTVTGTKNFMKNLFLLS
TRQNVEGSYDGAYAPVLQDFRSLNDSTNRTKKHTAHFSKKGEEENLEGLG
NQTKQIVEKYACTTRISPNTSQQNFVTQRSKRALKQFRLPLEETELEKRI
IVDDTSTQWSKNMKHLTPSTLTQIDYNEKEKGAITQSPLSDCLTRSESIP
QANRSPLPIAKVSSFPSIRPIYLTRVLFQDNSSNLPAASYRKKDSGVQES
SHFLQGAKKNNLSLAILTLEMTGDQREVGSLGTSATNSVTYKKVENTVLP
KPDLPKTSGKVELLPKVHIYQKDLFPTETSNGSPGHLDLVEGSLLQGTEG
AIKWNEANRPGKVPFLRVATESSAKTPSKLLDPLAWDNHYGTQIPKEEWK
SQEKSPEKTAFKKKDTILSLNACESNHAIAAINEGQNKPEIEVTWAKQGR
TERLCSQNPPVLKRHQREITRTTLQSDQEEIDYDDTISVEMKKEDFDIYD
EDENQSPRSFQKKTRHYFIAAVERLWDYGMSSSPHVLRNRAQSGSVPQFK
KVVFQEFTDGSFTQPLYRGELNEHLGLLGPYIRAEVEDNIMVTFRNQASR
PYSFYSSLISYEEDQRQGAEPRKNFVKPNETKTYFWKVQHHMAPTKDEFD
CKAWAYFSDVDLEKDVHSGLIGPLLVCHTNTLNPAHGRQVTVQEFALFFT
IFDETKSWYFTENMERNCRAPSNIQMEDPTFKENYRFHAINGYIMDTLFG
LVMAQDQRIRWYLLSMGSNENIHSIHFSGHVFTVRKKEEYKMALYNLYPG
VFETVEMLPSKAGIWRVECLIGEHLHAGMSTLFLVYSNKCQTPLGMASGH
IRDFQITASGQYGQWAPKLARLHYSGSINAWSTKEPFSWIKVDLLAPMII
HGIKTQGARQKFSSLYISQFIIMYSLDGKKWQTYRGNSTGTLMVFFGNVD
SSGIKHNIFNPPIIARYIRLHPTHYSIRSTLRMELMGCDLNSCSMPLGME
SKAISDAQITASSYFTNMFATWSPSKARLHLQGRSNAWRPQVNNPKEWLQ
VDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDL
YIHSIHFSGHVFTVRK

TABLE 8

Factor VIII-Tregitope: SEQ ID NO: 72 (Tregitope bold)

IHSIHFSGHVFTVRKMQIELSTCFFLCLLRFCFSATRRYYLGAVELSWDY
MQSDLGELPVDARFPPRVPKSFPFNTSVVYKKTLFVEFTDHLFNIAKPRP
PWMGLLGPTIQAEVYDTVVITLKNMASHPVSLHAVGVSYWKASEGAEYDD
QTSQREKEDDKVFPGGSHTYVWQVLKENGPMASDPLCLTYSYLSHVDLVK
DLNSGLIGALLVCREGSLAKEKTQTLHKFILLFAVFDEGKSWHSETKNSL
MQDRDAASARAWPKMHTVNGTVNRSLPGLIGCHRKSVYWHVIGMGTTPEV
HSIFLEGHTFLVRNHRQASLEISPITFLTAQTLLMDLGQFLLFCHISSHQ
HDGMEAYVKCDSCPEEPQLRMKNNEEAEDYDDDLTDSEMDVVRFDDDNSP
SFIQIRSVAKKHPKTWVHYIAAEEEDWDYAPLVLAPDDRSYKSQYLNNGP
QRIGRKYKKVRFMAYTDETFKTREAIQHESGILGPLLYGEVGDTLLIIFK
NQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQI
MSDKRNVILFSVFDENRSWYLTENIQRFLPNPAGVQLEDPEFQASNIMHS
INGYVFDSLQLSVCLHEVAYWYILSIGAQTDFLSVFFSGYTFKHKMVYED
TLTLFPFSGETVFMSMENPGLWILGCHNSDFRNRGMTALLKVSSCDKNTG
DYYEDSYEDISAYLLSKNNAIEPRSFSQNSRHPSTRQKQFNATTIPENDI
EKTDPWFAHRTPMPKIQNVSSSDLLMLLRQSPTPHGLSLSDLQEAKYETF
SDDPSPGAIDSNNSLSEMTHFRPQLHHSGDMVFTPESGLQLRLNEKLGTT
AATELKKLDFKVSSTSNNLISTIPSDNLAAGTDNTSSLGPPSMPVHYDSQ
LDTTLFGKKSSPLTESGGPLSLSEENNDSKLLESGLMNSQESSWGKNVSS
TESGRLFKGKRAHGPALLTKDNALFKVSISLLKTNKTSNNSATNRKTHID
GPSLLIENSPSVWQNILESDTEFKKVTPLIHDRMLMDKNATALRLNHMSN
KTTSSKNMEMVQQKKEGPIPPDAQNPDMSFFKMLFLPESARWIQRTHGKN
SLNSGQGPSPKQLVSLGPEKSVEGQNFLSEKNKVVVGKGEFTKDVGLKEM
VFPSSRNLFLTNLDNLHENNTHNQEKKIQEEIEKKETLIQENVVLPQIHT
VTGTKNFMKNLFLLSTRQNVEGSYDGAYAPVLQDFRSLNDSTNRTKKHTA
HFSKKGEEENLEGLGNQTKQIVEKYACTTRISPNTSQQNFVTQRSKRALK
QFRLPLEETELEKRIIVDDTSTQWSKNMKHLTPSTLTQIDYNEKEKGAIT
QSPLSDCLTRSESIPQANRSPLPIAKVSSFPSIRPIYLTRVLFQDNSSNL
PAASYRKKDSGVQESSHFLQGAKKNNLSLAILTLEMTGDQREVGSLGTSA
TNSVTYKKVENTVLPKPDLPKTSGKVELLPKVHIYQKDLFPTETSNGSPG
HLDLVEGSLLQGTEGAIKWNEANRPGKVPFLRVATESSAKTPSKLLDPLA
WDNHYGTQIPKEEWKSQEKSPEKTAFKKKDTILSLNACESNHAIAAINEG
QNKPEIEVTWAKQGRTERLCSQNPPVLKRHQREITRTTLQSDQEEIDYDD
TISVEMKKEDFDIYDEDENQSPRSFQKKTRHYFIAAVERLWDYGMSSSPH
VLRNRAQSGSVPQFKKVVFQEFTDGSFTQPLYRGELNEHLGLLGPYIRAE
VEDNIMVTFRNQASRPYSFYSSLISYEEDQRQGAEPRKNFVKPNETKTYF
WKVQHHMAPTKDEFDCKAWAYFSDVDLEKDVHSGLIGPLLVCHTNTLNPA
HGRQVTVQEFALFFTIFDETKSWYFTENMERNCRAPSNIQMEDPTFKENY
RFHAINGYIMDTLFGLVMAQDQRIRWYLLSMGSNENIHSIHFSGHVFTVR
KKEEYKMALYNLYPGVFETVEMLPSKAGIWRVECLIGEHLHAGMSTLFLV
YSNKCQTPLGMASGHIRDFQITASGQYGQWAPKLARLHYSGSINAWSTKE
PFSWIKVDLLAPMIIHGIKTQGARQKFSSLYISQFIIMYSLDGKKWQTYR
GNSTGTLMVFFGNVDSSGIKHNIFNPPIIARYIRLHPTHYSIRSTLRMEL
MGCDLNSCSMPLGMESKAISDAQITASSYFTNMFATWSPSKARLHLQGRS
NAWRPQVNNPKEWLQVDFQKTMKVTGVTTQGVKSLLTSMYVKEFLISSSQ
DGHQWTLFFQNGKVKVFQGNQDSFTPVVNSLDPPLLTRYLRIHPQSWVHQ
IALRMEVLGCEAQDLY

Example 9. Generation of a FVIII-Multi-Tregitope Construct

Multiple Tregitopes can be present in highly immunogenic proteins to promote adaptive tolerance. In one exemplary method of producing such constructs, chimeric constructs comprised of the coding sequence of clotting Factor VIII and multiple Tregitope(s) are produced (Sambrook et al., *Molecular Cloning*: A Laboratory Manual, 2

TABLE 9

Factor VIII-Multi-Tregitope: SEQ ID NO: 73
(Tregitope bold)

MQIELSTCFFLCLLRFCFSATRRYYLGAVELSWDYMQSDLGELPVDARFP
PRVPKSFPFNTSVVYKKTLFVEFTDHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKM
HTVNGTVNRSLPGLIGCHRKSVYWHVIGMGTTPEVHSIFLEGHTFLVRNH
RQASLEISPITFLTAQTLLMDLGQFLLFCHISSHQHDGMEAYVKCDSCPE
EPQLRMKNNEEAEDYDDDLTDSEMDVVRFDDDNSPSFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCL
HEVAYWYILSIGAQTDFLSVFFSGYTFKHKMVYEDTLTLFPPSGETVFMS
MENPGLWILGCHNSDFRNRGMTALLKVSSCDKNTGDYYEDSYEDISAYLL
SKNNAIEPRSFSQNSRHPSTRQKQFNATTIPENDIEKTDPWFAHRTPMPK
IQNVSSSDDLMLLRQSPTPHGLSLSDLQEAKYETFSDDPSPGAIDSNNSL
SEMTHFRPQLHHSGDMVFTPESGLQLRLNEKLGTTAATELKKLDFKVSST
SNNLISTIPSDNLAAGTDNTSSLGPPSMPVHYDSQLDTTLFGKKSSPLTE
SGGPLSLSEENNDSKLLESGLMNSQESSWGKNVSSTESGRLFKGKRAHGP
ALLTKDNALFKVSISLLKTNKTSNNSATNRKTHIDGPSLLIENSPSVWQN
ILESDTEFKKVTPLIHDRMLMDKNATALRLNHMSNKTTSSKNMEMVQQKK
EGPIPPDAQNPDMSFFKMLFLPESARWIQRTHGKNSLNSGQGPSPKQLVS
LGPEKSVEGQNFLSEKNKVVVGKGEFTKDVGLKEMVFPSSRNLFLTNLDN
LHENNTHNQEKKIQEEIEKKETLIQENVVLPQIHTVTGTKNFMKNLFLLS
TRQNVEGSYDGAYAPVLQDFRSLNDSTNRTKKHTAHFSKKGEEENLEGLG
NQTKQIVEKYACTTRISPNTSQQNFVTQRSKRALKQFRLPLEETELEKRI
IVDDTSTQWSKNMKHLTPSTLTQIDYNEKEKGAITQSPLSDCLTRSESIP
QANRSPLPIAKVSSFPSIRPIYLTRVLFQDNSSNLPAASYRKKDSGVQES
SHFLQGAKKNNLSLAILTLEMTGDQREVGSLGTSATNSVTYKKVENTVLP
KPDLPKTSGKVELLPKVHIYQKDLFPTETSNGSPGHLDLVEGSLLQGTEG

TABLE 9-continued

Factor VIII-Multi-Tregitope: SEQ ID NO: 73
(Tregitope bold)

AIKWNEANRPGKVPFLRVATESSAKTPSKLLDPLAWDNHYGTQIPKEEWK
SQEKSPEKTAFKKKDTILSLNACESNHAIAAINEGQNKPEIEVTWAKQGR
TERLCSQNPPVLKRHQREITRTTLQSDQEEIDYDDTISVEMKKEDFDIYD
EDENQSPRSFQKKTRHYFIAAVERLWDYGMSSSPHVLRNRAQSGSVPQFK
KVVFQEFTDGSFTQPLYRGELNEHLGLLGPYIRAEVEDNIMVTFRNQASR
PYSFYSSLISYEEDQRQGAEPRKNFVKPNETKTYFWKVQHHMAPTKDEFD
CKAWAYFSDVDLEKDVHSGLIGPLLVCHTNTLNPAHGRQVTVQEFALFFT
IFDETKSWYFTENMERNCRAPSNIQMEDPTFKENYRFHAINGYIMDTLFG
LVMAQDQRIRWYLLSMGSNENIHSIHFSGHVFTVRKKEEYKMALYNLYPG
VFETVEMLPSKAGIWRVECLIGEHLHAGMSTLFLVYSNKCQTPLGMASGH
IRDFQITASGQYGQWAPKLARLHYSGSINAWSTKEPFSWIKVDLLAPMII
HGIKTQGARQKFSSLYISQFIIMYSLDGKKWQTYRGNSTGTLMVFFGNVD
SSGIKHNIFNPPIIARYIRLHPTHYSIRSTLRMELMGCDLNSCSMPLGME
SKAISDAQITASSYFTNMFATWSPSKARLHLQGRSNAWRPQVNNPKEWLQ
VDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDL
YILTIHFTGHSFIYGKIHSIHFSGHVFTVRK

EQUIVALENTS

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

---

The invention claimed is:

1. A method of inducing regulatory T-cells to suppress immune response in a subject comprising administrating to the subject a therapeutically effective amount of a T-cell epitope composition, wherein the T-cell epitope composition comprises one or more isolated T-cell epitope polypeptides, wherein at least one isolated T-cell epitope polypeptide consists of the amino acid sequence of SEQ ID NO: 1.

2. The method of claim 1, wherein the T-cell epitope composition further comprises at least one isolated T-cell epitope polypeptide consisting of an amino acid sequence selected from the group consisting of SEQ ID NOS: 2-14.

3. The method of claim 1, wherein the T-cell epitope composition further comprises an effective amount of one or more antigens and/or allergens.

4. The method of claim 1, wherein the immune suppressive effect is mediated by natural regulatory T cells.

5. The method of claim 1, wherein the immune suppressive effect is mediated by adaptive regulatory T-cells.

6. The method of claim 1, wherein the T-cell epitope composition suppresses an effector T-cell response.

7. The method of claim 6, wherein the T-cell epitope composition suppresses a cytokine secretion of effector T-cells.

8. The method of claim 1, wherein the T-cell epitope composition suppresses a helper T-cell response.

9. The method of claim 1, wherein the T-cell epitope composition suppresses a B-cell response.

* * * * *

SEQUENCE LISTING

```
<160> NUMBER OF SEQ ID NOS: 73

<210> SEQ ID NO 1
<211> LENGTH: 15
<212> TYPE: PRT
<213> ORGANISM: Homo sapiens

<400> SEQUENCE: 1

Ile Leu Thr Ile His Phe Thr Gly His Ser Phe Ile Tyr Gly Lys
1               5                   10                  15

<210> SEQ ID NO 2
<211> LENGTH: 15
<212> TYPE: PRT
<213> ORGANISM: Homo sapiens

<400> SEQUENCE: 2

Ile His Ser Ile His Phe Ser Gly His Val Phe Thr Val Arg Lys
1               5                   10                  15

<210> SEQ ID NO 3
<211> LENGTH: 15
<212> TYPE: PRT
<213> ORGANISM: Homo sapiens

<400> SEQUENCE: 3

Lys Ile Val Phe Lys Asn Met Ala Ser Arg Pro Tyr Ser Ile Tyr
1               5                   10                  15

<210> SEQ ID NO 4
<211> LENGTH: 15
<212> TYPE: PRT
<213> ORGANISM: Homo sapiens
```

-continued

<400> SEQUENCE: 4

Phe Ala Val Phe Asp Glu Asn Lys Ser Trp Tyr Leu Glu Asp Asn
1               5                   10                  15

<210> SEQ ID NO 5
<211> LENGTH: 15
<212> TYPE: PRT
<213> ORGANISM: Homo sapiens

<400> SEQUENCE: 5

Glu Ser Asn Ile Met Ser Thr Ile Asn Gly Tyr Val Pro Glu Ser
1               5                   10                  15

<210> SEQ ID NO 6
<211> LENGTH: 14
<212> TYPE: PRT
<213> ORGANISM: Homo sapiens

<400> SEQUENCE: 6

Glu Lys Asp Ile His Ser Gly Leu Ile Gly Pro Leu Leu Ile
1               5                   10

<210> SEQ ID NO 7
<211> LENGTH: 15
<212> TYPE: PRT
<213> ORGANISM: Homo sapiens

<400> SEQUENCE: 7

Ser His Glu Phe His Ala Ile Asn Gly Met Ile Tyr Ser Leu Pro
1               5                   10                  15

<210> SEQ ID NO 8
<211> LENGTH: 9
<212> TYPE: PRT
<213> ORGANISM: Homo sapiens

<400> SEQUENCE: 8

Ile His Phe Thr Gly His Ser Phe Ile
1               5

<210> SEQ ID NO 9
<211> LENGTH: 9
<212> TYPE: PRT
<213> ORGANISM: Homo sapiens

<400> SEQUENCE: 9

Ile His Phe Ser Gly His Val Phe Thr
1               5

<210> SEQ ID NO 10
<211> LENGTH: 9
<212> TYPE: PRT
<213> ORGANISM: Homo sapiens

<400> SEQUENCE: 10

Phe Lys Asn Met Ala Ser Arg Pro Tyr
1               5

<210> SEQ ID NO 11
<211> LENGTH: 9
<212> TYPE: PRT
<213> ORGANISM: Homo sapiens

```
<400> SEQUENCE: 11

Phe Asp Glu Asn Leu Ser Trp Tyr Leu
1               5

<210> SEQ ID NO 12
<211> LENGTH: 9
<212> TYPE: PRT
<213> ORGANISM: Homo sapiens

<400> SEQUENCE: 12

Ile Met Ser Thr Ile Asn Gly Tyr Val
1               5

<210> SEQ ID NO 13
<211> LENGTH: 9
<212> TYPE: PRT
<213> ORGANISM: Homo sapiens

<400> SEQUENCE: 13

Ile His Ser Gly Leu Ile Gly Pro Leu
1               5

<210> SEQ ID NO 14
<211> LENGTH: 9
<212> TYPE: PRT
<213> ORGANISM: Homo sapiens

<400> SEQUENCE: 14

Phe His Ala Ile Asn Gly Met Ile Tyr
1               5

<210> SEQ ID NO 15
<211> LENGTH: 26
<212> TYPE: PRT
<213> ORGANISM: Homo sapiens

<400> SEQUENCE: 15

Pro Ala Val Leu Gln Ser Ser Gly Leu Tyr Ser Leu Ser Ser Val Val
1               5                   10                  15

Thr Val Pro Ser Ser Ser Leu Gly Thr Gln
            20                  25

<210> SEQ ID NO 16
<211> LENGTH: 9
<212> TYPE: PRT
<213> ORGANISM: Homo sapiens

<400> SEQUENCE: 16

Ile Glu Asp Phe Asn Ser Gly Leu Ile
1               5

<210> SEQ ID NO 17
<211> LENGTH: 15
<212> TYPE: PRT
<213> ORGANISM: Homo sapiens

<400> SEQUENCE: 17

Glu Asn Leu Ile Glu Asp Phe Asn Ser Gly Leu Ile Gly Pro Leu
1               5                   10                  15

<210> SEQ ID NO 18
<211> LENGTH: 9
<212> TYPE: PRT
<213> ORGANISM: Homo sapiens
```

```
<400> SEQUENCE: 18

Val Lys Asp Leu Asn Ser Gly Leu Ile
1               5

<210> SEQ ID NO 19
<211> LENGTH: 15
<212> TYPE: PRT
<213> ORGANISM: Homo sapiens

<400> SEQUENCE: 19

Val Asp Leu Val Lys Asp Leu Asn Ser Gly Leu Ile Gly Ala Leu
1               5                   10                  15

<210> SEQ ID NO 20
<211> LENGTH: 9
<212> TYPE: PRT
<213> ORGANISM: Homo sapiens

<400> SEQUENCE: 20

Lys Ile Val Phe Lys Asn Met Ala Ser
1               5

<210> SEQ ID NO 21
<211> LENGTH: 15
<212> TYPE: PRT
<213> ORGANISM: Homo sapiens

<400> SEQUENCE: 21

Asp Thr Leu Lys Ile Val Phe Lys Asn Met Ala Ser Arg Pro Tyr
1               5                   10                  15

<210> SEQ ID NO 22
<211> LENGTH: 9
<212> TYPE: PRT
<213> ORGANISM: Homo sapiens

<400> SEQUENCE: 22

Val Ile Thr Leu Lys Asn Met Ala Ser
1               5

<210> SEQ ID NO 23
<211> LENGTH: 15
<212> TYPE: PRT
<213> ORGANISM: Homo sapiens

<400> SEQUENCE: 23

Asp Thr Val Val Ile Thr Leu Lys Asn Met Ala Ser His Pro Val
1               5                   10                  15

<210> SEQ ID NO 24
<211> LENGTH: 9
<212> TYPE: PRT
<213> ORGANISM: Homo sapiens

<400> SEQUENCE: 24

Phe Lys Asn Gln Ala Ser Arg Pro Tyr
1               5

<210> SEQ ID NO 25
<211> LENGTH: 15
<212> TYPE: PRT
<213> ORGANISM: Homo sapiens
```

<400> SEQUENCE: 25

Leu Thr Ile Phe Lys Asn Gln Ala Ser Arg Pro Tyr Asn Ile Tyr
1               5                   10                  15

<210> SEQ ID NO 26
<211> LENGTH: 9
<212> TYPE: PRT
<213> ORGANISM: Homo sapiens

<400> SEQUENCE: 26

Leu Lys Asn Met Ala Ser His Pro Val
1               5

<210> SEQ ID NO 27
<211> LENGTH: 15
<212> TYPE: PRT
<213> ORGANISM: Homo sapiens

<400> SEQUENCE: 27

Val Ile Thr Leu Lys Asn Met Ala Ser His Pro Val Ser Leu His
1               5                   10                  15

<210> SEQ ID NO 28
<211> LENGTH: 9
<212> TYPE: PRT
<213> ORGANISM: Homo sapiens

<400> SEQUENCE: 28

Phe Arg Asn Gln Ala Ser Arg Pro Tyr
1               5

<210> SEQ ID NO 29
<211> LENGTH: 15
<212> TYPE: PRT
<213> ORGANISM: Homo sapiens

<400> SEQUENCE: 29

Met Val Thr Phe Arg Asn Gln Ala Ser Arg Pro Tyr Ser Phe Tyr
1               5                   10                  15

<210> SEQ ID NO 30
<211> LENGTH: 9
<212> TYPE: PRT
<213> ORGANISM: Homo sapiens

<400> SEQUENCE: 30

Ile Met His Ser Ile Asn Gly Tyr Val
1               5

<210> SEQ ID NO 31
<211> LENGTH: 15
<212> TYPE: PRT
<213> ORGANISM: Homo sapiens

<400> SEQUENCE: 31

Ala Ser Asn Ile Met Ser Ser Ile Asn Gly Tyr Val Phe Asp Ser
1               5                   10                  15

<210> SEQ ID NO 32
<211> LENGTH: 9
<212> TYPE: PRT
<213> ORGANISM: Homo sapiens

```
<400> SEQUENCE: 32

Leu Leu Leu Lys Gln Ser Asn Ser Ser
1               5

<210> SEQ ID NO 33
<211> LENGTH: 15
<212> TYPE: PRT
<213> ORGANISM: Homo sapiens

<400> SEQUENCE: 33

Ser Asp Leu Leu Leu Lys Gln Ser Asn Ser Ser Lys Ile Leu
1               5                   10                  15

<210> SEQ ID NO 34
<211> LENGTH: 9
<212> TYPE: PRT
<213> ORGANISM: Homo sapiens

<400> SEQUENCE: 34

Arg Val Leu Phe Gln Asp Asn Ser Ser
1               5

<210> SEQ ID NO 35
<211> LENGTH: 15
<212> TYPE: PRT
<213> ORGANISM: Homo sapiens

<400> SEQUENCE: 35

Tyr Leu Thr Arg Val Leu Phe Gln Asp Asn Ser Ser His Leu Pro
1               5                   10                  15

<210> SEQ ID NO 36
<211> LENGTH: 9
<212> TYPE: PRT
<213> ORGANISM: Homo sapiens

<400> SEQUENCE: 36

Phe Lys Asn Leu Ala Ser Arg Pro Tyr
1               5

<210> SEQ ID NO 37
<211> LENGTH: 15
<212> TYPE: PRT
<213> ORGANISM: Homo sapiens

<400> SEQUENCE: 37

Gln Val Arg Phe Lys Asn Leu Ala Ser Arg Pro Tyr Ser Leu His
1               5                   10                  15

<210> SEQ ID NO 38
<211> LENGTH: 9
<212> TYPE: PRT
<213> ORGANISM: Homo sapiens

<400> SEQUENCE: 38

Leu Lys Asn Met Ala Ser His Pro Val
1               5

<210> SEQ ID NO 39
<211> LENGTH: 15
<212> TYPE: PRT
<213> ORGANISM: Homo sapiens
```

```
<400> SEQUENCE: 39

Val Ile Thr Leu Lys Asn Met Ala Ser His Pro Val Ser Leu His
1               5                   10                  15

<210> SEQ ID NO 40
<211> LENGTH: 9
<212> TYPE: PRT
<213> ORGANISM: Homo sapiens

<400> SEQUENCE: 40

Phe Lys Asn Gln Ala Ser Arg Pro Tyr
1               5

<210> SEQ ID NO 41
<211> LENGTH: 15
<212> TYPE: PRT
<213> ORGANISM: Homo sapiens

<400> SEQUENCE: 41

Leu Ile Ile Phe Lys Asn Gln Ala Ser Arg Pro Tyr Asn Ile Tyr
1               5                   10                  15

<210> SEQ ID NO 42
<211> LENGTH: 9
<212> TYPE: PRT
<213> ORGANISM: Homo sapiens

<400> SEQUENCE: 42

Phe Arg Asn Gln Ala Ser Arg Pro Tyr
1               5

<210> SEQ ID NO 43
<211> LENGTH: 15
<212> TYPE: PRT
<213> ORGANISM: Homo sapiens

<400> SEQUENCE: 43

Met Val Thr Phe Arg Asn Gln Ala Ser Arg Pro Tyr Ser Phe Tyr
1               5                   10                  15

<210> SEQ ID NO 44
<211> LENGTH: 9
<212> TYPE: PRT
<213> ORGANISM: Homo sapiens

<400> SEQUENCE: 44

Phe His Ala Ile Asn Gly Tyr Ile Met
1               5

<210> SEQ ID NO 45
<211> LENGTH: 15
<212> TYPE: PRT
<213> ORGANISM: Homo sapiens

<400> SEQUENCE: 45

Asn Tyr Arg Phe His Ala Ile Asn Gly Tyr Ile Met Asp Thr Leu
1               5                   10                  15

<210> SEQ ID NO 46
<211> LENGTH: 9
<212> TYPE: PRT
<213> ORGANISM: Homo sapiens
```

```
<400> SEQUENCE: 46

Ile Lys Lys Ile Thr Ala Ile Ile Thr
1               5

<210> SEQ ID NO 47
<211> LENGTH: 15
<212> TYPE: PRT
<213> ORGANISM: Homo sapiens

<400> SEQUENCE: 47

Leu Leu Lys Ile Lys Lys Ile Thr Ala Ile Ile Thr Gln Gly Cys
1               5                   10                  15

<210> SEQ ID NO 48
<211> LENGTH: 9
<212> TYPE: PRT
<213> ORGANISM: Homo sapiens

<400> SEQUENCE: 48

Phe Lys Lys Val Thr Pro Leu Ile His
1               5

<210> SEQ ID NO 49
<211> LENGTH: 15
<212> TYPE: PRT
<213> ORGANISM: Homo sapiens

<400> SEQUENCE: 49

Asp Thr Glu Phe Lys Lys Val Thr Pro Leu Ile His Asp Arg Met
1               5                   10                  15

<210> SEQ ID NO 50
<211> LENGTH: 9
<212> TYPE: PRT
<213> ORGANISM: Homo sapiens

<400> SEQUENCE: 50

Val Lys Asn Phe Phe Asn Pro Pro Ile
1               5

<210> SEQ ID NO 51
<211> LENGTH: 15
<212> TYPE: PRT
<213> ORGANISM: Homo sapiens

<400> SEQUENCE: 51

Lys Gly His Val Lys Asn Phe Phe Asn Pro Pro Ile Ile Ser Arg
1               5                   10                  15

<210> SEQ ID NO 52
<211> LENGTH: 9
<212> TYPE: PRT
<213> ORGANISM: Homo sapiens

<400> SEQUENCE: 52

Lys His Asn Ile Phe Asn Pro Pro Ile
1               5

<210> SEQ ID NO 53
<211> LENGTH: 15
<212> TYPE: PRT
<213> ORGANISM: Homo sapiens
```

```
<400> SEQUENCE: 53

Ser Gly Ile Lys His Asn Ile Phe Asn Pro Pro Ile Ile Ala Arg
1               5                   10                  15

<210> SEQ ID NO 54
<211> LENGTH: 9
<212> TYPE: PRT
<213> ORGANISM: Homo sapiens

<400> SEQUENCE: 54

Phe Asp Glu Thr Lys Ser Trp Tyr Phe
1               5

<210> SEQ ID NO 55
<211> LENGTH: 15
<212> TYPE: PRT
<213> ORGANISM: Homo sapiens

<400> SEQUENCE: 55

Phe Thr Ile Phe Asp Glu Thr Lys Ser Trp Tyr Phe Thr Glu Asn
1               5                   10                  15

<210> SEQ ID NO 56
<211> LENGTH: 9
<212> TYPE: PRT
<213> ORGANISM: Homo sapiens

<400> SEQUENCE: 56

Phe Asp Glu Asn Arg Ser Trp Tyr Leu
1               5

<210> SEQ ID NO 57
<211> LENGTH: 15
<212> TYPE: PRT
<213> ORGANISM: Homo sapiens

<400> SEQUENCE: 57

Phe Ser Val Phe Asp Glu Asn Arg Ser Trp Tyr Leu Thr Glu Asn
1               5                   10                  15

<210> SEQ ID NO 58
<211> LENGTH: 9
<212> TYPE: PRT
<213> ORGANISM: Homo sapiens

<400> SEQUENCE: 58

Val His Ser Gly Leu Ile Gly Pro Leu
1               5

<210> SEQ ID NO 59
<211> LENGTH: 14
<212> TYPE: PRT
<213> ORGANISM: Homo sapiens

<400> SEQUENCE: 59

Glu Lys Asp Val His Ser Gly Leu Ile Gly Pro Leu Ile Val
1               5                   10

<210> SEQ ID NO 60
<211> LENGTH: 9
<212> TYPE: PRT
<213> ORGANISM:

```
<400> SEQUENCE: 60

Pro Arg Tyr Val Lys Gln Asn Thr Leu
1               5

<210> SEQ ID NO 61
<211> LENGTH: 9
<212> TYPE: PRT
<213> ORGANISM: Human Influenza A virus

<400> SEQUENCE: 61

Arg Tyr Val Lys Gln Asn Thr Leu Lys
1               5

<210> SEQ ID NO 62
<211> LENGTH: 9
<212> TYPE: PRT
<213> ORGANISM: Human Influenza A virus

<400> SEQUENCE: 62

Tyr Val Lys Gln Asn Thr Leu Lys Leu
1               5

<210> SEQ ID NO 63
<211> LENGTH: 9
<212> TYPE: PRT
<213> ORGANISM: Human Influenza A virus

<400> SEQUENCE: 63

Val Lys Gln Asn Thr Leu Lys Leu Ala
1               5

<210> SEQ ID NO 64
<211> LENGTH: 9
<212> TYPE: PRT
<213> ORGANISM: Human Influenza A virus

<400> SEQUENCE: 64

Lys Gln Asn Thr Leu Lys Leu Ala Thr
1               5

<210> SEQ ID NO 65
<211> LENGTH: 32
<212> TYPE: DNA
<213> ORGANISM: Artificial Sequence
<220> FEATURE:
<223> OTHER INFORMATION: Sythetic primer

<400> SEQUENCE: 65
gttaactagt tcagctggac cacagccgca gc                                    32

<210> SEQ ID NO 66
<211> LENGTH: 40
<212> TYPE: DNA
<213> ORGANISM: Artificial Sequence
<220> FEATURE:
<223> OTHER INFORMATION: Synthetic primer

<400> SEQUENCE: 66
cgggttaact agttcagaaa tcctttctct tgaccatggc                            40

<210> SEQ ID NO 67
<211> LENGTH: 25
<212> TYPE: DNA
<213> ORGANISM: Artificial Sequence
```

```
<220> FEATURE:
<223> OTHER INFORMATION: Synthetic primer

<400> SEQUENCE: 67
ctagcctctg gaatcctttc tcttg                                              25

<210> SEQ ID NO 68
<211> LENGTH: 21
<212> TYPE: PRT
<213> ORGANISM: Homo sapiens

<400> SEQUENCE: 68
```

Arg Ile His Met Val Tyr Ser Lys Arg Ser Gly Lys Pro Arg Gly Tyr
1               5                   10                  15

Ala Phe Ile Glu Tyr
            20

```
<210> SEQ ID NO 69
<211> LENGTH: 2366
<212> TYPE: PRT
<213> ORGANISM: Artificial Sequence
<220> FEATURE:
<223> OTHER INFORMATION: Synthetic construct

<400> SEQUENCE: 69
```

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Thr
                245                 250                 255

-continued

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Cys Asp Ser Cys Pro Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

```
Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
            850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080
```

-continued

```
Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser Glu Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser Asn Leu Pro Ala Ala Ser Tyr Arg Lys Lys
1430                1435                1440

Asp Ser Gly Val Gln Glu Ser His Phe Leu Gln Gly Ala Lys
1445                1450                1455

Lys Asn Asn Leu Ser Leu Ala Ile Leu Thr Leu Glu Met Thr Gly
1460                1465                1470
```

```
Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860
```

```
Lys Asp Val His Ser Gly Leu Ile Gly Pro Leu Leu Val Cys His
    1865            1870            1875

Thr Asn Thr Leu Asn Pro Ala His Gly Arg Gln Val Thr Val Gln
    1880            1885            1890

Glu Phe Ala Leu Phe Phe Thr Ile Phe Asp Glu Thr Lys Ser Trp
    1895            1900            1905

Tyr Phe Thr Glu Asn Met Glu Arg Asn Cys Arg Ala Pro Ser Asn
    1910            1915            1920

Ile Gln Met Glu Asp Pro Thr Phe Lys Glu Asn Tyr Arg Phe His
    1925            1930            1935

Ala Ile Asn Gly Tyr Ile Met Asp Thr Leu Phe Gly Leu Val Met
    1940            1945            1950

Ala Gln Asp Gln Arg Ile Arg Trp Tyr Leu Leu Ser Met Gly Ser
    1955            1960            1965

Asn Glu Asn Ile His Ser Ile His Phe Ser Gly His Val Phe Thr
    1970            1975            1980

Val Arg Lys Lys Glu Glu Tyr Lys Met Ala Leu Tyr Asn Leu Tyr
    1985            1990            1995

Pro Gly Val Phe Glu Thr Val Glu Met Leu Pro Ser Lys Ala Gly
    2000            2005            2010

Ile Trp Arg Val Glu Cys Leu Ile Gly Glu His Leu His Ala Gly
    2015            2020            2025

Met Ser Thr Leu Phe Leu Val Tyr Ser Asn Lys Cys Gln Thr Pro
    2030            2035            2040

Leu Gly Met Ala Ser Gly His Ile Arg Asp Phe Gln Ile Thr Ala
    2045            2050            2055

Ser Gly Gln Tyr Gly Gln Trp Ala Pro Lys Leu Ala Arg Leu His
    2060            2065            2070

Tyr Ser Gly Ser Ile Asn Ala Trp Ser Thr Lys Glu Pro Phe Ser
    2075            2080            2085

Trp Ile Lys Val Asp Leu Leu Ala Pro Met Ile Ile His Gly Ile
    2090            2095            2100

Lys Thr Gln Gly Ala Arg Gln Lys Phe Ser Ser Leu Tyr Ile Ser
    2105            2110            2115

Gln Phe Ile Ile Met Tyr Ser Leu Asp Gly Lys Lys Trp Gln Thr
    2120            2125            2130

Tyr Arg Gly Asn Ser Thr Gly Thr Leu Met Val Phe Phe Gly Asn
    2135            2140            2145

Val Asp Ser Ser Gly Ile Lys His Asn Ile Phe Asn Pro Pro Ile
    2150            2155            2160

Ile Ala Arg Tyr Ile Arg Leu His Pro Thr His Tyr Ser Ile Arg
    2165            2170            2175

Ser Thr Leu Arg Met Glu Leu Met Gly Cys Asp Leu Asn Ser Cys
    2180            2185            2190

Ser Met Pro Leu Gly Met Glu Ser Lys Ala Ile Ser Asp Ala Gln
    2195            2200            2205

Ile Thr Ala Ser Ser Tyr Phe Thr Asn Met Phe Ala Thr Trp Ser
    2210            2215            2220

Pro Ser Lys Ala Arg Leu His Leu Gln Gly Arg Ser Asn Ala Trp
    2225            2230            2235

Arg Pro Gln Val Asn Asn Pro Lys Glu Trp Leu Gln Val Asp Phe
    2240            2245            2250
```

```
Gln Lys Thr Met Lys Val Thr Gly Val Thr Gln Gly Val Lys
    2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr Ile Leu Thr Ile His Phe Thr
    2345                2350                2355

Gly His Ser Phe Ile Tyr Gly Lys
    2360                2365

<210> SEQ ID NO 70
<211> LENGTH: 2366
<212> TYPE: PRT
<213> ORGANISM: Artificial Sequence
<220> FEATURE:
<223> OTHER INFORMATION: Sythetic construct

<400> SEQUENCE: 70

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240
```

```
Ala Ala Ser Ala Arg Ala Trp Pro Lys Met His Thr Val Asn Gly Thr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Cys Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655
```

-continued

```
Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065
```

-continued

Met Leu Met Asp Lys Asn Ala Thr Ala Leu Arg Leu Asn His Met
1070                    1075                1080

Ser Asn Lys Thr Thr Ser Ser Lys Asn Met Glu Met Val Gln Gln
1085                    1090                1095

Lys Lys Glu Gly Pro Ile Pro Pro Asp Ala Gln Asn Pro Asp Met
1100                    1105                1110

Ser Phe Phe Lys Met Leu Phe Leu Pro Glu Ser Ala Arg Trp Ile
1115                    1120                1125

Gln Arg Thr His Gly Lys Asn Ser Leu Asn Ser Gly Gln Gly Pro
1130                    1135                1140

Ser Pro Lys Gln Leu Val Ser Leu Gly Pro Glu Lys Ser Val Glu
1145                    1150                1155

Gly Gln Asn Phe Leu Ser Glu Lys Asn Lys Val Val Val Gly Lys
1160                    1165                1170

Gly Glu Phe Thr Lys Asp Val Gly Leu Lys Glu Met Val Phe Pro
1175                    1180                1185

Ser Ser Arg Asn Leu Phe Leu Thr Asn Leu Asp Asn Leu His Glu
1190                    1195                1200

Asn Asn Thr His Asn Gln Glu Lys Lys Ile Gln Glu Glu Ile Glu
1205                    1210                1215

Lys Lys Glu Thr Leu Ile Gln Glu Asn Val Val Leu Pro Gln Ile
1220                    1225                1230

His Thr Val Thr Gly Thr Lys Asn Phe Met Lys Asn Leu Phe Leu
1235                    1240                1245

Leu Ser Thr Arg Gln Asn Val Glu Gly Ser Tyr Asp Gly Ala Tyr
1250                    1255                1260

Ala Pro Val Leu Gln Asp Phe Arg Ser Leu Asn Asp Ser Thr Asn
1265                    1270                1275

Arg Thr Lys Lys His Thr Ala His Phe Ser Lys Lys Gly Glu Glu
1280                    1285                1290

Glu Asn Leu Glu Gly Leu Gly Asn Gln Thr Lys Gln Ile Val Glu
1295                    1300                1305

Lys Tyr Ala Cys Thr Thr Arg Ile Ser Pro Asn Thr Ser Gln Gln
1310                    1315                1320

Asn Phe Val Thr Gln Arg Ser Lys Arg Ala Leu Lys Gln Phe Arg
1325                    1330                1335

Leu Pro Leu Glu Glu Thr Glu Leu Glu Lys Arg Ile Ile Val Asp
1340                    1345                1350

Asp Thr Ser Thr Gln Trp Ser Lys Asn Met Lys His Leu Thr Pro
1355                    1360                1365

Ser Thr Leu Thr Gln Ile Asp Tyr Asn Glu Lys Glu Lys Gly Ala
1370                    1375                1380

Ile Thr Gln Ser Pro Leu Ser Asp Cys Leu Thr Arg Ser Glu Ser
1385                    1390                1395

Ile Pro Gln Ala Asn Arg Ser Pro Leu Pro Ile Ala Lys Val Ser
1400                    1405                1410

Ser Phe Pro Ser Ile Arg Pro Ile Tyr Leu Thr Arg Val Leu Phe
1415                    1420                1425

Gln Asp Asn Ser Ser Asn Leu Pro Ala Ala Ser Tyr Arg Lys Lys
1430                    1435                1440

Asp Ser Gly Val Gln Glu Ser Ser His Phe Leu Gln Gly Ala Lys
1445                    1450                1455

```
Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845
```

```
Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Leu Thr Ile His Phe Thr Gly
1895                1900                1905

His Ser Phe Ile Tyr Gly Lys Ile Phe Asp Glu Thr Lys Ser Trp
1910                1915                1920

Tyr Phe Thr Glu Asn Met Glu Arg Asn Cys Arg Ala Pro Ser Asn
1925                1930                1935

Ile Gln Met Glu Asp Pro Thr Phe Lys Glu Asn Tyr Arg Phe His
1940                1945                1950

Ala Ile Asn Gly Tyr Ile Met Asp Thr Leu Phe Gly Leu Val Met
1955                1960                1965

Ala Gln Asp Gln Arg Ile Arg Trp Tyr Leu Leu Ser Met Gly Ser
1970                1975                1980

Asn Glu Asn Ile His Ser Ile His Phe Ser Gly His Val Phe Thr
1985                1990                1995

Val Arg Lys Lys Glu Glu Tyr Lys Met Ala Leu Tyr Asn Leu Tyr
2000                2005                2010

Pro Gly Val Phe Glu Thr Val Glu Met Leu Pro Ser Lys Ala Gly
2015                2020                2025

Ile Trp Arg Val Glu Cys Leu Ile Gly Glu His Leu His Ala Gly
2030                2035                2040

Met Ser Thr Leu Phe Leu Val Tyr Ser Asn Lys Cys Gln Thr Pro
2045                2050                2055

Leu Gly Met Ala Ser Gly His Ile Arg Asp Phe Gln Ile Thr Ala
2060                2065                2070

Ser Gly Gln Tyr Gly Gln Trp Ala Pro Lys Leu Ala Arg Leu His
2075                2080                2085

Tyr Ser Gly Ser Ile Asn Ala Trp Ser Thr Lys Glu Pro Phe Ser
2090                2095                2100

Trp Ile Lys Val Asp Leu Leu Ala Pro Met Ile Ile His Gly Ile
2105                2110                2115

Lys Thr Gln Gly Ala Arg Gln Lys Phe Ser Ser Leu Tyr Ile Ser
2120                2125                2130

Gln Phe Ile Ile Met Tyr Ser Leu Asp Gly Lys Lys Trp Gln Thr
2135                2140                2145

Tyr Arg Gly Asn Ser Thr Gly Thr Leu Met Val Phe Phe Gly Asn
2150                2155                2160

Val Asp Ser Ser Gly Ile Lys His Asn Ile Phe Asn Pro Pro Ile
2165                2170                2175

Ile Ala Arg Tyr Ile Arg Leu His Pro Thr His Tyr Ser Ile Arg
2180                2185                2190

Ser Thr Leu Arg Met Glu Leu Met Gly Cys Asp Leu Asn Ser Cys
2195                2200                2205

Ser Met Pro Leu Gly Met Glu Ser Lys Ala Ile Ser Asp Ala Gln
2210                2215                2220

Ile Thr Ala Ser Ser Tyr Phe Thr Asn Met Phe Ala Thr Trp Ser
2225                2230                2235
```

```
Pro Ser Lys Ala Arg Leu His Leu Gln Gly Arg Ser Asn Ala Trp
    2240                2245                2250

Arg Pro Gln Val Asn Asn Pro Lys Glu Trp Leu Gln Val Asp Phe
    2255                2260                2265

Gln Lys Thr Met Lys Val Thr Gly Val Thr Thr Gln Gly Val Lys
    2270                2275                2280

Ser Leu Leu Thr Ser Met Tyr Val Lys Glu Phe Leu Ile Ser Ser
    2285                2290                2295

Ser Gln Asp Gly His Gln Trp Thr Leu Phe Phe Gln Asn Gly Lys
    2300                2305                2310

Val Lys Val Phe Gln Gly Asn Gln Asp Ser Phe Thr Pro Val Val
    2315                2320                2325

Asn Ser Leu Asp Pro Pro Leu Leu Thr Arg Tyr Leu Arg Ile His
    2330                2335                2340

Pro Gln Ser Trp Val His Gln Ile Ala Leu Arg Met Glu Val Leu
    2345                2350                2355

Gly Cys Glu Ala Gln Asp Leu Tyr
    2360                2365

<210> SEQ ID NO 71
<211> LENGTH: 2366
<212> TYPE: PRT
<213> ORGANISM: Artificial Sequence
<220> FEATURE:
<223> OTHER INFORMATION: Synthetic construct

<400> SEQUENCE: 71

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220
```

-continued

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Thr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Cys Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640
```

```
Phe Asp Ser Leu Gln Leu Ser Val Cys Leu His Glu Val Ala Tyr Trp
            645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
        690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
            725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
            755                 760                 765
Ser Thr Arg Gln Lys Gln Phe Asn Ala Thr Thr Ile Pro Glu Asn Asp
            770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
                820                 825                 830
Glu Thr Phe Ser Asp Asp Pro Ser Pro Gly Ala Ile Asp Ser Asn Asn
                835                 840                 845
Ser Leu Ser Glu Met Thr His Phe Arg Pro Gln Leu His His Ser Gly
                850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
                900                 905                 910
Leu Ala Ala Gly Thr Asp Asn Thr Ser Ser Leu Gly Pro Pro Ser Met
                915                 920                 925
Pro Val His Tyr Asp Ser Gln Leu Asp Thr Thr Leu Phe Gly Lys Lys
                930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Ser Thr Glu Ser Gly Arg Leu Phe
                980                 985                 990
Lys Gly Lys Arg Ala His Gly Pro Ala Leu Leu Thr Lys Asp Asn Ala
                995                1000               1005
Leu Phe Lys Val Ser Ile Ser Leu Leu Lys Thr Asn Lys Thr Ser
                1010               1015               1020
Asn Asn Ser Ala Thr Asn Arg Lys Thr His Ile Asp Gly Pro Ser
                1025               1030               1035
Leu Leu Ile Glu Asn Ser Pro Ser Val Trp Gln Asn Ile Leu Glu
                1040               1045               1050
```

-continued

```
Ser Asp Thr Glu Phe Lys Lys Val Thr Pro Leu Ile His Asp Arg
1055                1060                1065

Met Leu Met Asp Lys Asn Ala Thr Ala Leu Arg Leu Asn His Met
1070                1075                1080

Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser Glu Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser Asn Leu Pro Ala Ala Ser Tyr Arg Lys Lys
1430                1435                1440
```

```
Asp Ser Gly Val Gln Glu Ser Ser His Phe Leu Gln Gly Ala Lys
    1445                1450                1455
Lys Asn Asn Leu Ser Leu Ala Ile Leu Thr Leu Glu Met Thr Gly
    1460                1465                1470
Asp Gln Arg Glu Val Gly Ser Leu Gly Thr Ser Ala Thr Asn Ser
    1475                1480                1485
Val Thr Tyr Lys Lys Val Glu Asn Thr Val Leu Pro Lys Pro Asp
    1490                1495                1500
Leu Pro Lys Thr Ser Gly Lys Val Glu Leu Leu Pro Lys Val His
    1505                1510                1515
Ile Tyr Gln Lys Asp Leu Phe Pro Thr Glu Thr Ser Asn Gly Ser
    1520                1525                1530
Pro Gly His Leu Asp Leu Val Glu Gly Ser Leu Leu Gln Gly Thr
    1535                1540                1545
Glu Gly Ala Ile Lys Trp Asn Glu Ala Asn Arg Pro Gly Lys Val
    1550                1555                1560
Pro Phe Leu Arg Val Ala Thr Glu Ser Ser Ala Lys Thr Pro Ser
    1565                1570                1575
Lys Leu Leu Asp Pro Leu Ala Trp Asp Asn His Tyr Gly Thr Gln
    1580                1585                1590
Ile Pro Lys Glu Glu Trp Lys Ser Gln Glu Lys Ser Pro Glu Lys
    1595                1600                1605
Thr Ala Phe Lys Lys Lys Asp Thr Ile Leu Ser Leu Asn Ala Cys
    1610                1615                1620
Glu Ser Asn His Ala Ile Ala Ala Ile Asn Glu Gly Gln Asn Lys
    1625                1630                1635
Pro Glu Ile Glu Val Thr Trp Ala Lys Gln Gly Arg Thr Glu Arg
    1640                1645                1650
Leu Cys Ser Gln Asn Pro Pro Val Leu Lys Arg His Gln Arg Glu
    1655                1660                1665
Ile Thr Arg Thr Thr Leu Gln Ser Asp Gln Glu Glu Ile Asp Tyr
    1670                1675                1680
Asp Asp Thr Ile Ser Val Glu Met Lys Lys Glu Asp Phe Asp Ile
    1685                1690                1695
Tyr Asp Glu Asp Glu Asn Gln Ser Pro Arg Ser Phe Gln Lys Lys
    1700                1705                1710
Thr Arg His Tyr Phe Ile Ala Ala Val Glu Arg Leu Trp Asp Tyr
    1715                1720                1725
Gly Met Ser Ser Ser Pro His Val Leu Arg Asn Arg Ala Gln Ser
    1730                1735                1740
Gly Ser Val Pro Gln Phe Lys Lys Val Val Phe Gln Glu Phe Thr
    1745                1750                1755
Asp Gly Ser Phe Thr Gln Pro Leu Tyr Arg Gly Glu Leu Asn Glu
    1760                1765                1770
His Leu Gly Leu Leu Gly Pro Tyr Ile Arg Ala Glu Val Glu Asp
    1775                1780                1785
Asn Ile Met Val Thr Phe Arg Asn Gln Ala Ser Arg Pro Tyr Ser
    1790                1795                1800
Phe Tyr Ser Ser Leu Ile Ser Tyr Glu Glu Asp Gln Arg Gln Gly
    1805                1810                1815
Ala Glu Pro Arg Lys Asn Phe Val Lys Pro Asn Glu Thr Lys Thr
    1820                1825                1830
```

-continued

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Ser Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Phe Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160

Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220

```
Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr Ile His Ser Ile His Phe Ser
    2345                2350                2355

Gly His Val Phe Thr Val Arg Lys
    2360                2365

<210> SEQ ID NO 72
<211> LENGTH: 2366
<212> TYPE: PRT
<213> ORGANISM: Artificial Sequence
<220> FEATURE:
<223> OTHER INFORMATION: Synthetic construct

<400> SEQUENCE: 72

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205
```

-continued

```
Gln Thr Leu His Lys Phe Ile Leu Leu Phe Ala Val Phe Asp Glu Gly
210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Thr
        245                 250                 255
Val Asn Arg Ser Leu Pro Gly Leu Ile Gly Cys His Arg Lys Ser Val
        260                 265                 270
Tyr Trp His Val Ile Gly Met Gly Thr Thr Pro Glu Val His Ser Ile
            275                 280                 285
Phe Leu Glu Gly His Thr Phe Leu Val Arg Asn His Arg Gln Ala Ser
290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Cys Asp Ser Cys Pro Glu Glu Pro
                340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asn Ser
370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Val Arg Phe Met
            435                 440                 445
Ala Tyr Thr Asp Glu Thr Phe Lys Thr Arg Glu Ala Ile Gln His Glu
450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
610                 615                 620
```

```
Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035
```

```
Leu Leu Ile Glu Asn Ser Pro Ser Val Trp Gln Asn Ile Leu Glu
1040                1045                1050

Ser Asp Thr Glu Phe Lys Lys Val Thr Pro Leu Ile His Asp Arg
1055                1060                1065

Met Leu Met Asp Lys Asn Ala Thr Ala Leu Arg Leu Asn His Met
1070                1075                1080

Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser Glu Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425
```

```
Gln Asp Asn Ser Ser Asn Leu Pro Ala Ala Ser Tyr Arg Lys Lys
    1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815
```

```
Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile His Ser Ile His Phe Ser Gly
1895                1900                1905

His Val Phe Thr Val Arg Lys Ile Phe Asp Glu Thr Lys Ser Trp
1910                1915                1920

Tyr Phe Thr Glu Asn Met Glu Arg Asn Cys Arg Ala Pro Ser Asn
    1925                1930                1935

Ile Gln Met Glu Asp Pro Thr Phe Lys Glu Asn Tyr Arg Phe His
1940                1945                1950

Ala Ile Asn Gly Tyr Ile Met Asp Thr Leu Phe Gly Leu Val Met
1955                1960                1965

Ala Gln Asp Gln Arg Ile Arg Trp Tyr Leu Leu Ser Met Gly Ser
1970                1975                1980

Asn Glu Asn Ile His Ser Ile His Phe Ser Gly His Val Phe Thr
1985                1990                1995

Val Arg Lys Lys Glu Glu Tyr Lys Met Ala Leu Tyr Asn Leu Tyr
    2000                2005                2010

Pro Gly Val Phe Glu Thr Val Glu Met Leu Pro Ser Lys Ala Gly
    2015                2020                2025

Ile Trp Arg Val Glu Cys Leu Ile Gly Glu His Leu His Ala Gly
    2030                2035                2040

Met Ser Thr Leu Phe Leu Val Tyr Ser Asn Lys Cys Gln Thr Pro
    2045                2050                2055

Leu Gly Met Ala Ser Gly His Ile Arg Asp Phe Gln Ile Thr Ala
    2060                2065                2070

Ser Gly Gln Tyr Gly Gln Trp Ala Pro Lys Leu Ala Arg Leu His
    2075                2080                2085

Tyr Ser Gly Ser Ile Asn Ala Trp Ser Thr Lys Glu Pro Phe Ser
    2090                2095                2100

Trp Ile Lys Val Asp Leu Leu Ala Pro Met Ile Ile His Gly Ile
    2105                2110                2115

Lys Thr Gln Gly Ala Arg Gln Lys Phe Ser Ser Leu Tyr Ile Ser
    2120                2125                2130

Gln Phe Ile Ile Met Tyr Ser Leu Asp Gly Lys Lys Trp Gln Thr
    2135                2140                2145

Tyr Arg Gly Asn Ser Thr Gly Thr Leu Met Val Phe Phe Gly Asn
    2150                2155                2160

Val Asp Ser Ser Gly Ile Lys His Asn Ile Phe Asn Pro Pro Ile
    2165                2170                2175

Ile Ala Arg Tyr Ile Arg Leu His Pro Thr His Tyr Ser Ile Arg
    2180                2185                2190

Ser Thr Leu Arg Met Glu Leu Met Gly Cys Asp Leu Asn Ser Cys
    2195                2200                2205
```

```
Ser Met Pro Leu Gly Met Glu Ser Lys Ala Ile Ser Asp Ala Gln
2210                2215                2220

Ile Thr Ala Ser Ser Tyr Phe Thr Asn Met Phe Ala Thr Trp Ser
2225                2230                2235

Pro Ser Lys Ala Arg Leu His Leu Gln Gly Arg Ser Asn Ala Trp
2240                2245                2250

Arg Pro Gln Val Asn Asn Pro Lys Glu Trp Leu Gln Val Asp Phe
2255                2260                2265

Gln Lys Thr Met Lys Val Thr Gly Val Thr Gln Gly Val Lys
2270                2275                2280

Ser Leu Leu Thr Ser Met Tyr Val Lys Glu Phe Leu Ile Ser Ser
2285                2290                2295

Ser Gln Asp Gly His Gln Trp Thr Leu Phe Phe Gln Asn Gly Lys
2300                2305                2310

Val Lys Val Phe Gln Gly Asn Gln Asp Ser Phe Thr Pro Val Val
2315                2320                2325

Asn Ser Leu Asp Pro Pro Leu Leu Thr Arg Tyr Leu Arg Ile His
2330                2335                2340

Pro Gln Ser Trp Val His Gln Ile Ala Leu Arg Met Glu Val Leu
2345                2350                2355

Gly Cys Glu Ala Gln Asp Leu Tyr
2360                2365

<210> SEQ ID NO 73
<211> LENGTH: 2381
<212> TYPE: PRT
<213> ORGANISM: Artificial Sequence
<220> FEATURE:
<223> OTHER INFORMATION: Synthetic construct

<400> SEQUENCE: 73

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190
```

```
Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Thr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Cys Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605
```

```
Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
      1010                1015                1020
```

```
Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser Glu Ser
    1385                1390                1395

Ile Pro Gln Ala Asn Arg Ser Pro Leu Pro Ile Ala Lys Val Ser
    1400                1405                1410
```

-continued

```
Ser Phe Pro Ser Ile Arg Pro Ile Tyr Leu Thr Arg Val Leu Phe
1415                1420                1425

Gln Asp Asn Ser Ser Asn Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800
```

```
Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Ser Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Phe Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190
```

-continued

```
Ser Met  Pro Leu Gly Met Glu  Ser Lys Ala Ile Ser  Asp Ala Gln
    2195                 2200                 2205

Ile Thr  Ala Ser Ser Tyr Phe  Thr Asn Met Phe Ala  Thr Trp Ser
    2210                 2215                 2220

Pro Ser  Lys Ala Arg Leu His  Leu Gln Gly Arg Ser  Asn Ala Trp
    2225                 2230                 2235

Arg Pro  Gln Val Asn Asn Pro  Lys Glu Trp Leu Gln  Val Asp Phe
    2240                 2245                 2250

Gln Lys  Thr Met Lys Val Thr  Gly Val Thr Thr Gln  Gly Val Lys
    2255                 2260                 2265

Ser Leu  Leu Thr Ser Met Tyr  Val Lys Glu Phe Leu  Ile Ser Ser
    2270                 2275                 2280

Ser Gln  Asp Gly His Gln Trp  Thr Leu Phe Phe Gln  Asn Gly Lys
    2285                 2290                 2295

Val Lys  Val Phe Gln Gly Asn  Gln Asp Ser Phe Thr  Pro Val Val
    2300                 2305                 2310

Asn Ser  Leu Asp Pro Pro Leu  Leu Thr Arg Tyr Leu  Arg Ile His
    2315                 2320                 2325

Pro Gln  Ser Trp Val His Gln  Ile Ala Leu Arg Met  Glu Val Leu
    2330                 2335                 2340

Gly Cys  Glu Ala Gln Asp Leu  Tyr Ile Leu Thr Ile  His Phe Thr
    2345                 2350                 2355

Gly His  Ser Phe Ile Tyr Gly  Lys Ile His Ser Ile  His Phe Ser
    2360                 2365                 2370

Gly His  Val Phe Thr Val Arg  Lys
    2375                 2380
```